(12) United States Patent
Ullrich et al.

(10) Patent No.: US 6,897,029 B1
(45) Date of Patent: May 24, 2005

(54) MCK-10 A NOVEL RECEPTOR TYROSINE KINASE

(75) Inventors: Axel Ullrich, München (DE); Frauke Hildegard Elisabeth Alves, Göttingen (DE)

(73) Assignee: Max Planck Gesellschaft zur Forderung der Wissenschaften, Munich (DE)

( * ) Notice: Subject to any disclaimer, the term of this patent is extended or adjusted under 35 U.S.C. 154(b) by 13 days.

(21) Appl. No.: 09/551,188

(22) Filed: Apr. 17, 2000

Related U.S. Application Data

(62) Division of application No. 08/153,397, filed on Nov. 16, 1993, now Pat. No. 6,051,397.

(51) Int. Cl.$^7$ .............................................. G01N 33/53
(52) U.S. Cl. ...................... 435/7.1; 435/7.21; 435/325; 530/350
(58) Field of Search ...................... 530/350; 536/23.5; 514/2

(56) References Cited

U.S. PATENT DOCUMENTS 6,087,144 A    7/2000   Scadden et al.

FOREIGN PATENT DOCUMENTS

| EP | 0504914 | 9/1992 |
|----|---------|--------|
| WO | 90/10234 | 9/1990 |
| WO | 95/02187 | 1/1995 |
| WO | WO 95/02187 | * 1/1995 |

OTHER PUBLICATIONS

Roussidis et al., Inhibition of receptor tyrosine kinase–based signal transduction as specific target for cancer treatment. IN VIVO, (Nov–Dec. 2002) 16 (6) 459–69.*
Traxler P. Tyrosine kinase inhibitors in cancer treatment (Part II). Expert Opinion on Therapeutic Patents, (1998) 8/12 (1599–1625).*
Traxler P.M. Protein tyrosine kinase inhibitors in cancer treatment. Expert Opinion on Therapeutic Patents, (1997) 7/6 (571–588).*
Protein tyrosine kinases as therapeutic targets in cancer chemotherapy and recent advances in the development of new inhibitors. Expert Opinion on Investigational Drugs, (1994) 3/6 (577–595).*
Haynes et al. Electrophoresis 19 :1862–1871, 1998.*
Johnson et al. Proc. Natl. Acad. Sci. USA 90: 5677–5681 (1993).
Zerlin et al. Oncogene 8: 2731–2739 (1993).
Hanks et al. Science 241: 42–52 (1988).
Poole et al. J. Mol. Biol. 153: 273–289 (1981).
Burke, Jr., Terrence R. "Protein–tyrosine Kinase Inhibitors," *Drugs of the Future* (1992), vol. 17, No. 2, pp. 119–131.
Di Marco, Eddi et al. "Molecular Cloning of trkE, a Novel trk–related Putative Tyrosine Receptor Isolated from Normal Human Keratinocytes and Widely Expressed by Normal Human Tissues," *The Journal of Biological Chemistry* (1993), vol. 268, No. 32, pp. 24290–24295, The American Society for Biochemistry and Molecular Biology, Inc.
Gusterson, R.D. et al. "Prognostic Importance of c–erbB–2 Expression in Breast Cancer," *Journal of Clinical Oncology* (1992), vol. 10, No. 7, pp. 1049–1056, American Society of Clinical Oncology.
Perez, Jose L. et al. "Identification and Chromosomal Mapping of a Receptor Tyrosine Kinase with a Putative Phospholipid Binding Sequence in its Ectodomain" *Oncogene* (1994), vol. 9, No. 1, pp. 211–219.
Karn, Thomas et al. "Structure, Expression and Chromosomal Mapping of TKT from Man and Mouse: a New Subclass of Receptor Tyrosine Kinases with a Factor VIII–like Domain," *Oncogene* (1993), vol. 8, No. 12, pp. 3433–3440.
Carter, Paul et al., "Humanization of an anti–p185$^{HER2}$ Antibody for Human Cancer Therapy," *Proc. Natl. Acad. Sci.* (1992), vol. 89, No. 10, pp. 4285–4289.
Gazit, Aviv et al. "Tyrphostins. 2. Heterocyclic and α–Substituted Benzylidenemalononitrile Tyrphostins as Potent Inhibitors of EGF Receptor and ErbB2/neu Tyrosine Kinases," *J. Med. Chem.* (1991), vol. 34, No. 6, pp. 1896–1907, American Chemical Society.

* cited by examiner

*Primary Examiner*—Lorraine Spector
*Assistant Examiner*—Eileen B. O'Hara
(74) *Attorney, Agent, or Firm*—Beth A. Burrous; Foley & Lardner LLP

(57) ABSTRACT

The present invention relates to the novel family of receptor tyrosine kinases, herein referred to as MCK-10, to nucleotide sequences and expression vectors encoding MCK-10, and to methods of inhibiting MCK-10 activity. The invention relates to differentially spliced isoforms of MCK-10 and to other members of the MCK-10 receptor tyrosine kinase family. Genetically engineered host cells that express MCK-10 may be used to evaluate and screen drugs involved in MCK-10 activation and regulation. The invention relates to the use of such drugs, in the treatment of disorders, including cancer, by modulating the activity of MCK-10.

10 Claims, 39 Drawing Sheets

Figure 2:
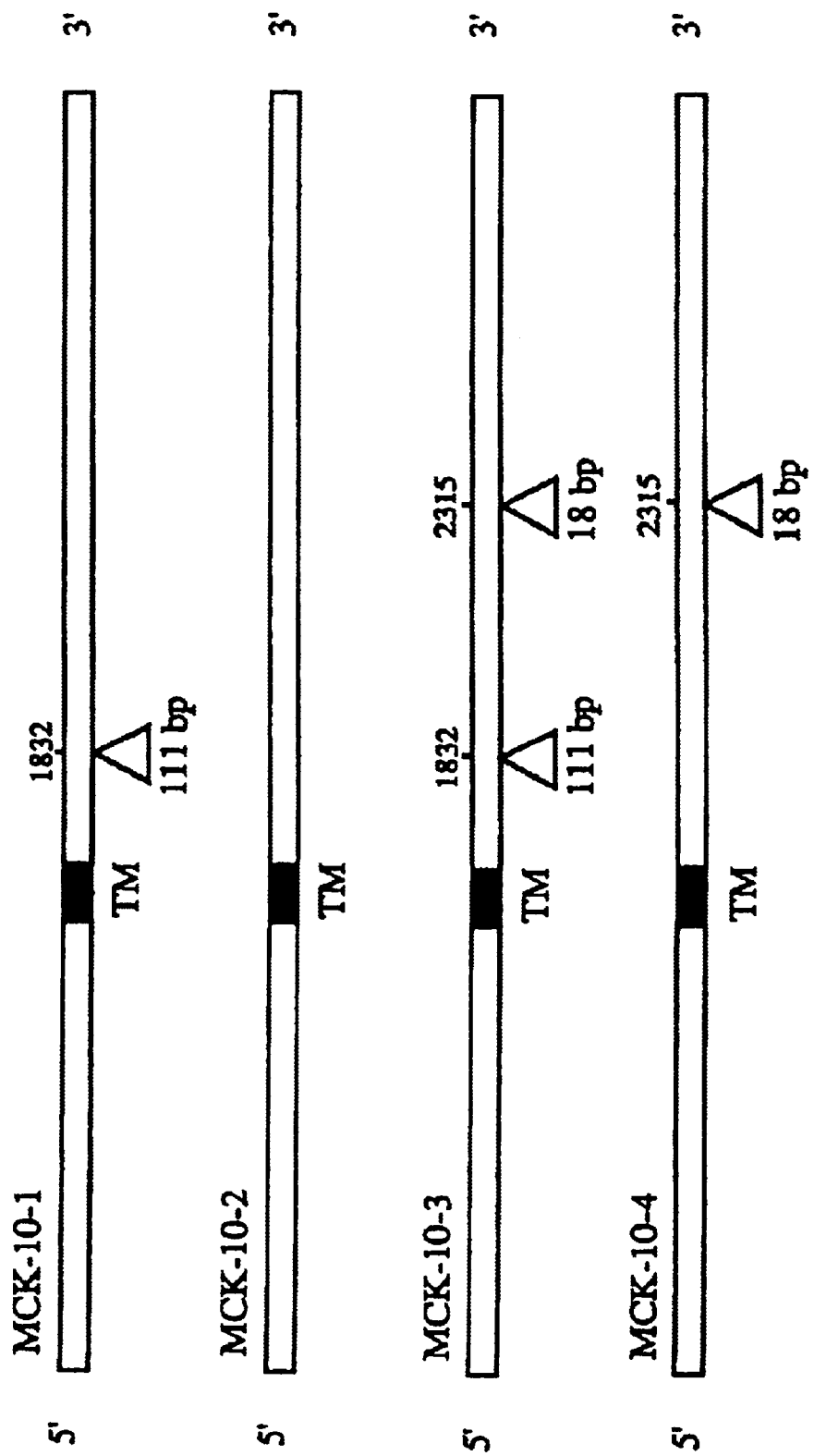

```
  1  CGGGCCTGAGACTGGGGTGACTGGGGACTGGGGACTAAGAGAATCCTGAGCTGGAGGCCCCGACAG
 61  CTGCTCTCGGGAGCCGCCTCCCGACACCCGAGCCCGGCCGCCTCCCGCCTCCCGCTC
121  CCGGCTCCTGGCTCCCCTGCCTCCCGCCCCCGCCCCCGCCGCGCCGAAGAGGCCCGCT
181  CCCGGGTCGGACGCCTGGGTCTGCCGGGAAGAGCGATGAGAGGTGTCTGAAGGTGGCTAT
241  TCACTGAGCGCGATGGGGGTTGGACTTGAAGGAATGCCAAGAGATGCTGCCCCCCCCCTTA

M  G  P  E  A  L  S  S  L  L  L  L  L  L
301  GGCCCGAGGGATCAGGAGAGCTATGGGGACCAGAGCCCTGTCATCTTTACTGCTGCTCT

V  A  S  G  D  A  D  M  K  G  H  F  D  P  A  K  C  R  Y  A
361  TGGTGGCAAGTGGAGAGATGCTGACATGAAGGGACATTTTGATCCTGCCAAGTGCCGCTATG

L  G  M  Q  D  R  T  I  P  D  S  D  I  S  A  S  S  W  S
421  CCCTGGGCATGCAGGACCGGACCATCCCAGACAGTGACATCTCTGCTTCCAGCTCCTGGT

D  S  T  A  A  R  H  S  R  L  E  S  S  D  G  D  G  A  W  C
481  CAGATTCCACTGCCGCCCGCCACAGCAGGTGGAGAGCAGTGACGGGGATGGGGCCTGGT

P  A  G  S  V  F  P  K  E  E  E  Y  L  Q  V  D  L  Q  R  L
541  GCCCCGCAGGGTCGGTGTTCCCAAGGAGGAGTACTTGCAGGTGGATCTACAACGAC

H  L  V  A  L  V  G  T  Q  G  R  H  A  G  G  L  G  K  E  F
601  TCCACCTGGTGGCTCTGGTGGGCACCCAGGGCATGCGGCATGCCGGGGGCCTGGGCAAGGAGT
```

FIG.1A

| | | |
|---|---|---|
| 115 | S R S Y R L R Y S R D G R R W M G W K D | |
| 661 | TCTCCCGGAGCTACCGGCTGCGCTGTACTCCCGGGATGGTCGGGATGGGCTGAAGG | |
| 135 | R W G Q E V I S G N E D P E G V V L K D | |
| 721 | ACCGCTGGGGTCAGGAGGTGATCTCAGGCAATGAGGACCCTGAGGGAGTGGTGCTGAAGG | |
| 155 | L G P P M V A R L V R F Y P R A D R V M | |
| 781 | ACCTTGGGCCCCCCATGGTTGCCCGACTGGTTCGCTTCTACCCCGGCGTGACCGGGTCA | |
| 175 | S V C L R V E L Y G C L W R D G L L S Y | |
| 841 | TGAGTGTCTGCGGGTAGAGCTCTATGGCTGCCTCTGGAGGGATGGACTCCTGTCTT | |
| 195 | T A P V G Q T M Y L S E A V Y L N D S T | |
| 901 | ACACCGCCCCTGTGGGCCAGACAATGTATTTATCTGAGGCCGTGTACCTCAACGACTCCA | |
| 215 | Y D G H T V G G L Q Y G G L G Q L A D G | |
| 961 | CCTATGACGGACATACCGTGGGCGGACTGCAGTATGGGGGTCTGGGCCAGCTGGCAGATG | |
| 235 | V V G L D D F R K S Q E L R V W P G Y D | |
| 1021 | GTGTGGGGCTGGATGACTTTAGAAGAGTCAGGAGCTGCGGGTCTGGCCAGGCTATG | |
| 255 | Y V G W S N H S F S S G Y V E M E F E F | |
| 1081 | ACTATGTGGGATGGAGCAACCACAGCTTCTCCAGTGGCTATGTGGAGATGGAGTTTGAGT | |

FIG.1B

FIG.1C

```
275    D R L R A F Q A M Q V H C N N M H T L G
1141   TTGACCGGCTGAGGGCCTTCCAGGCTATGCAGGTCCACTGTAACAACATGCACACGCTGG

295    A R L P G G V E C R F R R G P A M A W E
1201   GAGCCCGTCTGCCTGGCGGGGTGGAATGTCGCTTCCGGCGTGGCCCTGGCCATGGCCTGGG

315    G E P M R H N L G G N L G D P R A R A V
1261   AGGGGGAGCCCATGCGCCACAACCTAGGGGGCAACCTGGGGGACCCCAGAGCCCGGGCTG

335    S V P L G G R V A R F L Q C R F L F A G
1321   TCTCAGTGCCCCTTGGCGGGCCGTGTGGCCCGCTTCCTGCAGTGCCGCTTCCTCTTGCGG

355    P W L F S E I S F I S D V V N N S S P
1381   GGCCCCTGGTTACTCTTCAGCGAAATCTCCTTCATCTCTGATGTGGTGAACAATTCCTCTC

375    A L G G T F P P A P W P P G P P P T N
1441   CGGCACTGGGAGGCACCTTCCCGGCCCCCTGGCCGCCTGGCCCACCTCCCACCA

395    F S S L E L E P R G Q Q P V A K A E G S
1501   ACTTCAGCAGCTTGGAGCTGGAGCCCAGAGGCCAGCAGCCCGTGGCCAAGGCCGAGGGGA

415    P T A I L I G C L V A I L L L L L I I
1561   GCCCGACCGCCATCCTCATCGGCTGCCTGGTGGCCATCCTGCTCCTGCTGCTCATCA
```

```
435        A  L  M  W  R  L  H  W  R  R  L  L  S  K  A  E  R  R  V
1621       TTGCCCTCATGCTCTGGCGGCTGCACTGGCAGGCTCCTCAGCAAGGCTGAACGGAGGG

455        L  E  E  E  L  T  V  H  L  S  V  P  G  D  T  I  L  I  N  N
1681       TGTTGGAAGAGGAGCTGACGGTTCACCTCTCTGTCCCTGGGGACACTATCCTCATCAACA

475        R  P  G  P  R  E  P  P  P  Y  Q  E  P  R  P  R  G  N  P  P
1741       ACGGCCCAGGTCCTAGAGAGCCACCCCCGTACCAGGAGCCCCGGCCTCGTGGGAATCCGC

495        H  S  A  P  C  V  P  N  G  S  A  L  L  S  N  P  A  Y  R
1801       CCCACTCCGCTCCCCTGTGTCCCAATGGCTCTGCTCTCCAATCCAGCCTACC

515        L  L  L  A  T  Y  A  R  P  P  R  G  P  P  T  P  A  W
1861       GCCTCCTTCTGGCCACTTACGCCCGTCCCCGAGGCCCACACCCGCCT

535        A  K  P  T  N  T  Q  A  Y  S  G  D  Y  M  E  P  E  K  P  G
1921       GGGCCAAACCCACCAACACCCAGGCCTACAGTGGGGACTATATGGAGCCTGAGAAGCCAG

555        A  P  L  L  P  P  P  Q  N  S  V  P  H  Y  A  E  A  D  I
1981       GCGCCCCGCTTCTGCCCCCACCCCAGAACAGCGTCCCCCATTATGCCGAGGCTGACA

575        V  T  L  Q  G  V  T  G  G  N  T  Y  A  V  P  A  L  P  P  G
2041       TTGTTACCCTGCAGGGCGTCACCGGGGGCAACACACCTATGCCCTGTGTCCTGCCCCCAG
```

FIG.1D

```
595        A   V   G   D   G   P   P   R   V   D   F   F   P   R   S   R   L   R   F   K   E
2101      GGGCAGTCGGGGATGGGCCCCCAGAGTGGATTTCCCCGATCTCGACTCCGCTTCAAGG

615        K   L   G   E   G   Q   F   G   E   V   H   L   C   E   V   D   S   P   Q   D
2161      AGAAGCTTGGGGAGGGCCAGTTTGGGGAGGTGCACCTGTGTGAGGTCGACAGCCCTCAAG

635        L   V   S   L   D   F   F   P   L   N   V   R   K   G   H   P   L   L   V   A   V
2221      ATCTGGTCAGTCTTGATTTCCCCCTTAATGTGCGTAAGGGACACCCTTGCTGGTAGCTG

655        K   I   L   R   P   D   A   T   K   N   A   S   F   S   L   F   S   R   N   D
2281      TCAAGATCTTACGGCCAGATGCCACCAAGAATGCCAGCTTCTCCTTGTTCTCCAGGAATG

675        F   L   K   E   V   K   I   M   S   R   L   K   D   P   N   I   R   L   L
2341      ATTTCCTGAAAGAGGTGAAGATCATGTCGAGGCTCAAGGACCCCAACATCATTCGGCTGC

695        G   V   C   V   Q   D   D   P   L   C   M   I   T   D   Y   M   E   N   G   D
2401      TGGGCGTGTGTGTGCAGGACGACCCCCTCTGCATGATTACTGACTACATGGAGAACGGCG

715        L   N   Q   F   L   S   A   H   Q   L   E   D   K   A   A   E   G   A   P   G
2461      ACCTCAACCAGTTCCTCAGTGCCCACCAGCTGGAGGACAAGGCAGCCGAGGGGCCCTG

735        D   G   Q   A   A   Q   G   P   T   I   S   Y   P   M   L   L   H   V   A   A
2521      GGGACGGGCAGGCCGCGCAGGGCCCCACCATCAGCTACCCCAATGCTGCTGCATGTGGCAG
```

FIG.1E

```
755        Q   I   A   S   G   M   R   Y   L   A   T   L   N   F   V   H   R   D   L   A
2581      CCCAGATCGCCTCCGGCATGCGCTATCTGGCCACACTCAACTTTGTACATCGGGACCTGG

775        T   R   N   C   L   V   G   E   N   F   T   I   K   I   A   D   F   G   M   S
2641      CCACGCGGGAACTGCCTAGTTGGGGAAAAATTCACCATCAAAATGCAGACTTTGGCATGA

795        R   N   L   Y   A   G   D   Y   Y   R   V   Q   G   R   A   V   L   P   I   R
2701      GCCGGAACCTCTATGCTGGGGACTATTACCGTGTGCAGGGCCGGGCAGTGCTGCCCATCC

815        W   M   A   W   E   C   I   L   M   G   K   F   T   T   A   S   D   V   W   A
2761      GCTGGATGGCCTGGGAGTGCATCCTCATGGGGAAGTTCACGACTGCGAGTGACGTGTGGG

835        F   G   V   T   L   W   E   V   L   M   L   C   R   A   Q   P   F   G   Q   L
2821      CCTTTGGTGTGACCCTGTGGGAGGTGCTGATGCTCTGTAGGGCCCAGCCCTTTGGGCAGC

855        T   D   E   Q   V   I   E   N   A   G   E   F   F   R   D   Q   G   R   Q   V
2881      TCACCGACGAGCAGGTCATCGAGAACGCGGGGGAGTTCTTCCGGGACCAGGGCCGGCAGG

875        Y   L   S   R   P   P   A   C   P   Q   G   L   Y   E   L   M   L   R   C   W
2941      TGTACCTGTCCCGGCCGCCTGCCTGCCCGCAGGGCCTATATGAGCTGATGCTTCGGTGCT

895        S   R   E   S   E   Q   R   P   P   F   S   Q   L   H   R   F   L   A   E   D
3001      GGAGCCGGGAGTCTGAGCAGCGACCACCCTTTCCCAGCTGCATCGGTTCCTGGCAGAGG
```

FIG.1F

```
            A  L  N  T  V
915
3061  ATGCACTCAACACGGTGTGAATCACACATCCAGCTGCCCCTCCCTCAGGGAGTGATCCAG
3121  GGGAAGCCAGTGACACTAAAACAAGAGAGGACACCTCTGCCCTTCCCCTCCCGA
3181  CAGCCCATCACCTCTAATAGAGGCAGTGAGACTGCAGGTGGGCTGGCACCCAGGGAG
3241  CTGATGCCCCTTCTGCGCCCAGCACACTCATGTCCCCTTCCTGTCCTGTTCTCCTTCC
3301  TAGAAGCCCTGTCGCCCACCCAGGTCCTGTGATGGGATCCTCTCCACCCTCT
3361  AGCCATCCCTTGGGGAAGGGTGGGAGAGAAATATAGGATACACTGGACATGGCCATTG
3421  GAGCACCTGGGCCCCCACTGGACAACACTGATTCCTGAGAGGTGCGCCCCAGCTTC
3481  TCTCTCCCTGTCACACACTGGACCCCACTGGCTGAGAAATCTGGGGGTGAGGAGGACAAGA
3541  AGGAGGAAAAATGTTCCTGAAACACTGGACCCTAGCCCCGCCCTCAGTCACCC
3601  CTCCTCCACTTGTCCAGTCTTGTAGCTAGAACTTCTAAGCCTATACGTTTCTGTGGAG
3661  CCACTTCCCACTTGCCAGTCTTGTAGCTAGAACTTCTAAGCCTATACGTTTCTGTGGAG
3721  TAAATATGGATTGTGCCACATTGATTTTCTATAATCACTTGGGGTTTGTACATTTTGGG
3781  TCTAGTGTAGCTGCCACATTGATTTTTACTAATATATGGACCTAGCTTGAGGCAATTTAATCCCT
3841  GGAGAGACACAGATTTTACTAATATATGGACCTAGCTTGAGGCAATTTAATCCCT
3901  GCACTAGGCAGGTAATAATAAAGGTTGAGTTTTCCACAAAAAAAAAAACCGGAAT
3961  TC
```

FIG.1G

```
         gcacgagcggcacgaglccalgalclclllccalcclccclllcclglllgclcacllcl
      2  ─────────┼─────────┼─────────┼─────────┼─────────┼─────────┼─  61
         cgtgclcgccglgclcagglaclagagaaagglaggagggaaagglclllcgaglgaaga
    b                                                                   - llcllgclcalcllggagaclglgcaalcccagallaaclacaaacagagaagagclgg
     62  ─────────┼─────────┼─────────┼─────────┼─────────┼─────────┼─ 121
         aaagaacgaglagaacclclgacacgllagggclaallgalglllglclcllclcgacc
    b                                                                   - lgalagclccagagclcagagaaaggagglclclllcaagaaglclggclclcaaagcc
    122  ─────────┼─────────┼─────────┼─────────┼─────────┼─────────┼─ 181
         aclalcgagglclcgaglclclllcclccagagaaalgllcllcagaccgagagllcgg
    b                                                                   - lccalcaagggagacclacaagllgcclggggllcglgclclagaaaglllccaaggllt
    182  ─────────┼─────────┼─────────┼─────────┼─────────┼─────────┼─ 241
         aggtaglllcclclggalglllcaacggaccccaaglcacgagalclllcaaggllccaaa
    b                                                                   - glggcllgaallallclaaagaagclgaaalaallgaagagaagcagaggccagclglll
    242  ─────────┼─────────┼─────────┼─────────┼─────────┼─────────┼─ 301
         caccgaacllaalaagalllcllcgaclllallaacllclcllcglclccggclgacaaa
    b                                                                   - llgaggalcclgclccacagagaalgclclgcacccgllgalaclccagllccaacacca
    302  ─────────┼─────────┼─────────┼─────────┼─────────┼─────────┼─ 361
         aaclcclaggacgagglglclcllacgagacglgggcaaclalgagglcaagglglggl
    b                                                                   - lcllclgagalgalcclgallcccagaalgclcllgglgclgllcclgclgclgcclalc
    362  ─────────┼─────────┼─────────┼─────────┼─────────┼─────────┼─ 421
         agaagclclaclaggaclaagggclcllacgagaaccacgacaaggacgacgacggalag
    b         H  I  L  I  P  R  M  L  L  V  L  F  L  L  L  P  I         - llgagllclgcaaaagclcagglaalccagclalalgccgclalcclclgggcalglca
    422  ─────────┼─────────┼─────────┼─────────┼─────────┼─────────┼─ 481
         aaclcaagacgllllcgaglccaallagglcgalalacggcgalaggagacccglacagl
    b      L  S  S  A  K  A  Q  V  N  P  A  I  C  R  Y  P  L  G  M  S   - ggaggccagallccagalgaggacalcacagcllccaglcaglggtcagaglccacagcl
    482  ─────────┼─────────┼─────────┼─────────┼─────────┼─────────┼─ 541
         cclccgglclaagglclaclcclglaglglcgaagglcaglcaccglclcagglglcga
    b      G  G  Q  I  P  D  E  D  I  T  A  S  S  Q  W  S  E  S  T  A   -
```

FIG.3A

```
       gccaaatatggaaggctggactcagaagaaggggatggagcctggtgccctgagattcca
  542  ────────┼────────┼────────┼────────┼────────┼────────┼─ 601
       cggtttatacctaccgacctgagtcttcttccctacctcggaccacgggactctaaggt b       A  K  Y  G  R  L  D  S  E  E  G  D  G  A  W  C  P  E  I  P   ─ gtggaacctgatgacctgaaggagtttctgcagattgacttgcacaccctccatttlatc
  602  ────────┼────────┼────────┼────────┼────────┼────────┼─ 661
       caccttggactactggacttcctcaaagacgtctaactgaacgtgtgggaggtaaaatag b       V  E  P  D  D  L  K  E  F  L  Q  I  D  L  H  T  L  H  F  I   ─ actctggtggggacccggggcgccgagcaggaggtcatggcatcgagtttgcccccatg
  662  ────────┼────────┼────────┼────────┼────────┼────────┼─ 721
       tgagaccaccccctgggtccccgcggctcgtcctccagtaccgtagctcaaacgggggtac b       T  L  V  G  T  Q  G  R  R  A  G  G  H  G  I  E  F  A  P  M   ─ tacaagatcaattacagtcgggatggcactcgctggatctcttggcggaaccgtcatggg
  722  ────────┼────────┼────────┼────────┼────────┼────────┼─ 781
       atgttctagttaatgtcagccctaccgtgagcgacctagagaaccgccttggcagtaccc b       Y  K  I  N  Y  S  R  D  G  T  R  W  I  S  W  R  N  R  H  G   ─ aaacaggtgctggatggaaatagtaaccccctatgacattttcctaaaggacttggagccg
  762  ────────┼────────┼────────┼────────┼────────┼────────┼─ 841
       tttgtccacgacctaccttatcattggggatactgtaaaaggattttcctgaacctcggc b       K  Q  V  L  D  G  N  S  N  P  Y  D  I  F  L  K  D  L  E  P   ─ cccattgtagccagattgtccggttcattccagtcaccgaccactccatgaatgtgtgt
  842  ────────┼────────┼────────┼────────┼────────┼────────┼─ 901
       gggtaacatcggtctaaacaggccaagtaaggtcagtggctggtgaggtacttacacaca b       P  I  V  A  R  F  V  R  F  I  P  V  T  D  H  S  M  N  V  C   ─ atgagagtggagctttacggCTGTGTCTGGCTAGATGGCTTGGTGTCTTACAATGCTCCA
  902  ────────┼────────┼────────┼────────┼────────┼────────┼─ 961
       tactctcacctcgaaatgccGACACAGACCGATCTACCGAACCACAGAATGTTACGAGGT b       M  R  V  E  L  Y  G  C  V  W  L  D  G  L  V  S  Y  N  A  P   ─
```

FIG.3B

```
          GCTGGGCACCAGTTTGTACTCCCTGGAGGTTCCATCATTTATCTGAATGATTCTGTCTAT
    962   ------+---------+---------+---------+---------+---------+- 1021
          CGACCCGTGGTCAAACATGAGGGACCTCCAAGGTAGTAAATAGACTTACTAAGACAGATA b          A  G  Q  Q  F  V  L  P  G  G  S  I  I  Y  L  N  D  S  V  Y   -

GATGGAGCTGTTGGATACAGCATGACAGAAGGGCTAGGCCAATTGACCGATGGTGTGTCT
   1022   ------+---------+---------+---------+---------+---------+- 1081
          CTACCTCGACAACCTATGTCGTACTGTCTTCCCGATCCGGTTAACTGGCTACCACACAGA b          D  G  A  V  G  Y  S  M  T  E  G  L  G  Q  L  T  D  G  V  S   -

GGCCTGGACGATTTCACCCAGACCCATGAATACCACGTGTGGCCCGGCTATGACTATGTG
   1082   ------+---------+---------+---------+---------+---------+- 1141
          CCGGACCTGCTAAAGTGGGTCTGGGTACTTATGGTGCACACCGGGCCGATACTGATACAC b          G  L  D  D  F  T  Q  T  H  E  Y  H  V  W  P  G  Y  D  Y  V   -

GGCTGGCGGAACGAGAGTGCCACCAATGGCTACATTGAGATCATGTTTGAATTTGACCGC
   1142   ------+---------+---------+---------+---------+---------+- 1201
          CCGACCGCCTTGCTCTCACGGTGGTTACCGATGTAACTCTAGTACAAACTTAAACTGGCG b          G  W  R  N  E  S  A  T  N  G  Y  I  E  I  M  F  E  F  D  R   -

ATCAGGAATTTCACTACCATGAAGGTCCACTGCAACAACATGTTTGCTAAAGGTGTGAAG
   1202   ------+---------+---------+---------+---------+---------+- 1261
          TAGTCCTTAAAGTGATGGTACTTCCAGGTGACGTTGTTGTACAAACGATTTCCACACTTC b          I  R  N  F  T  T  M  K  V  H  C  N  N  M  F  A  K  G  V  K   -

ATCTTTAAGGAGGTACAGTGCTACTTCCGCTCTGAAGCCAGTGAGTGGGTACCTAATGCC
   1262   ------+---------+---------+---------+---------+---------+- 1321
          TAGAAATTCCTCCATGTCACGATGAAGGCGAGACTTCGGTCACTCACCCATGGATTACGG b          I  F  K  E  V  Q  C  Y  F  R  S  E  A  S  E  W  V  P  N  A   -

ATTTCCTTccccctttgtcctggatgacgtcaaccccagtgctcggtttgtcacggtgcct
   1322   ------+---------+---------+---------+---------+---------+- 1381
          TAAAGGAAggggggaacaggacctactgcagttggggtcacgagccaaacagtgccacgga b          I  S  F  P  L  V  L  D  D  V  N  P  S  A  R  F  V  T  V  P   -
```

FIG. 3C

```
        ctccaccaccgaatggccagtgccatcaagtgtcaataccatttt gcagatacctggctg
  1382 ──────┼──────┼──────┼──────┼──────┼──────┼ 1441
        gaggtggtggcttaccggtcacggtagttcacagttatggtaaaacgtctatggacctac b        L  H  H  R  M  A  S  A  I  K  C  Q  Y  H  F  A  D  T  W  M atgttcagtgagatcaccttccaatcagatgctgcaatgtacaacaactctgaagccctg
  1442 ──────┼──────┼──────┼──────┼──────┼──────┼ 1501
        tacaagtcactctagtggaaggttagtctacgacgttacatgttgttgagacttcgggac b        M  F  S  E  I  T  F  Q  S  D  A  A  M  Y  N  N  S  E  A  L cccacctctcctatggcacccacaacctatgatccaatgcttaaagttgatgacagcaac
  1502 ──────┼──────┼──────┼──────┼──────┼──────┼ 1561
        gggtggagaggatacc gtgggtgttggatactaggttacgaatttcaactactgtcgttg b        P  T  S  P  M  A  P  T  T  Y  D  P  M  L  K  V  D  D  S  N actcggatcctgattggctgcttggtggccatcatctttatcctcctggccatcattgtc
  1562 ──────┼──────┼──────┼──────┼──────┼──────┼ 1621
        tgagcctaggactaaccgacgaaccaccggtagtagaaataggaggaccggtagtaacag b        T  R  I  L  I  G  C  L  V  A  I  F  I  L  L  A  I  I  V atcatcctctggaggcagttctggcagaaaatgctggagaaggcttctcggaggatgctg
  1622 ──────┼──────┼──────┼──────┼──────┼──────┼ 1681
        tagtaggagacctccgtcaagaccgtcttttacgacctcttccgaagagcctcctacgac b        I  I  L  W  R  Q  F  W  Q  K  M  L  E  K  A  S  R  R  M  L gatgatgaaatgacagtcagcctttccctgccaagtgattccagcatgttcaacaataac
  1682 ──────┼──────┼──────┼──────┼──────┼──────┼ 1741
        ctactactttactgtcagtcggaaagggacggttcactaagatcgtacaagttgttattg b        D  D  E  M  T  V  S  L  S  L  P  S  D  S  S  M  F  N  N  N cgctcctcatccctagtgaacaagggtccaactcgacttacgatcgcatctttcccctt
  1742 ──────┼──────┼──────┼──────┼──────┼──────┼ 1801
        gcgaggagtagtggatcacttgttcccaggttgagctgaatgctagcgtagaaaggggaa b        R  S  S  S  P  S  E  Q  G  S  N  S  T  Y  D  R  I  F  P  L
```

FIG.3D

```
           cgcccIgocIocCAGGAGCCATCCAGGCTGATACGAAAACTCCCAGAATTTGCTCCAGGG
     1802  ─────┼─────┼─────┼─────┼─────┼─────┼─────  1861
           gcgggacIgaIgGTCCTCGGTAGGTCCGACTATGCTTTTGAGGGTCTTAAACGAGGTCCC b         R  P  D  Y  Q  E  P  S  R  L  I  R  K  L  P  E  F  A  P  G   -

GAGGAGGAGTCAGGCTGCAGCGGTGTTGTGAAGCCAGTCCAGCCCAGTGGCCCTGAGGGG
     1862  ─────┼─────┼─────┼─────┼─────┼─────┼─────  1921
           CTCCTCCTCAGTCCGACGTCGCCACAACACTTCGGTCAGGTCGGGTCACCGGGACTCCCC b         E  E  E  S  G  C  S  G  V  V  K  P  V  Q  P  S  G  P  E  G   -

GTGCCCCACTATGCAGAGGCTGACATAGTGAACCTCCAAGGAGTGACAGGAGGCAACACA
     1922  ─────┼─────┼─────┼─────┼─────┼─────┼─────  1981
           CACGGGGTGATACGTCTCCGACTGTATCACTTGGAGGTTCCTCACTGTCCTCCGTTGTGT b         V  P  H  Y  A  E  A  D  I  V  K  L  Q  G  V  T  G  G  N  T   -

TACTCAGTGCCTGCCGTCACCATGGACCTGCTCTCAGGAAAAGATGTGGCTGTGGAGGAG
     1982  ─────┼─────┼─────┼─────┼─────┼─────┼─────  2041
           ATGAGTCACGGACGGCAGTGGTACCTGGACGAGAGTCCTTTTCTACACCGACACCTCCTC b         Y  S  V  P  A  V  T  M  D  L  L  S  G  K  D  V  A  V  E  E   -

TTCCCCAGGAAACTCCTAACTTTCAAAGAGAAGCTGGGAGAAGGACAGTTTGGGGAGGTT
     2042  ─────┼─────┼─────┼─────┼─────┼─────┼─────  2101
           AAGGGGTCCTTTGAGGATTGAAAGTTTCTCTTCGACCCTCTTCCTGTCAAACCCCTCCAA b         F  P  R  K  L  L  T  F  K  E  K  L  G  E  G  Q  F  G  E  V   -

CATCTCTGTGAAGTGGAGGGAATGGAAAAAATTCAAAGACAAAGATTTTGCCCTAGATGTC
     2102  ─────┼─────┼─────┼─────┼─────┼─────┼─────  2161
           GTAGAGACACTTCACCTCCCTTACCTTTTTTAAGTTTCTGTTTCTAAAACGGGATCTACAG b         H  L  C  E  V  E  G  M  E  K  F  K  D  K  D  F  A  L  D  V   -

AGTGCCAACCAGCCTGTCCTGGTGGCTGTGAAAATGCTCCGAGCAGATGCCAACAAGAAT
     2162  ─────┼─────┼─────┼─────┼─────┼─────┼─────  2221
           TCACGGTTGGTCGGACAGGACCACCGACACTTCTACGAGGCTCGTCTACGGTTGTTCTTA b         S  A  N  Q  P  V  L  V  A  V  K  M  L  R  A  D  A  N  K  N   -
```

FIG. 3E

```
              GCCAGGAATGATTTTCTTAAGGAGATAAAGATCATGTCTCGGCTCAAGGACCCAAACATC
        2222 ————+————+————+————+————+————+ 2281
              CGGTCCTTACTAAAAGAATTCCTCTATTTCTAGTACAGAGCCGAGTTCCTGGGTTTGTAG b     A  R  N  D  F  L  K  E  I  K  I  M  S  R  L  K  D  P  N  I   -

ATCCATCTATTAGCTGTGTGTATCACTGATGACCCTCTCTGTATGATCACTGAATACATG
        2282 ————+————+————+————+————+————+ 2341
              TAGGTAGATAATCGACACACATAGTGACTACTGGGAGAGACATACTAGTGACTTATGTAC b     I  H  L  L  A  V  C  I  T  D  D  P  L  C  M  I  T  E  Y  M   -

GAGAATGGAGATCTCAATCAGTTTCTTTCCCGCCACGAGCCCCCTAATTCTTCCTCCAGC
        2342 ————+————+————+————+————+————+ 2401
              CTCTTACCTCTAGAGTTAGTCAAAGAAAGGGCGGTGCTCGGGGATTAAGAAGGAGGTCG

E  N  G  D  L  N  Q  F  L  S  R  H  E  P  P  N  S  S  S  S   -

GATGTACGCACTGTCAGTTACACCAATCTGAAGTTTATGGCTACCCAAATTGCCTCTGGC
        2402 ————+————+————+————+————+————+ 2461
              CTACATGCGTGACAGTCAATGTGGTTAGACTTCAAATACCGATGGGTTTAACGGAGACCG b     D  V  R  T  V  S  Y  T  N  L  K  F  M  A  T  Q  I  A  S  G   -

ATGAAGTACCTTTCCTCTCTTAATTTTGTTCACCGAGATCTGGCCACACGAAACTGTTTA
        2462 ————+————+————+————+————+————+ 2521
              TACTTCATGGAAAGGAGAGAATTAAAACAAGTGGCTCTAGACCGGTGTGCTTTGACAAAT b     M  K  Y  L  S  S  L  N  F  V  H  R  D  L  A  T  R  N  C  L   -

GTGGGTAAGAACTACACAATCAAGATAGCTGACTTTGGAATGAGCAGGAACCTGTACAGT
        2522 ————+————+————+————+————+————+ 2581
              CACCCATTCTTGATGTGTTAGTTCTATCGACTGAAACCTTACTCGTCCTTGGACATGTCA b     V  G  K  N  Y  T  I  K  I  A  D  F  G  M  S  R  N  L  Y  S   -

GGTGACTATTACCGGATCCAGGGCCGGGCAGTGCTCCCTATCCGCTGGATGTCTTGGGAG
        2582 ————+————+————+————+————+————+ 2641
              CCACTGATAATGGCCTAGGTCCCGGCCCGTCACGAGGGATAGGCGACCTACAGAACCCTC b     G  D  Y  Y  R  I  Q  G  R  A  V  L  P  I  R  W  M  S  W  E   -
```

FIG. 3F

```
              AGTATCTTGCTGGGCAAGTTCACTACAGCAAGTGATGTGTGGGCCTTTGGGGTTACTTTG
       2642   ------+------+------+------+------+------+  2701
              TCATAGAAGGACCCGTTCAAGTGATGTCGTTCACTACACACCCGGAAACCCCAATGAAAC b         S  I  L  L  G  K  F  T  T  A  S  D  V  W  A  F  G  V  T  L    -

TGGGAGACTTTCACCTTTTGTCAAGAACAGCCCTATTCCCAGCTGTCAGATGAACAGGTT
       2702   ------+------+------+------+------+------+  2761
              ACCCTCTGAAAGTGGAAAACAGTTCTTGTCGGGATAAGGGTCGACAGTCTACTTGTCCAA b         W  E  T  F  T  F  C  Q  E  Q  P  Y  S  Q  L  S  D  E  Q  V    -

ATTGAGAATACTGGAGAGTTCTTCCGAGACCAAGGGAGGCAGACTTACCTCCCTCAACCA
       2762   ------+------+------+------+------+------+  2821
              TAACTCTTATGACCTCTCAAGAAGGCTCTGGTTCCCTCCGTCTGAATGGAGGGAGTTGGT b         I  E  K  T  G  E  F  F  R  D  Q  G  R  Q  T  Y  L  P  Q  P    -

GCCATTTGTCCTGACTCTGTGTATAAGCTGATGCTCAGCTGCTGGAGAAGAGATACGAAG
       2822   ------+------+------+------+------+------+  2881
              CGGTAAACAGGACTGAGACACATATTCGACTACGAGTCGACGACCTCTTCTCTATGCTTC b         A  I  C  P  D  S  V  Y  K  L  M  L  S  C  W  R  R  D  T  K    -

AACCGTCCCTCATTCCAAGAAATCCACCTTCTGCTCCTTCAACAAGGCGACGAGTGATGC
       2882   ------+------+------+------+------+------+  2941
              TTGGCAGGGAGTAAGGTTCTTTAGGTGGAAGACGAGGAAGTTGTTCCGCTGCTCACTACG b         N  R  P  S  F  Q  E  I  H  L  L  L  Q  Q  G  D  E             -

TGTCAGTGCCTGGCCATGTTCCTACGGCTCAGGTCCTCCCTACAAGACCTACCACTCACC
       2942   ------+------+------+------+------+------+  3001
              ACAGTCACGGACCGGTACAAGGATGCCGAGTCCAGGAGGGATGTTCTGGATGGTGAGTGG b                                                                        -

CATGCCTATGCCACTCCATCTGGACATTTAATGAAACTGAGAGACAGAGGCCTTGTTTGCT
       3002   ------+------+------+------+------+------+  3061
              GTACGGATACGGTGAGGTAGACCTGTAAATTACTTTGACTCTCTGTCTCCGAACAAACGA
```

FIG.3G b

```
       TTGCCCTCTTTTCCTGGTCACCCCCACTCCCTACCCCTGACTCATATATACTTTTTTTTT
3062 ——————+—————————+—————————+—————————+—————————+—————————+— 3121
       AACGGGAGAAAAGGACCAGTGGGGGTGAGGGATGGGGACTGAGTATATATGAAAAAAAAA
``` b

```
       TTACATTAAAGAACTAAAAAAAAAAAAAAAAAAAGCCG
3122 ——————+—————————+—————————+————— 3158
       AATGTAATTTCTTGATTTTTTTTTTTTTTTTTTTCCGC
``` b

FIG.3H

```
  1   MILIPRMLLVLFLLLPILSSA...KAQVNPAICRYPLGMSGCQIPDEDIT     47  CCK-2
      : |  | |:|||  : |:.     |::.:|| |||:|||  :   |||.||.
  1   ..MGPEALSSLLLLLLVASGDADMKGHFDPAKCRYALGMQDRTIPDSDIS     48  MCK-10

48   ASSQHSESTAAKYGRLDSEEGDGAWCPEIPVEPDOLKEFLQIDLHTLHFI     97
      |||  ||:||||:..:||:|..:|||||||. .| |.: .|:||:|| ||::
 49   ASSSWSDSTAARHSRLESSDCDGAWCPAGSVFPKE.EEYLQVDLQRLHLV    97

98   TLVGTQGRRAGGHGIEFAPMYKINYSRDGTRWISWRNRHGKQVLDGNSNP   147
      .||||||||:|||  |  ||..  |::.||||| ||::|::|  |.:|:.||.:|
 98   ALVGTQGRHAGGLGKEFSRSYRLRYSRDGRRWMGWKDRWGQEVISGNEDP   147

148   YDIFLKDLEPPIVARFVRFIPVTDHSMWCMRVELYGCVWLDGLVSYNAP    197
      :::.||||:||:|||:|||.|  .|:  |.||:|||||||:|  |||:||.||
148   EGVVLKDLGPPWVARLVRFYPRADRVWSVCLRVELYGCLWRDGLLSYTAP   197

198   AGQQFVLPGCSIIYLNDSVYDG.AVGYSMTEGLGQLTDGVSGLDDFTQTH   246
      .||  : |.::  :|||||.|||  .|| :|||||-||| ||||| ..:
198   VGQTMYLSEA..VYLNDSTYDGHTVGGLQYGGLGQLADGVVGLDDFRKSQ   245

247   EYHVWPCYDYVCWRNESATNGYIEIMFEFDRIRNFTTMKVHCNMMFAKGV   296
      |.:|||||||||.|.|  ..||:|: |||||:|.| .|.||||||  .|.
246   ELRVWPCYDYVCWSNHSFSSGYVEMEFEFDRLRAFQAMQVHCNMMHTLGA   295

297   KIFKEVQC.YFRSEASEWVPNAISFPLVLDDVNPSARFVTVPLHHRMASA   345
      ::  :|:|  :  |:.|  .| .| .:::.   |. :  .:|.|| |.||| |:|.
296   RLPGGVECRFRRCPAMAWEGEPMRHNLCGNLCDPRARAVSVPLGGRVARF   345

346   IKCQYHFADTWMAFSEITFQSDAAMYNNSEALPTS............   380
      :.|.: ||:.|::|||||.| || .: |.|.||...
346   LQCRFLFAGPWLLFSEISFISD.VVNNSSPALGGTFPPAPWWPPGPPPTN  394

381   ....PWAPTTYDPMLKVDDSNTRILIGCLVAIIFILLAIIVIILWRQFWQ  426  TRANSMEMBRANE
      .:.|  . :| |.::| | |||||||||:|| ||.::|||  |.        REGION
395   FSSLELEPRGQQPVAKAEGSPTAILIGCLVAILLLLLIIALMLWRLHWR   444

427   KMLEKASRRMLDDEMTVSLSLPSDSSMFNNNRSSSPSEQGSNSTYDRIFP   476
      ::|.||.||:|::|:||  ||:|:|.   ::||...:..
445   RLLSKAERRVLEEELTVHLSVPGDTILINNRPGPREP.............  481
```

FIG.4A

```
                477 LRPOYQEPSRLIRKLPEFAPGEEESGCSG........WKPVQPSGPEGV  518  CCK-2
                    |.||||..  ..  ..  :....::|::||    ...  :.|....::|
                482 ..PPYQEPRPRGNPPHSAPCVPNGSAYSGDYMEPEKPGAPLLPPPPQNSV 529  MCK-10

519 PHYAEADIVNLQGVTGGNTYSVPAVTMDLLSGKDVAVEEFPRKLLTFKEK 568
                    ||||||||.|||||||||||.|||:. :  :::  .. | :|||. | ||||
                530 PHYAEADIVTLQGVTGGNTYAVPALPPGAVGDGPPRV.DFPRSRLRFKEK 578

. . .
    ATP         569 LGEGQFGEVHLCEVEGMEKFKDKDFALDVSANQPVLVAVKMLRADANKNA 618
    BINDING SITE    ||||||||||||||::  :..:  . ||:|:|.  .:|:|||||:||:||.|||
                579 LGEGQFGEVHLCEVDSPQDLVSLDFPLNVRKGHPLLVAVKILRPDATKNA 628

619 RNDFLKEIKIMSRLKDPNIIHLLAVCITDDPLCMITEYMENGDLNQFLSR 668
                    ||||||:|||||||||||:||:||: |||||||:|||||||||||||||
                629 RNDFLKEVKIMSRLKDPNIIRLLGVCVDDDPLCMITDYMENGDLNQFLSA 678
```

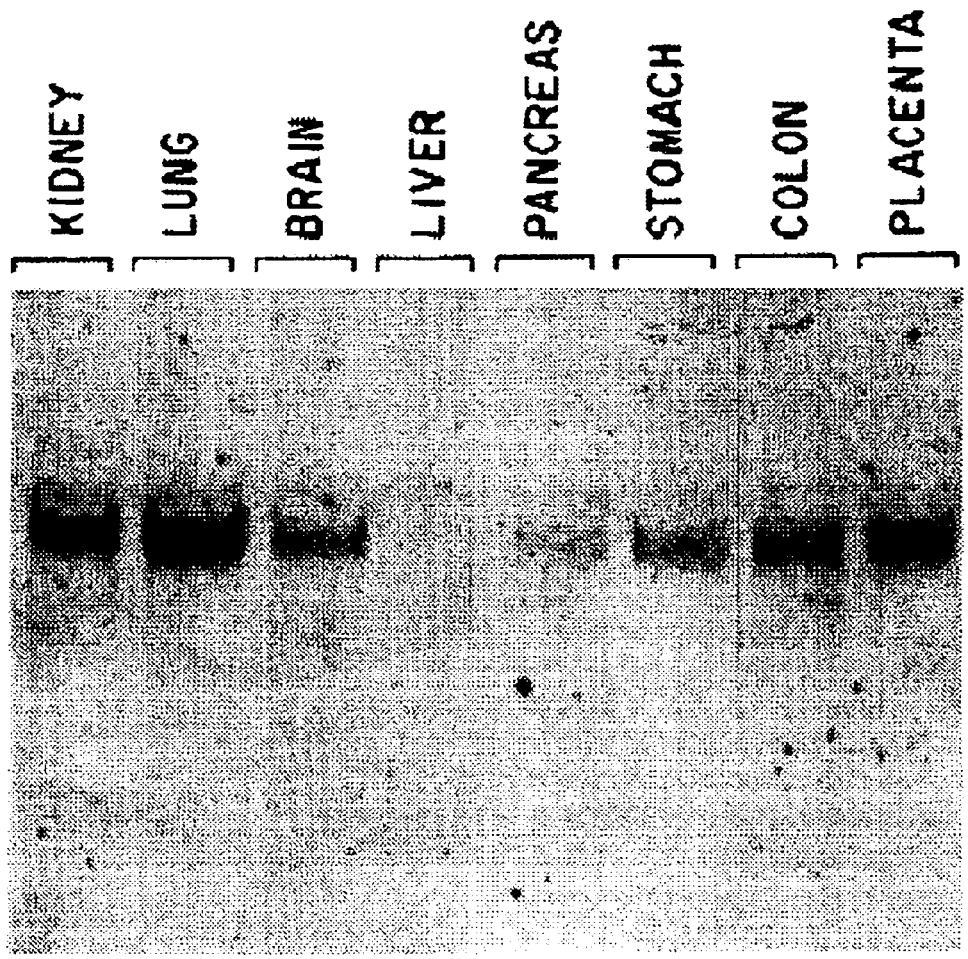
FIG.5A

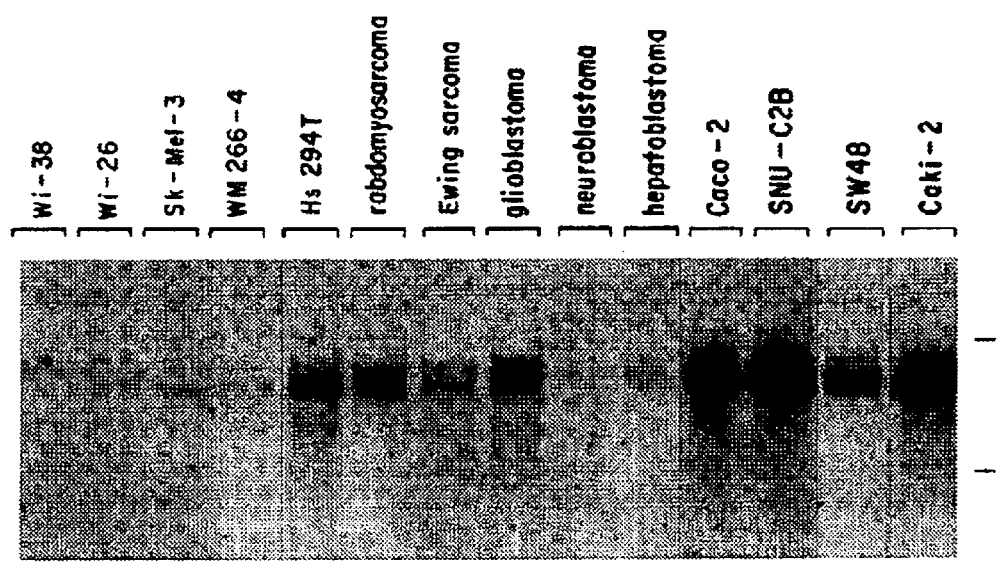
FIG.5C

Lightfield

Darkfield

Lightfield

Darkfield

Lightfield

Darkfield

Lightfield

Darkfield

Lightfield

Darkfield

Lightfield

Darkfield

Lightfield

Darkfield

Lightfield

Darkfield

Lightfield

Darkfield

Lightfield

Darkfield

Lightfield

Darkfield

Lightfield

Darkfield

Lightfield

Darkfield

Lightfield

Darkfield

Lightfield

Darkfield

```
                        SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
        (A) LENGTH: 3962 base pairs
        (B) TYPE: nucleic acid
        (C) STRANDEDNESS: double
        (D) TOPOLOGY: both (ii) MOLECULE TYPE: cDNA to mRNA (iii) HYPOTHETICAL: NO (iv) ANTI-SENSE: NO (ix) FEATURE:
        (A) NAME/KEY: CDS
        (B) LOCATION: 321..3077

(xi) SEQUENCE DESCRIPTION: SEQ ID NO: 1:

CGGGCCTGAG ACTGGGGTGA CTGGGACCTA AGAGAATCCT GAGCTGGAGG CCCCCGACAG      60

CTGCTCTCGG GAGCCGCCTC CCGACACCCG AGCCCCGCCG GCGCCTCCCG CTCCCGGCTC     120

CCGGCTCCTG GCTCCCTCCG CCTCCCCCGC CCCTCGCCCC GCCGCCGAAG AGGCCCCGCT     180

CCCGGGTCGG ACGCCTGGGT CTGCCGGGAA GAGCGATGAG AGGTGTCTGA AGGTGGCTAT     240

TCACTGAGCG ATGGGGTTGG ACTTGAAGGA ATGCCAAGAG ATGCTGCCCC CACCCCCTTA     300

GGCCCGAGGG ATCAGGAGCT ATG GGA CCA GAG GCC CTG TCA TCT TTA CTG        350
                     Met Gly Pro Glu Ala Leu Ser Ser Leu Leu
                       1               5                  10

CTG CTG CTC TTG GTG GCA AGT GGA GAT GCT GAC ATG AAG GGA CAT TTT      398
Leu Leu Leu Leu Val Ala Ser Gly Asp Ala Asp Met Lys Gly His Phe
                 15                  20                  25

GAT CCT GCC AAG TGC CGC TAT GCC CTG GGC ATG CAG GAC CGG ACC ATC      446
Asp Pro Ala Lys Cys Arg Tyr Ala Leu Gly Met Gln Asp Arg Thr Ile
             30                  35                  40

CCA GAC AGT GAC ATC TCT GCT TCC AGC TCC TGG TCA GAT TCC ACT GCC      494
Pro Asp Ser Asp Ile Ser Ala Ser Ser Ser Trp Ser Asp Ser Thr Ala
         45                  50                  55

GCC CGC CAC AGC AGG TTG GAG AGC AGT GAC GGG GAT GGG GCC TGG TGC      542
Ala Arg His Ser Arg Leu Glu Ser Ser Asp Gly Asp Gly Ala Trp Cys
     60                  65                  70

CCC GCA GGG TCG GTG TTT CCC AAG GAG GAG GAG TAC TTG CAG GTG GAT      590
Pro Ala Gly Ser Val Phe Pro Lys Glu Glu Glu Tyr Leu Gln Val Asp
 75                  80                  85                  90
```

| | |
|---|---|
| CTA CAA CGA CTC CAC CTG GTG GCT CTG GTG GGC ACC CAG GGA CGG CAT<br>Leu Gln Arg Leu His Leu Val Ala Leu Val Gly Thr Gln Gly Arg His<br>             95                     100                     105 | 638 |
| GCC GGG GGC CTG GGC AAG GAG TTC TCC CGG AGC TAC CGG CTG CGT TAC<br>Ala Gly Gly Leu Gly Lys Glu Phe Ser Arg Ser Tyr Arg Leu Arg Tyr<br>           110                     115                     120 | 686 |
| TCC CGG GAT GGT CGC CGC TGG ATG GGC TGG AAG GAC CGC TGG GGT CAG<br>Ser Arg Asp Gly Arg Arg Trp Met Gly Trp Lys Asp Arg Trp Gly Gln<br>               125                     130                     135 | 734 |
| GAG GTG ATC TCA GGC AAT GAG GAC CCT GAG GGA GTG GTG CTG AAG GAC<br>Glu Val Ile Ser Gly Asn Glu Asp Pro Glu Gly Val Val Leu Lys Asp<br>        140                     145                     150 | 782 |
| CTT GGG CCC CCC ATG GTT GCC CGA CTG GTT CGC TTC TAC CCC CGG GCT<br>Leu Gly Pro Pro Met Val Ala Arg Leu Val Arg Phe Tyr Pro Arg Ala<br>155                     160                     165                     170 | 830 |
| GAC CGG GTC ATG AGT GTC TGT CTG CGG GTA GAG CTC TAT GGC TGC CTC<br>Asp Arg Val Met Ser Val Cys Leu Arg Val Glu Leu Tyr Gly Cys Leu<br>                    175                     180                     185 | 878 |
| TGG AGG GAT GGA CTC CTG TCT TAC ACC GCC CCT GTG GGG CAG ACA ATG<br>Trp Arg Asp Gly Leu Leu Ser Tyr Thr Ala Pro Val Gly Gln Thr Met<br>               190                     195                     200 | 926 |
| TAT TTA TCT GAG GCC GTG TAC CTC AAC GAC TCC ACC TAT GAC GGA CAT<br>Tyr Leu Ser Glu Ala Val Tyr Leu Asn Asp Ser Thr Tyr Asp Gly His<br>           205                     210                     215 | 974 |
| ACC GTG GGC GGA CTG CAG TAT GGG GGT CTG GGC CAG CTG GCA GAT GGT<br>Thr Val Gly Gly Leu Gln Tyr Gly Gly Leu Gly Gln Leu Ala Asp Gly<br>        220                     225                     230 | 1022 |
| GTG GTG GGG CTG GAT GAC TTT AGG AAG AGT CAG GAG CTG CGG GTC TGG<br>Val Val Gly Leu Asp Asp Phe Arg Lys Ser Gln Glu Leu Arg Val Trp<br>235                     240                     245                     250 | 1070 |
| CCA GGC TAT GAC TAT GTG GGA TGG AGC AAC CAC AGC TTC TCC AGT GGC<br>Pro Gly Tyr Asp Tyr Val Gly Trp Ser Asn His Ser Phe Ser Ser Gly<br>                    255                     260                     265 | 1118 |
| TAT GTG GAG ATG GAG TTT GAG TTT GAC CGG CTG AGG GCC TTC CAG GCT<br>Tyr Val Glu Met Glu Phe Glu Phe Asp Arg Leu Arg Ala Phe Gln Ala<br>               270                     275                     280 | 1166 |
| ATG CAG GTC CAC TGT AAC AAC ATG CAC ACG CTG GGA GCC CGT CTG CCT<br>Met Gln Val His Cys Asn Asn Met His Thr Leu Gly Ala Arg Leu Pro<br>           285                     290                     295 | 1214 |
| GGC GGG GTG GAA TGT CGC TTC CGG CGT GGC CCT GCC ATG GCC TGG GAG<br>Gly Gly Val Glu Cys Arg Phe Arg Arg Gly Pro Ala Met Ala Trp Glu<br>        300                     305                     310 | 1262 |
| GGG GAG CCC ATG CGC CAC AAC CTA GGG GGC AAC CTG GGG GAC CCC AGA<br>Gly Glu Pro Met Arg His Asn Leu Gly Gly Asn Leu Gly Asp Pro Arg<br>315                     320                     325                     330 | 1310 |
| GCC CGG GCT GTC TCA GTG CCC CTT GGC GGC CGT GTG GCT CGC TTT CTG<br>Ala Arg Ala Val Ser Val Pro Leu Gly Gly Arg Val Ala Arg Phe Leu<br>               335                     340                     345 | 1358 |
| CAG TGC CGC TTC CTC TTT GCG GGG CCC TGG TTA CTC TTC AGC GAA ATC<br>Gln Cys Arg Phe Leu Phe Ala Gly Pro Trp Leu Leu Phe Ser Glu Ile<br>           350                     355                     360 | 1406 |
| TCC TTC ATC TCT GAT GTG GTG AAC AAT TCC TCT CCG GCA CTG GGA GGC<br>Ser Phe Ile Ser Asp Val Val Asn Asn Ser Ser Pro Ala Leu Gly Gly<br>        365                     370                     375 | 1454 |
| ACC TTC CCG CCA GCC CCC TGG TGG CCG CCT GGC CCA CCT CCC ACC AAC<br>Thr Phe Pro Pro Ala Pro Trp Trp Pro Pro Gly Pro Pro Pro Thr Asn<br>380                     385                     390 | 1502 |
| TTC AGC AGC TTG GAG CTG GAG CCC AGA GGC CAG CAG CCC GTG GCC AAG<br>Phe Ser Ser Leu Glu Leu Glu Pro Arg Gly Gln Gln Pro Val Ala Lys<br>395                     400                     405                     410 | 1550 |

```
GCC GAG GGG AGC CCG ACC GCC ATC CTC ATC GGC TGC CTG GTG GCC ATC      1598
Ala Glu Gly Ser Pro Thr Ala Ile Leu Ile Gly Cys Leu Val Ala Ile
                415                 420                 425

ATC CTG CTC CTG CTG CTC ATC ATT GCC CTC ATG CTC TGG CGG CTG CAC      1646
Ile Leu Leu Leu Leu Leu Ile Ile Ala Leu Met Leu Trp Arg Leu His
            430                 435                 440

TGG CGC AGG CTC CTC AGC AAG GCT GAA CGG AGG GTG TTG GAA GAG GAG      1694
Trp Arg Arg Leu Leu Ser Lys Ala Glu Arg Arg Val Leu Glu Glu Glu
        445                 450                 455

CTG ACG GTT CAC CTC TCT GTC CCT GGG GAC ACT ATC CTC ATC AAC AAC      1742
Leu Thr Val His Leu Ser Val Pro Gly Asp Thr Ile Leu Ile Asn Asn
    460                 465                 470

CGC CCA GGT CCT AGA GAG CCA CCC CCG TAC CAG GAG CCC CGG CCT CGT      1790
Arg Pro Gly Pro Arg Glu Pro Pro Pro Tyr Gln Glu Pro Arg Pro Arg
475                 480                 485                 490

GGG AAT CCG CCC CAC TCC GCT CCC TGT GTC CCC AAT GGC TCT GCG TTG      1838
Gly Asn Pro Pro His Ser Ala Pro Cys Val Pro Asn Gly Ser Ala Leu
                495                 500                 505

CTG CTC TCC AAT CCA GCC TAC CGC CTC CTT CTG GCC ACT TAC GCC CGT      1886
Leu Leu Ser Asn Pro Ala Tyr Arg Leu Leu Leu Ala Thr Tyr Ala Arg
            510                 515                 520

CCC CCT CGA GGC CCG GGC CCC CCC ACA CCC GCC TGG GCC AAA CCC ACC      1934
Pro Pro Arg Gly Pro Gly Pro Pro Thr Pro Ala Trp Ala Lys Pro Thr
        525                 530                 535

AAC ACC CAG GCC TAC AGT GGG GAC TAT ATG GAG CCT GAG AAG CCA GGC      1982
Asn Thr Gln Ala Tyr Ser Gly Asp Tyr Met Glu Pro Glu Lys Pro Gly
    540                 545                 550

GCC CCG CTT CTG CCC CCA CCT CCC CAG AAC AGC GTC CCC CAT TAT GCC      2030
Ala Pro Leu Leu Pro Pro Pro Pro Gln Asn Ser Val Pro His Tyr Ala
555                 560                 565                 570

GAG GCT GAC ATT GTT ACC CTG CAG GGC GTC ACC GGG GGC AAC ACC TAT      2078
Glu Ala Asp Ile Val Thr Leu Gln Gly Val Thr Gly Gly Asn Thr Tyr
                575                 580                 585

GCT GTG CCT GCA CTG CCC CCA GGG GCA GTC GGG GAT GGG CCC CCC AGA      2126
Ala Val Pro Ala Leu Pro Pro Gly Ala Val Gly Asp Gly Pro Pro Arg
            590                 595                 600

GTG GAT TTC CCT CGA TCT CGA CTC CGC TTC AAG GAG AAG CTT GGC GAG      2174
Val Asp Phe Pro Arg Ser Arg Leu Arg Phe Lys Glu Lys Leu Gly Glu
        605                 610                 615

GGC CAG TTT GGG GAG GTG CAC CTG TGT GAG GTC GAC AGC CCT CAA GAT      2222
Gly Gln Phe Gly Glu Val His Leu Cys Glu Val Asp Ser Pro Gln Asp
    620                 625                 630

CTG GTC AGT CTT GAT TTC CCC CTT AAT GTG CGT AAG GGA CAC CCT TTG      2270
Leu Val Ser Leu Asp Phe Pro Leu Asn Val Arg Lys Gly His Pro Leu
635                 640                 645                 650

CTG GTA GCT GTC AAG ATC TTA CGG CCA GAT GCC ACC AAG AAT GCC AGC      2318
Leu Val Ala Val Lys Ile Leu Arg Pro Asp Ala Thr Lys Asn Ala Ser
                655                 660                 665

TTC TCC TTG TTC TCC AGG AAT GAT TTC CTG AAA GAG GTG AAG ATC ATG      2366
Phe Ser Leu Phe Ser Arg Asn Asp Phe Leu Lys Glu Val Lys Ile Met
            670                 675                 680

TCG AGG CTC AAG GAC CCC AAC ATC ATT CGG CTG CTG GGC GTG TGT GTG      2414
Ser Arg Leu Lys Asp Pro Asn Ile Ile Arg Leu Leu Gly Val Cys Val
        685                 690                 695

CAG GAC GAC CCC CTC TGC ATG ATT ACT GAC TAC ATG GAG AAC GGC GAC      2462
Gln Asp Asp Pro Leu Cys Met Ile Thr Asp Tyr Met Glu Asn Gly Asp
    700                 705                 710

CTC AAC CAG TTC CTC AGT GCC CAC CAG CTG GAG GAC AAG GCA GCC GAG      2510
Leu Asn Gln Phe Leu Ser Ala His Gln Leu Glu Asp Lys Ala Ala Glu
```

```
                                                                    -continued 715                 720                 725                 730
GGG GCC CCT GGG GAC GGG CAG GCT GCG CAG GGG CCC ACC ATC AGC TAC    2558
Gly Ala Pro Gly Asp Gly Gln Ala Ala Gln Gly Pro Thr Ile Ser Tyr
                735                 740                 745

CCA ATG CTG CTG CAT GTG GCA GCC CAG ATC GCC TCC GGC ATG CGC TAT    2606
Pro Met Leu Leu His Val Ala Ala Gln Ile Ala Ser Gly Met Arg Tyr
            750                 755                 760

CTG GCC ACA CTC AAC TTT GTA CAT CGG GAC CTG GCC ACG CGG AAC TGC    2654
Leu Ala Thr Leu Asn Phe Val His Arg Asp Leu Ala Thr Arg Asn Cys
                765                 770                 775

CTA GTT GGG GAA AAT TTC ACC ATC AAA ATC GCA GAC TTT GGC ATG AGC    2702
Leu Val Gly Glu Asn Phe Thr Ile Lys Ile Ala Asp Phe Gly Met Ser
            780                 785                 790

CGG AAC CTC TAT GCT GGG GAC TAT TAC CGT GTG CAG GGC CGG GCA GTG    2750
Arg Asn Leu Tyr Ala Gly Asp Tyr Tyr Arg Val Gln Gly Arg Ala Val
795                 800                 805                 810

CTG CCC ATC CGC TGG ATG GCC TGG GAG TGC ATC CTC ATG GGG AAG TTC    2798
Leu Pro Ile Arg Trp Met Ala Trp Glu Cys Ile Leu Met Gly Lys Phe
                815                 820                 825

ACG ACT GCG AGT GAC GTG TGG GCC TTT GGT GTG ACC CTG TGG GAG GTG    2846
Thr Thr Ala Ser Asp Val Trp Ala Phe Gly Val Thr Leu Trp Glu Val
            830                 835                 840

CTG ATG CTC TGT AGG GCC CAG CCC TTT GGG CAG CTC ACC GAC GAG CAG    2894
Leu Met Leu Cys Arg Ala Gln Pro Phe Gly Gln Leu Thr Asp Glu Gln
                845                 850                 855

GTC ATC GAG AAC GCG GGG GAG TTC TTC CGG GAC CAG GGC CGG CAG GTG    2942
Val Ile Glu Asn Ala Gly Glu Phe Phe Arg Asp Gln Gly Arg Gln Val
            860                 865                 870

TAC CTG TCC CGG CCG CCT GCC TGC CCG CAG GGC CTA TAT GAG CTG ATG    2990
Tyr Leu Ser Arg Pro Pro Ala Cys Pro Gln Gly Leu Tyr Glu Leu Met
875                 880                 885                 890

CTT CGG TGC TGG AGC CGG GAG TCT GAG CAG CGA CCA CCC TTT TCC CAG    3038
Leu Arg Cys Trp Ser Arg Glu Ser Glu Gln Arg Pro Pro Phe Ser Gln
                895                 900                 905

CTG CAT CGG TTC CTG GCA GAG GAT GCA CTC AAC ACG GTG TGAATCACAC    3087
Leu His Arg Phe Leu Ala Glu Asp Ala Leu Asn Thr Val
            910                 915

ATCCAGCTGC CCCTCCCTCA GGGAGTGATC CAGGGGAAGC CAGTGACACT AAAACAAGAG    3147

GACACAATGG CACCTCTGCC CTTCCCCTCC CGACAGCCCA TCACCTCTAA TAGAGGCAGT    3207

GAGACTGCAG GTGGGCTGGG CCCACCCAGG GAGCTGATGC CCCTTCTCCC CTTCCTGGAC    3267

ACACTCTCAT GTCCCCTTCC TGTTCTTCCT TCCTAGAAGC CCCTGTCGCC CACCCAGCTG    3327

GTCCTGTGGA TGGGATCCTC TCCACCCTCC TCTAGCCATC CCTTGGGGAA GGGTGGGGAG    3387

AAATATAGGA TAGACACTGG ACATGGCCCA TTGGAGCACC TGGGCCCCAC TGGACAACAC    3447

TGATTCCTGG AGAGGTGGCT GCGCCCCAGC TTCTCTCTCC CTGTCACACA CTGGACCCCA    3507

CTGGCTGAGA ATCTGGGGGT GAGGAGGACA AGAAGGAGAG GAAAATGTTT CCTTGTGCCT    3567

GCTCCTGTAC TTGTCCTCAG CTTGGGCTTC TTCCTCCTCC ATCACCTGAA ACACTGGACC    3627

TGGGGGTAGC CCCGCCCCAG CCCTCAGTCA CCCCCACTTC CCACTTGCAG TCTTGTAGCT    3687

AGAACTTCTC TAAGCCTATA CGTTTCTGTG GAGTAAATAT TGGGATTGGG GGGAAAGAGG    3747

GAGCAACGGC CCATAGCCTT GGGGTTGGAC ATCTCTAGTG TAGCTGCCAC ATTGATTTTT    3807

CTATAATCAC TTGGGGTTTG TACATTTTTG GGGGAGAGA CACAGATTTT TACACTAATA    3867

TATGGACCTA GCTTGAGGCA ATTTTAATCC CCTGCACTAG GCAGGTAATA ATAAAGGTTG    3927

AGTTTTCCAC AAAAAAAAAA AAAAAACCGG AATTC                              3962
```

(2) INFORMATION FOR SEQ ID NO: 2:

(i) SEQUENCE CHARACTERISTICS:
        (A) LENGTH: 919 amino acids
        (B) TYPE: amino acid
        (D) TOPOLOGY: unknown (ii) MOLECULE TYPE: protein (xi) SEQUENCE DESCRIPTION: SEQ ID NO: 2:

```
Met Gly Pro Glu Ala Leu Ser Ser Leu Leu Leu Leu Leu Val Ala
 1               5                  10                  15

Ser Gly Asp Ala Asp Met Lys Gly His Phe Asp Pro Ala Lys Cys Arg
                20                  25                  30

Tyr Ala Leu Gly Met Gln Asp Arg Thr Ile Pro Asp Ser Asp Ile Ser
            35                  40                  45

Ala Ser Ser Ser Trp Ser Asp Ser Thr Ala Ala Arg His Ser Arg Leu
        50                  55                  60

Glu Ser Ser Asp Gly Asp Gly Ala Trp Cys Pro Ala Gly Ser Val Phe
 65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
                100                 105                 110

Glu Phe Ser Arg Ser Tyr Arg Leu Arg Tyr Ser Arg Asp Gly Arg Arg
            115                 120                 125

Trp Met Gly Trp Lys Asp Arg Trp Gly Gln Glu Val Ile Ser Gly Asn
        130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
            180                 185                 190

Ser Tyr Thr Ala Pro Val Gly Gln Thr Met Tyr Leu Ser Glu Ala Val
        195                 200                 205

Tyr Leu Asn Asp Ser Thr Tyr Asp Gly His Thr Val Gly Gly Leu Gln
    210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Ser Gly Tyr Val Glu Met Glu Phe
            260                 265                 270

Glu Phe Asp Arg Leu Arg Ala Phe Gln Ala Met Gln Val His Cys Asn
        275                 280                 285

Asn Met His Thr Leu Gly Ala Arg Leu Pro Gly Gly Val Glu Cys Arg
    290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
            340                 345                 350
```

```
Ala Gly Pro Trp Leu Leu Phe Ser Glu Ile Ser Phe Ile Ser Asp Val
        355                 360                 365

Val Asn Asn Ser Ser Pro Ala Leu Gly Gly Thr Phe Pro Pro Ala Pro
    370                 375                 380

Trp Trp Pro Pro Gly Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
                405                 410                 415

Ala Ile Leu Ile Gly Cys Leu Val Ala Ile Ile Leu Leu Leu Leu Leu
            420                 425                 430

Ile Ile Ala Leu Met Leu Trp Arg Leu His Trp Arg Arg Leu Leu Ser
        435                 440                 445

Lys Ala Glu Arg Arg Val Leu Glu Glu Glu Leu Thr Val His Leu Ser
    450                 455                 460

Val Pro Gly Asp Thr Ile Leu Ile Asn Asn Arg Pro Gly Pro Arg Glu
465                 470                 475                 480

Pro Pro Pro Tyr Gln Glu Pro Arg Pro Arg Gly Asn Pro Pro His Ser
                485                 490                 495

Ala Pro Cys Val Pro Asn Gly Ser Ala Leu Leu Leu Ser Asn Pro Ala
            500                 505                 510

Tyr Arg Leu Leu Leu Ala Thr Tyr Ala Arg Pro Pro Arg Gly Pro Gly
        515                 520                 525

Pro Pro Thr Pro Ala Trp Ala Lys Pro Thr Asn Thr Gln Ala Tyr Ser
    530                 535                 540

Gly Asp Tyr Met Glu Pro Glu Lys Pro Gly Ala Pro Leu Leu Pro Pro
545                 550                 555                 560

Pro Pro Gln Asn Ser Val Pro His Tyr Ala Glu Ala Asp Ile Val Thr
                565                 570                 575

Leu Gln Gly Val Thr Gly Gly Asn Thr Tyr Ala Val Pro Ala Leu Pro
            580                 585                 590

Pro Gly Ala Val Gly Asp Gly Pro Pro Arg Val Asp Phe Pro Arg Ser
        595                 600                 605

Arg Leu Arg Phe Lys Glu Lys Leu Gly Glu Gly Gln Phe Gly Glu Val
    610                 615                 620

His Leu Cys Glu Val Asp Ser Pro Gln Asp Leu Val Ser Leu Asp Phe
625                 630                 635                 640

Pro Leu Asn Val Arg Lys Gly His Pro Leu Leu Val Ala Val Lys Ile
                645                 650                 655

Leu Arg Pro Asp Ala Thr Lys Asn Ala Ser Phe Ser Leu Phe Ser Arg
            660                 665                 670

Asn Asp Phe Leu Lys Glu Val Lys Ile Met Ser Arg Leu Lys Asp Pro
        675                 680                 685

Asn Ile Ile Arg Leu Leu Gly Val Cys Val Gln Asp Asp Pro Leu Cys
    690                 695                 700

Met Ile Thr Asp Tyr Met Glu Asn Gly Asp Leu Asn Gln Phe Leu Ser
705                 710                 715                 720

Ala His Gln Leu Glu Asp Lys Ala Ala Glu Gly Ala Pro Gly Asp Gly
                725                 730                 735

Gln Ala Ala Gln Gly Pro Thr Ile Ser Tyr Pro Met Leu Leu His Val
            740                 745                 750

Ala Ala Gln Ile Ala Ser Gly Met Arg Tyr Leu Ala Thr Leu Asn Phe
        755                 760                 765

Val His Arg Asp Leu Ala Thr Arg Asn Cys Leu Val Gly Glu Asn Phe
```

-continued

```
                770                  775                 780
Thr Ile Lys Ile Ala Asp Phe Gly Met Ser Arg Asn Leu Tyr Ala Gly
785                 790                  795                 800

Asp Tyr Tyr Arg Val Gln Gly Arg Ala Val Leu Pro Ile Arg Trp Met
                805                  810                 815

Ala Trp Glu Cys Ile Leu Met Gly Lys Phe Thr Thr Ala Ser Asp Val
                820                  825                 830

Trp Ala Phe Gly Val Thr Leu Trp Glu Val Leu Met Leu Cys Arg Ala
                835                  840                 845

Gln Pro Phe Gly Gln Leu Thr Asp Glu Gln Val Ile Glu Asn Ala Gly
850                 855                  860

Glu Phe Phe Arg Asp Gln Gly Arg Gln Val Tyr Leu Ser Arg Pro Pro
865                 870                  875                 880

Ala Cys Pro Gln Gly Leu Tyr Glu Leu Met Leu Arg Cys Trp Ser Arg
                885                  890                 895

Glu Ser Glu Gln Arg Pro Pro Phe Ser Gln Leu His Arg Phe Leu Ala
                900                  905                 910

Glu Asp Ala Leu Asn Thr Val
           915
```

(2) INFORMATION FOR SEQ ID NO: 3:

(i) SEQUENCE CHARACTERISTICS:
        (A) LENGTH: 3157 base pairs
        (B) TYPE: nucleic acid
        (C) STRANDEDNESS: both
        (D) TOPOLOGY: both (ii) MOLECULE TYPE: cDNA to mRNA (iii) HYPOTHETICAL: NO (iv) ANTI-SENSE: NO (ix) FEATURE:
        (A) NAME/KEY: CDS
        (B) LOCATION: 370..2934

(xi) SEQUENCE DESCRIPTION: SEQ ID NO: 3:

```
GCACGAGCGG CACGAGTCCA TGATCTCTTT CCATCCTCCC TTTCCTGTTT GCTCACTTCT      60

TTTCTTGCTC ATCTTGGAGA CTGTGCAATC CCAGATTAAC TACAAACAGA GAAGAGCTGG     120

TGATAGCTCC AGAGCTCAGA GAAAGGAGGT CTCTTTACAA GAAGTCTGGC TCTCAAAGCC     180

TCCATCAAGG GAGACCTACA AGTTGCCTGG GGTTCAGTGC TCTAGAAAGT TCCAAGGTTT     240

GTGGCTTGAA TTATTCTAAA GAAGCTGAAA TAATTGAAGA GAAGCAGAGG CCAGCTGTTT     300

TTGAGGATCC TGCTCCACAG AGAATGCTCT GCACCCGTTG ATACTCCAGT TCCAACACCA     360

TCTTCTGAG ATG ATC CTG ATT CCC AGA ATG CTC TTG GTG CTG TTC CTG        408
          Met Ile Leu Ile Pro Arg Met Leu Leu Val Leu Phe Leu
            1               5                  10

CTG CTG CCT ATC TTG AGT TCT GCA AAA GCT CAG GTT AAT CCA GCT ATA      456
Leu Leu Pro Ile Leu Ser Ser Ala Lys Ala Gln Val Asn Pro Ala Ile
 15                  20                  25

TGC CGC TAT CCT CTG GGC ATG TCA GGA GGC CAG ATT CCA GAT GAG GAC      504
Cys Arg Tyr Pro Leu Gly Met Ser Gly Gly Gln Ile Pro Asp Glu Asp
 30                  35                  40                  45

ATC ACA GCT TCC AGT CAG TGG TCA GAG TCC ACA GCT GCC AAA TAT GGA      552
Ile Thr Ala Ser Ser Gln Trp Ser Glu Ser Thr Ala Ala Lys Tyr Gly
                 50                  55                  60

AGG CTG GAC TCA GAA GAA GGG GAT GGA GCC TGG TGC CCT GAG ATT CCA      600
```

```
                                                                        -continued Arg Leu Asp Ser Glu Glu Gly Asp Gly Ala Trp Cys Pro Glu Ile Pro
             65                  70                  75

GTG GAA CCT GAT GAC CTG AAG GAG TTT CTG CAG ATT GAC TTG CAC ACC          648
Val Glu Pro Asp Asp Leu Lys Glu Phe Leu Gln Ile Asp Leu His Thr
         80                  85                  90

CTC CAT TTT ATC ACT CTG GTG GGG ACC CAG GGG CGC CAT GCA GGA GGT          696
Leu His Phe Ile Thr Leu Val Gly Thr Gln Gly Arg His Ala Gly Gly
     95                 100                 105

CAT GGC ATC GAG TTT GCC CCC ATG TAC AAG ATC AAT TAC AGT CGG GAT          744
His Gly Ile Glu Phe Ala Pro Met Tyr Lys Ile Asn Tyr Ser Arg Asp
110                 115                 120                 125

GGC ACT CGC TGG ATC TCT TGG CGG AAC CGT CAT GGG AAA CAG GTG CTG          792
Gly Thr Arg Trp Ile Ser Trp Arg Asn Arg His Gly Lys Gln Val Leu
                130                 135                 140

GAT GGA AAT AGT AAC CCC TAT GAC ATT TTC CTA AAG GAC TTG GAG CCG          840
Asp Gly Asn Ser Asn Pro Tyr Asp Ile Phe Leu Lys Asp Leu Glu Pro
            145                 150                 155

CCC ATT GTA GCC AGA TTT GTC CGG TTC ATT CCA GTC ACC GAC CAC TCC          888
Pro Ile Val Ala Arg Phe Val Arg Phe Ile Pro Val Thr Asp His Ser
        160                 165                 170

ATG AAT GTG TGT ATG AGA GTG GAG CTT TAC GGC TGT GTC TGG CTA GAT          936
Met Asn Val Cys Met Arg Val Glu Leu Tyr Gly Cys Val Trp Leu Asp
    175                 180                 185

GGC TTG GTG TCT TAC AAT GCT CCA GCT GGG CAG CAG TTT GTA CTC CCT          984
Gly Leu Val Ser Tyr Asn Ala Pro Ala Gly Gln Gln Phe Val Leu Pro
190                 195                 200                 205

GGA GGT TCC ATC ATT TAT CTG AAT GAT TCT GTC TAT GAT GGA GCT GTT         1032
Gly Gly Ser Ile Ile Tyr Leu Asn Asp Ser Val Tyr Asp Gly Ala Val
                210                 215                 220

GGA TAC AGC ATG ACA GAA GGG CTA GGC CAA TTG ACC GAT GGT GTG TCT         1080
Gly Tyr Ser Met Thr Glu Gly Leu Gly Gln Leu Thr Asp Gly Val Ser
            225                 230                 235

GGC CTG GAC GAT TTC ACC CAG ACC CAT GAA TAC CAC GTG TGG CCC GGC         1128
Gly Leu Asp Asp Phe Thr Gln Thr His Glu Tyr His Val Trp Pro Gly
        240                 245                 250

TAT GAC TAT GTG GGC TGG CGG AAC GAG AGT GCC ACC AAT GGC TAC ATT         1176
Tyr Asp Tyr Val Gly Trp Arg Asn Glu Ser Ala Thr Asn Gly Tyr Ile
    255                 260                 265

GAG ATC ATG TTT GAA TTT GAC CGC ATC AGG AAT TTC ACT ACC ATG AAG         1224
Glu Ile Met Phe Glu Phe Asp Arg Ile Arg Asn Phe Thr Thr Met Lys
270                 275                 280                 285

GTC CAC TGC AAC AAC ATG TTT GCT AAA GGT GTG AAG ATC TTT AAG GAG         1272
Val His Cys Asn Asn Met Phe Ala Lys Gly Val Lys Ile Phe Lys Glu
                290                 295                 300

GTA CAG TGC TAC TTC CGC TCT GAA GCC AGT GAG TGG GAA CCT AAT GCC         1320
Val Gln Cys Tyr Phe Arg Ser Glu Ala Ser Glu Trp Glu Pro Asn Ala
            305                 310                 315

ATT TCC TTC CCC CTT GTC CTG GAT GAC GTC AAC CCC AGT GCT CGG TTT         1368
Ile Ser Phe Pro Leu Val Leu Asp Asp Val Asn Pro Ser Ala Arg Phe
        320                 325                 330

GTC ACG GTG CCT CTC CAC CAC CGA ATG GCC AGT GCC ATC AAG TGT CAA         1416
Val Thr Val Pro Leu His His Arg Met Ala Ser Ala Ile Lys Cys Gln
    335                 340                 345

TAC CAT TTT GCA GAT ACC TGG ATG ATG TTC AGT GAG ATC ACC TTC CAA         1464
Tyr His Phe Ala Asp Thr Trp Met Met Phe Ser Glu Ile Thr Phe Gln
350                 355                 360                 365

TCA GAT GCT GCA ATG TAC AAC AAC TCT GAA GCC CTG CCC ACC TCT CCT         1512
Ser Asp Ala Ala Met Tyr Asn Asn Ser Glu Ala Leu Pro Thr Ser Pro
                370                 375                 380
```

```
ATG GCA CCC ACA ACC TAT GAT CCA ATG CTT AAA GTT GAT GAC AGC AAC      1560
Met Ala Pro Thr Thr Tyr Asp Pro Met Leu Lys Val Asp Asp Ser Asn
            385                 390                 395

ACT CGG ATC CTG ATT GGC TGC TTG GTG GCC ATC ATC TTT ATC CTC CTG      1608
Thr Arg Ile Leu Ile Gly Cys Leu Val Ala Ile Ile Phe Ile Leu Leu
        400                 405                 410

GCC ATC ATT GTC ATC ATC CTC TGG AGG CAG TTC TGG CAG AAA ATG CTG      1656
Ala Ile Ile Val Ile Ile Leu Trp Arg Gln Phe Trp Gln Lys Met Leu
    415                 420                 425

GAG AAG GCT TCT CGG AGG ATG CTG GAT GAT GAA ATG ACA GTC AGC CTT      1704
Glu Lys Ala Ser Arg Arg Met Leu Asp Asp Glu Met Thr Val Ser Leu
430                 435                 440                 445

TCC CTG CCA AGT GAT TCT AGC ATG TTC AAC AAT AAC CGC TCC TCA TCA      1752
Ser Leu Pro Ser Asp Ser Ser Met Phe Asn Asn Asn Arg Ser Ser Ser
                450                 455                 460

CCT AGT GAA CAA GGG TCC AAC TCG ACT TAC GAT CGC ATC TTT CCC CTT      1800
Pro Ser Glu Gln Gly Ser Asn Ser Thr Tyr Asp Arg Ile Phe Pro Leu
            465                 470                 475

CGC CCT GAC TAC CAG GAG CCA TCC AGG CTG ATA CGA AAA CTC CCA GAA      1848
Arg Pro Asp Tyr Gln Glu Pro Ser Arg Leu Ile Arg Lys Leu Pro Glu
        480                 485                 490

TTT GCT CCA GGG GAG GAG GAG TCA GGC TGC AGC GGT GTT GTG AAG CCA      1896
Phe Ala Pro Gly Glu Glu Glu Ser Gly Cys Ser Gly Val Val Lys Pro
    495                 500                 505

GTC CAG CCC AGT GGC CCT GAG GGG GTG CCC CAC TAT GCA GAG GCT GAC      1944
Val Gln Pro Ser Gly Pro Glu Gly Val Pro His Tyr Ala Glu Ala Asp
510                 515                 520                 525

ATA GTG AAC CTC CAA GGA GTG ACA GGA GGC AAC ACA TAC TCA GTG CCT      1992
Ile Val Asn Leu Gln Gly Val Thr Gly Gly Asn Thr Tyr Ser Val Pro
                530                 535                 540

GCC GTC ACC ATG GAC CTG CTC TCA GGA AAA GAT GTG GCT GTG GAG GAG      2040
Ala Val Thr Met Asp Leu Leu Ser Gly Lys Asp Val Ala Val Glu Glu
            545                 550                 555

TTC CCC AGG AAA CTC CTA ACT TTC AAA GAG AAG CTG GGA GAA GGA CAG      2088
Phe Pro Arg Lys Leu Leu Thr Phe Lys Glu Lys Leu Gly Glu Gly Gln
        560                 565                 570

TTT GGG GAG GTT CAT CTC TGT GAA GTG GAG GGA ATG GAA AAA TTC AAA      2136
Phe Gly Glu Val His Leu Cys Glu Val Glu Gly Met Glu Lys Phe Lys
    575                 580                 585

GAC AAA GAT TTT GCC CTA GAT GTC AGT GCC AAC CAG CCT GTC CTG GTG      2184
Asp Lys Asp Phe Ala Leu Asp Val Ser Ala Asn Gln Pro Val Leu Val
590                 595                 600                 605

GCT GTG AAA ATG CTC CGA GCA GAT GCC AAC AAG AAT GCC AGG AAT GAT      2232
Ala Val Lys Met Leu Arg Ala Asp Ala Asn Lys Asn Ala Arg Asn Asp
                610                 615                 620

TTT CTT AAG GAG ATA AAG ATC ATG TCT CGG CTC AAG GAC CCA AAC ATC      2280
Phe Leu Lys Glu Ile Lys Ile Met Ser Arg Leu Lys Asp Pro Asn Ile
            625                 630                 635

ATC CAT CTA TTA TCT GTG TGT ATC ACT GAT GAC CCT CTC TGT ATG ATC      2328
Ile His Leu Leu Ser Val Cys Ile Thr Asp Asp Pro Leu Cys Met Ile
        640                 645                 650

ACT GAA TAC ATG GAG AAT GGA GAT CTC AAT CAG TTT CTT TCC CGC CAC      2376
Thr Glu Tyr Met Glu Asn Gly Asp Leu Asn Gln Phe Leu Ser Arg His
    655                 660                 665

GAG CCC CCT AAT TCT TCC TCC AGC GAT GTA CGC ACT GTC AGT TAC ACC      2424
Glu Pro Pro Asn Ser Ser Ser Ser Asp Val Arg Thr Val Ser Tyr Thr
670                 675                 680                 685

AAT CTG AAG TTT ATG GCT ACC CAA ATT GCC TCT GGC ATG AAG TAC CTT      2472
Asn Leu Lys Phe Met Ala Thr Gln Ile Ala Ser Gly Met Lys Tyr Leu
                690                 695                 700
```

```
TCC TCT CTT AAT TTT GTT CAC CGA GAT CTG GCC ACA CGA AAC TGT TTA      2520
Ser Ser Leu Asn Phe Val His Arg Asp Leu Ala Thr Arg Asn Cys Leu
            705                 710                 715

GTG GGT AAG AAC TAC ACA ATC AAG ATA GCT GAC TTT GGA ATG AGC AGG      2568
Val Gly Lys Asn Tyr Thr Ile Lys Ile Ala Asp Phe Gly Met Ser Arg
            720                 725                 730

AAC CTG TAC AGT GGT GAC TAT TAC CGG ATC CAG GGC CGG GCA GTG CTC      2616
Asn Leu Tyr Ser Gly Asp Tyr Tyr Arg Ile Gln Gly Arg Ala Val Leu
            735                 740                 745

CCT ATC CGC TGG ATG TCT TGG GAG AGT ATC TTG CTG GGC AAG TTC ACT      2664
Pro Ile Arg Trp Met Ser Trp Glu Ser Ile Leu Leu Gly Lys Phe Thr
750                 755                 760                 765

ACA GCA AGT GAT GTG TGG GCC TTT GGG GTT ACT TTG TGG GAG ACT TTC      2712
Thr Ala Ser Asp Val Trp Ala Phe Gly Val Thr Leu Trp Glu Thr Phe
                770                 775                 780

ACC TTT TGT CAA GAA CAG CCC TAT TCC CAG CTG TCA GAT GAA CAG GTT      2760
Thr Phe Cys Gln Glu Gln Pro Tyr Ser Gln Leu Ser Asp Glu Gln Val
                785                 790                 795

ATT GAG AAT ACT GGA GAG TTC TTC CGA GAC CAA GGG AGG CAG ACT TAC      2808
Ile Glu Asn Thr Gly Glu Phe Phe Arg Asp Gln Gly Arg Gln Thr Tyr
                800                 805                 810

CTC CCT CAA CCA GCC ATT TGT CCT GAC TCT GTG TAT AAG CTG ATG CTC      2856
Leu Pro Gln Pro Ala Ile Cys Pro Asp Ser Val Tyr Lys Leu Met Leu
            815                 820                 825

AGC TGC TGG AGA AGA GAT ACG AAG AAC CGT CCC TCA TTC CAA GAA ATC      2904
Ser Cys Trp Arg Arg Asp Thr Lys Asn Arg Pro Ser Phe Gln Glu Ile
830                 835                 840                 845

CAC CTT CTG CTC CTT CAA CAA GGC GAC GAG TGATGCTGTC AGTGCCTGGC        2954
His Leu Leu Leu Leu Gln Gln Gly Asp Glu
                850                 855

CATGTTCCTA CGGCTCAGGT CCTCCCTACA AGACCTACCA CTCACCCATG CCTATGCCAC    3014

TCCATCTGGA CATTTAATGA AACTGAGAGA CAGAGGCTTG TTTGCTTTGC CCTCTTTTCC    3074

TGGTCACCCC CACTCCCTAC CCCTGACTCA TATATACTTT TTTTTTTTAC ATTAAAGAAC    3134

TAAAAAAAAA AAAAAAAAAG GCG                                           3157

(2) INFORMATION FOR SEQ ID NO: 4:

(i) SEQUENCE CHARACTERISTICS:
        (A) LENGTH: 855 amino acids
        (B) TYPE: amino acid
        (D) TOPOLOGY: unknown (ii) MOLECULE TYPE: protein (xi) SEQUENCE DESCRIPTION: SEQ ID NO: 4:

Met Ile Leu Ile Pro Arg Met Leu Leu Val Leu Phe Leu Leu Leu Pro
1               5                   10                  15

Ile Leu Ser Ser Ala Lys Ala Gln Val Asn Pro Ala Ile Cys Arg Tyr
            20                  25                  30

Pro Leu Gly Met Ser Gly Gly Gln Ile Pro Asp Glu Asp Ile Thr Ala
        35                  40                  45

Ser Ser Gln Trp Ser Glu Ser Thr Ala Ala Lys Tyr Gly Arg Leu Asp
    50                  55                  60

Ser Glu Glu Gly Asp Gly Ala Trp Cys Pro Ile Pro Val Glu Pro
65                  70                  75                  80

Asp Asp Leu Lys Glu Phe Leu Gln Ile Asp Leu His Thr Leu His Phe
                85                  90                  95
```

```
Ile Thr Leu Val Gly Thr Gln Gly Arg His Ala Gly His Gly Ile
            100                 105                 110

Glu Phe Ala Pro Met Tyr Lys Ile Asn Tyr Ser Arg Asp Gly Thr Arg
            115                 120                 125

Trp Ile Ser Trp Arg Asn Arg His Gly Lys Gln Val Leu Asp Gly Asn
130                 135                 140

Ser Asn Pro Tyr Asp Ile Phe Leu Lys Asp Leu Glu Pro Pro Ile Val
145                 150                 155                 160

Ala Arg Phe Val Arg Phe Ile Pro Val Thr Asp His Ser Met Asn Val
                165                 170                 175

Cys Met Arg Val Glu Leu Tyr Gly Cys Val Trp Leu Asp Gly Leu Val
                180                 185                 190

Ser Tyr Asn Ala Pro Ala Gly Gln Gln Phe Val Leu Pro Gly Gly Ser
                195                 200                 205

Ile Ile Tyr Leu Asn Asp Ser Val Tyr Asp Gly Ala Val Gly Tyr Ser
            210                 215                 220

Met Thr Glu Gly Leu Gly Gln Leu Thr Asp Gly Val Ser Gly Leu Asp
225                 230                 235                 240

Asp Phe Thr Gln Thr His Glu Tyr His Val Trp Pro Gly Tyr Asp Tyr
                245                 250                 255

Val Gly Trp Arg Asn Glu Ser Ala Thr Asn Gly Tyr Ile Glu Ile Met
                260                 265                 270

Phe Glu Phe Asp Arg Ile Arg Asn Phe Thr Thr Met Lys Val His Cys
                275                 280                 285

Asn Asn Met Phe Ala Lys Gly Val Lys Ile Phe Lys Glu Val Gln Cys
290                 295                 300

Tyr Phe Arg Ser Glu Ala Ser Glu Trp Glu Pro Asn Ala Ile Ser Phe
305                 310                 315                 320

Pro Leu Val Leu Asp Asp Val Asn Pro Ser Ala Arg Phe Val Thr Val
                325                 330                 335

Pro Leu His His Arg Met Ala Ser Ala Ile Lys Cys Gln Tyr His Phe
                340                 345                 350

Ala Asp Thr Trp Met Met Phe Ser Glu Ile Thr Phe Gln Ser Asp Ala
                355                 360                 365

Ala Met Tyr Asn Asn Ser Glu Ala Leu Pro Thr Ser Pro Met Ala Pro
                370                 375                 380

Thr Thr Tyr Asp Pro Met Leu Lys Val Asp Asp Ser Asn Thr Arg Ile
385                 390                 395                 400

Leu Ile Gly Cys Leu Val Ala Ile Ile Phe Ile Leu Leu Ala Ile Ile
                405                 410                 415

Val Ile Ile Leu Trp Arg Gln Phe Trp Gln Lys Met Leu Glu Lys Ala
                420                 425                 430

Ser Arg Arg Met Leu Asp Asp Glu Met Thr Val Ser Leu Ser Leu Pro
                435                 440                 445

Ser Asp Ser Ser Met Phe Asn Asn Asn Arg Ser Ser Ser Pro Ser Glu
                450                 455                 460

Gln Gly Ser Asn Ser Thr Tyr Asp Arg Ile Phe Pro Leu Arg Pro Asp
465                 470                 475                 480

Tyr Gln Glu Pro Ser Arg Leu Ile Arg Lys Leu Pro Glu Phe Ala Pro
                485                 490                 495

Gly Glu Glu Glu Ser Gly Cys Ser Gly Val Val Lys Pro Val Gln Pro
                500                 505                 510

Ser Gly Pro Glu Gly Val Pro His Tyr Ala Glu Ala Asp Ile Val Asn
```

```
                515                 520                 525
Leu Gln Gly Val Thr Gly Asn Thr Tyr Ser Val Pro Ala Val Thr
    530                 535                 540
Met Asp Leu Leu Ser Gly Lys Asp Val Ala Val Glu Glu Phe Pro Arg
545                 550                 555                 560
Lys Leu Leu Thr Phe Lys Glu Lys Leu Gly Glu Gly Gln Phe Gly Glu
                565                 570                 575
Val His Leu Cys Glu Val Glu Gly Met Glu Lys Phe Lys Asp Lys Asp
                580                 585                 590
Phe Ala Leu Asp Val Ser Ala Asn Gln Pro Val Leu Val Ala Val Lys
                595                 600                 605
Met Leu Arg Ala Asp Ala Asn Lys Asn Ala Arg Asn Asp Phe Leu Lys
                610                 615                 620
Glu Ile Lys Ile Met Ser Arg Leu Lys Asp Pro Asn Ile Ile His Leu
625                 630                 635                 640
Leu Ser Val Cys Ile Thr Asp Asp Pro Leu Cys Met Ile Thr Glu Tyr
                645                 650                 655
Met Glu Asn Gly Asp Leu Asn Gln Phe Leu Ser Arg His Glu Pro Pro
                660                 665                 670
Asn Ser Ser Ser Ser Asp Val Arg Thr Val Ser Tyr Thr Asn Leu Lys
                675                 680                 685
Phe Met Ala Thr Gln Ile Ala Ser Gly Met Lys Tyr Leu Ser Ser Leu
                690                 695                 700
Asn Phe Val His Arg Asp Leu Ala Thr Arg Asn Cys Leu Val Gly Lys
705                 710                 715                 720
Asn Tyr Thr Ile Lys Ile Ala Asp Phe Gly Met Ser Arg Asn Leu Tyr
                725                 730                 735
Ser Gly Asp Tyr Tyr Arg Ile Gln Gly Arg Ala Val Leu Pro Ile Arg
                740                 745                 750
Trp Met Ser Trp Glu Ser Ile Leu Leu Gly Lys Phe Thr Thr Ala Ser
                755                 760                 765
Asp Val Trp Ala Phe Gly Val Thr Leu Trp Glu Thr Phe Thr Phe Cys
770                 775                 780
Gln Glu Gln Pro Tyr Ser Gln Leu Ser Asp Glu Gln Val Ile Glu Asn
785                 790                 795                 800
Thr Gly Glu Phe Phe Arg Asp Gln Gly Arg Gln Thr Tyr Leu Pro Gln
                805                 810                 815
Pro Ala Ile Cys Pro Asp Ser Val Tyr Lys Leu Met Leu Ser Cys Trp
                820                 825                 830
Arg Arg Asp Thr Lys Asn Arg Pro Ser Phe Gln Glu Ile His Leu Leu
                835                 840                 845
Leu Leu Gln Gln Gly Asp Glu
850                 855

(2) INFORMATION FOR SEQ ID NO: 5:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 3
        (D) OTHER INFORMATION: /note= "Ala can be enchanged for
``` any amino acid"

(xi) SEQUENCE DESCRIPTION: SEQ ID NO: 5:

Asn Pro Ala Tyr
1

(2) INFORMATION FOR SEQ ID NO: 6:

(i) SEQUENCE CHARACTERISTICS:
                (A) LENGTH: 10 amino acids
                (B) TYPE: amino acid
                (D) TOPOLOGY: unknown (ii) MOLECULE TYPE: peptide (xi) SEQUENCE DESCRIPTION: SEQ ID NO: 6:

Thr Tyr Ala Xaa Pro Xaa Xaa Xaa Pro Gly
1               5                   10

(2) INFORMATION FOR SEQ ID NO: 7:

(i) SEQUENCE CHARACTERISTICS:
                (A) LENGTH: 6 amino acids
                (B) TYPE: amino acid
                (D) TOPOLOGY: unknown (ii) MOLECULE TYPE: peptide (xi) SEQUENCE DESCRIPTION: SEQ ID NO: 7:

His Arg Asp Leu Ala Ala
1               5

(2) INFORMATION FOR SEQ ID NO: 8:

(i) SEQUENCE CHARACTERISTICS:
                (A) LENGTH: 28 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 8:

GGAATTCCCA YMGNRAYYTN RCNRCNMG                                                      28

(2) INFORMATION FOR SEQ ID NO: 9:

(i) SEQUENCE CHARACTERISTICS:
                (A) LENGTH: 6 amino acids
                (B) TYPE: amino acid
                (D) TOPOLOGY: unknown (ii) MOLECULE TYPE: peptide (ix) FEATURE:
                (A) NAME/KEY: Modified-site
                (B) LOCATION: 6
                (D) OTHER INFORMATION: /note= "Xaa can be either Phe or
                    Tyr"

(xi) SEQUENCE DESCRIPTION: SEQ ID NO: 9:

Ser Asp Val Trp Ser Xaa
1               5

(2) INFORMATION FOR SEQ ID NO: 10:

(i) SEQUENCE CHARACTERISTICS:
                (A) LENGTH: 26 base pairs
                (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO: 10:

GGAATTCCYW YNSWGGTNTG SAGNST                                          26

(2) INFORMATION FOR SEQ ID NO: 11:

(i) SEQUENCE CHARACTERISTICS:
        (A) LENGTH: 19 amino acids
        (B) TYPE: amino acid
        (D) TOPOLOGY: unknown (ii) MOLECULE TYPE: peptide (xi) SEQUENCE DESCRIPTION: SEQ ID NO: 11:

His Phe Asp Pro Ala Lys Asp Cys Arg Tyr Ala Leu Gly Met Gln Asp
1               5                   10                  15
Arg Thr Ile (2) INFORMATION FOR SEQ ID NO: 12:

(i) SEQUENCE CHARACTERISTICS:
        (A) LENGTH: 19 amino acids
        (B) TYPE: amino acid
        (D) TOPOLOGY: unknown (ii) MOLECULE TYPE: peptide (xi) SEQUENCE DESCRIPTION: SEQ ID NO: 12:

Arg Pro Pro Phe Ser Gln Leu His Arg Phe Leu Ala Glu Asp Ala Leu
1               5                   10                  15
Asn Thr Val (2) INFORMATION FOR SEQ ID NO: 13:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO: 13:

Pro Ala Met Ala Trp Glu Gly Glu Pro Met Arg His Asn Leu
1               5                   10

(2) INFORMATION FOR SEQ ID NO: 14:

(i) SEQUENCE CHARACTERISTICS:
        (A) LENGTH: 17 amino acids
        (B) TYPE: amino acid
        (D) TOPOLOGY: unknown (ii) MOLECULE TYPE: peptide (xi) SEQUENCE DESCRIPTION: SEQ ID NO: 14:

Cys Trp Ser Arg Glu Ser Glu Gln Arg Pro Pro Phe Ser Gln Leu His
1               5                   10                  15
Arg
```

US 6,897,029 B1

MCK-10 A NOVEL RECEPTOR TYROSINE KINASE

This is a division of application Ser. No. 08/153,397, filed Nov. 16 1993 now U.S. Pat. No. 6,051,397, the entire contents of which is incorporated herein by reference in its entirety.

1. INTRODUCTION

The present invention relates to the novel family of receptor tyrosine kinases, herein referred to as MCK-10, to nucleotide sequences and expression vectors encoding MCK-10, and to methods of inhibiting MCK-10 activity. The invention relates to differentially spliced isoforms of MCK-10 and to other members of the MCK-10 receptor tyrosine kinase family. Genetically engineered host cells that express MCK-10 may be used to evaluate and screen drugs involved in MCK-10 activation and regulation. The invention relates to the use of such drugs, in the treatment of disorders, including cancer, by modulating the activity of MCK-10.

2. BACKGROUND

Receptor tyrosine kinases comprise a large family of transmembrane receptors which are comprised of an extracellular ligand-binding domain and an intracellular tyrosine-kinase domain responsible for mediating receptor activity. The receptor tyrosine kinases are involved in a variety of normal cellular responses which include proliferation, alterations in gene expression, and changes in cell shape.

The binding of ligand to its cognate receptor induces the formation of receptor dimers leading to activation of receptor kinase activity. The activation of kinase activity results in phosphorylation of multiple cellular substrates involved in the cascade of events leading to cellular responses such as cell proliferation.

Genetic alterations in growth factor mediated signalling pathways have been linked to a number of different diseases, including human cancer. For example, the normal homologs of many oncogenes have been found to encode growth factors or growth factor receptors. This is illustrated by the discovery that the B chain of human PDGF is homologous to the transforming protein of simian sarcoma virus (SSV), the EGF (epidermal growth factor) receptor to erb B; the CSF (colony stimulating factor) receptor to fms; and the NGF (nerve growth factor) receptor to trk. In addition, growth factor receptors are often found amplified and/or overexpressed in cancer cells as exemplified by the observation that the EGF receptor is often found amplified or overexpressed in squamous cell carcinomas and glioblastomas. Similarly, If amplification and overexpression of the met gene, encoding the HGF receptor, has been detected in stomach carcinomas.

Recently, a number of cDNAs have been identified that encode receptor tyrosine kinases. One such clone, referred to as DDR (discoidin domain receptor), was isolated from a breast carcinoma cDNA library (Johnson et al., 1993, Proc. Natl. Acad. Sci. USA, 90, 5677–57681) and is homologous to MCK-10. In addition, a mouse homologue of MCK-10 has recently been cloned and characterized (Yerlin, M. et al., 1993, Oncongene, 8:2731–2739).

The discovery of novel receptor tyrosine kinase receptors, whose expression is associated with proliferative diseases such as cancer, will provide opportunities for development of novel diagnostic reagents. In addition, the identification of aberrantly expressed receptor tyrosine kinases will lead to the development of therapeutic applications designed to inhibit the activity of that receptor, which may be useful for treatment of proliferative diseases such as cancer.

3. SUMMARY OF THE INVENTION

The present invention relates to a novel family of receptor tyrosine kinases, herein referred to as MCK-10 (mammary carcinoma kinase 10), to nucleotide sequences and expression vectors encoding MCK-10, and to methods of inhibiting MCK-10 activity. The invention is based on the isolation of cDNA clones from a human mammary carcinoma cDNA library encoding the MCK-10 receptor tyrosine kinase.

The invention also relates to differentially spliced isoforms of MCK-10 and to other members of the MCK-10 family of receptor tyrosine kinases. More specifically, the invention relates to members of the MCK-10 family of receptors tyrosine kinases that are defined, herein, as those receptors demonstrating 80% homology at the amino acid level in substantial stretches of DNA sequences with MCK-10. In addition, members of the MCK-10 family of tyrosine kinase receptors are defined as those receptors containing an intracellular tyrosine kinase domain and consensus sequences near the extracellular N-terminus of the protein for the discoidin I like family of proteins. The invention as it relates to the members of the MCK-10 family of receptor tyrosine kinases, is based on the isolation and characterization of a cDNA, herein referred to as CCK-2, encoding a member of the MCK-10 family of receptor tyrosine kinases.

Northern blot analysis and in situ hybridization indicates that MCK-10 is expressed in a wide variety of cancer cell lines and tumor tissue. The MCK-10 or CCK-2 coding sequence may be used for diagnostic purposes for detection of aberrant expression of these genes. For example the MCK-10 or CCK-2 DNA sequence may be used in hybridization assays of biopsied tissue to diagnose abnormalities in gene expression.

The present invention also relates to inhibitors of MCK-10 or CCK-2 receptor activity which may have therapeutic value in the treatment of proliferative diseases such as cancer. Such inhibitors include antibodies to epitopes of recombinantly expressed S MCK-10 or CCK-2 receptor that neutralize the activity of the receptor. In another embodiment of the invention, MCK-10 or CCK-2 anti-sense oligonucleotides may be designed to inhibit synthesis of the encoded proteins through inhibition of translation. In addition, random peptide libraries may be screened using recombinantly produced MCK-10 or CCK-2 protein to identify peptides that inhibit the biological activity of the receptor through binding to the ligand binding sites or other functional domains of the MCK-10 or CCK-2 receptor. In a further embodiment of the invention, mutated forms of MCK-10 and CCK-2, having a dominant negative effect, may be expressed in targeted cell populations to inhibit the activity of the endogenously expressed receptors.

4. BRIEF DESCRIPTION OF THE FIGURES

FIGS. 1A–1G. Human MCK-10 nucleotide sequence and deduced amino acid sequence. Regions of interest include the signal sequence (amino acids (aa) 1–18); the Discoidin I-like domain (aa 31–185); the putative precursor cleavage sit (aa 304–307); the transmembrane region (aa 417–439); the alternatively spliced sequence I (aa 505–541); the alternatively spliced sequence II (aa 666–671); and the peptide antibody recognition sequences: NTα:aa 25–42, NTβ:aa 309–321, CTβ:aa 902–919.

FIG. 2. MCK-10 splice variant.

FIGS. 3A–3H. Human CCK-2 nucleotide sequence and deduced amino acid sequence.

FIGS. 4A and 4B. Shared sequence homology between MCK-10 and CCK-2.

Figure 4C:
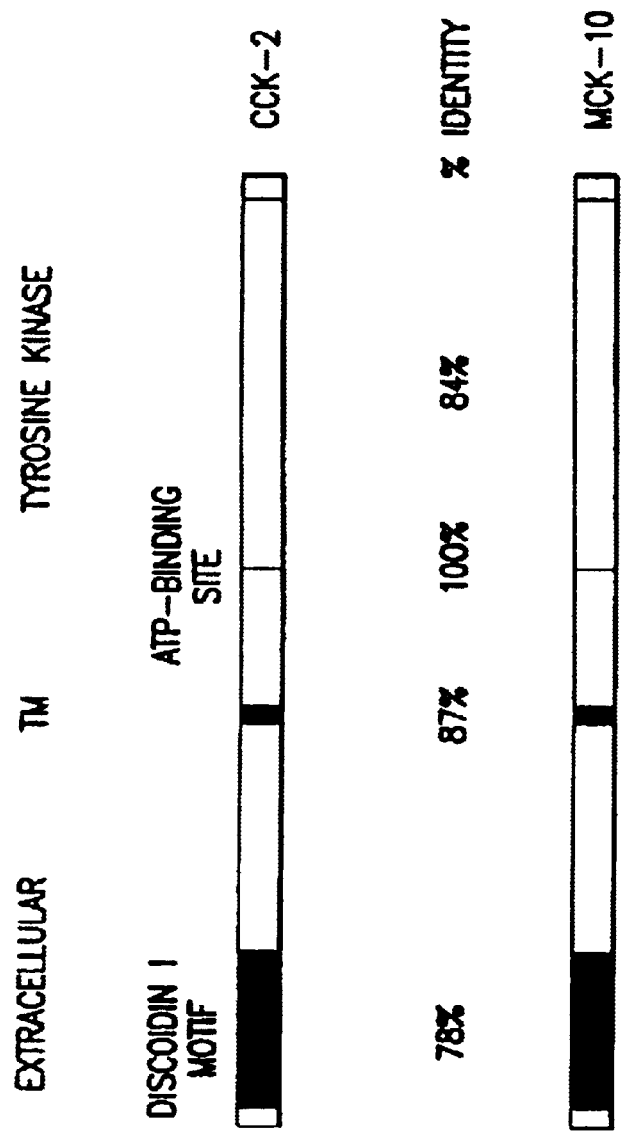

FIG. 4C. Shared regions of homology between MCK-10 and CCK-2.

FIG. 5A. Northern blot analysis of MCK-10 mRNA in different human tissues. Three micrograms of poly $(A)^+$ RNA are loaded per lane. The blot is hybridized with a cDNA restriction fragment corresponding to nucleotide 278 to 1983 of MCK-10 (FIGS. 1A, 1B and 1C) (excluding the 111 bp insertion). As a control, the blot was rehybridized with a glyceraldehyde phosphate dehydrogenase (GAPDH) cDNA probe (lower panel).

Figure 5B:
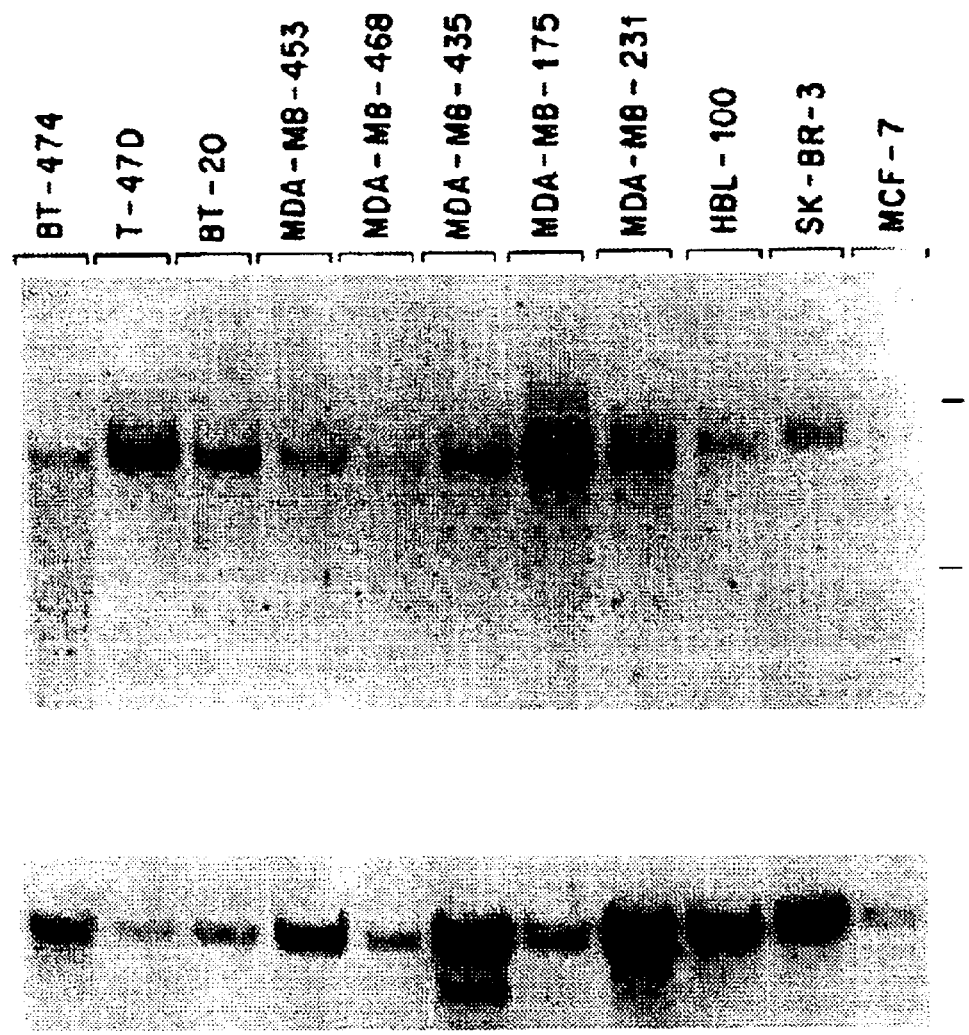

FIG. 5B. Northern blot analysis of MCK-10 gene in various human breast cancer cell lines. Samples containing three micrograms of poly $(A)^+$ RNA isolated from different human breast cancer cell lines were analyzed. The position of 28S and 18S ribosomal RNAs is indicated, the lower panel shows the rehybridization with a GAPDH cDNA probe.

FIG. 5C. Northern blot analysis of MCK-10 mRNA in different human tissues and cell lines of tumor origin. Size markers are indicating 28S and 18S ribosomal RNAs (upper panel). Rehybridization is performed with a GAPDH cDNA probe (lower panel).

Figure 6A:
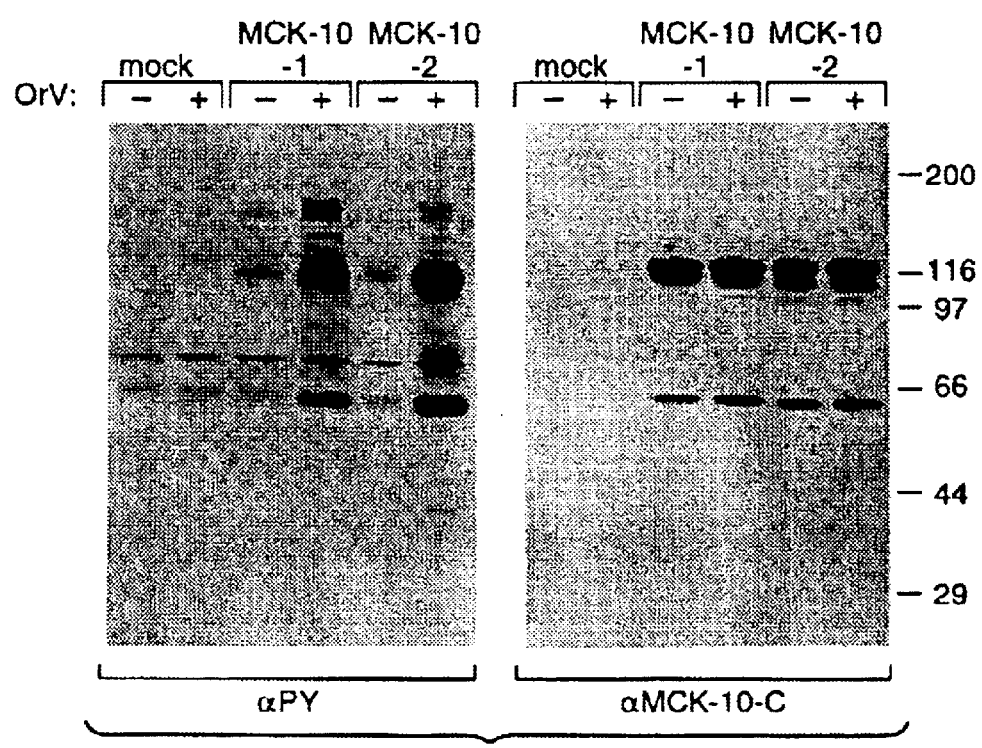

FIG. 6A. Tyrosine phosphorylation of overexpressed MCK-10. The coding cDNAs of MCK-10-1 and MCK-10-2 were cloned into an expression vector and transiently overexpressed in the 293 cell line (human embryonic kidney fibroblasts, ATCC CRL 1573). Portions of cell lysate from either MCK-10-1 or -2 transfected cells or control plasmid transfected cells (mock) were separated on a 7–12% gradient polyacrylamide gel and transferred to nitrocellulose and probed with anti-phosphotyrosine antibodies (αPY). The incubation of cells with 1 mM sodium ortho-vanadate 90 min. prior to lysis is indicated by –/+; (left panel). After removal of the αPY antibody the blot was reprobed with an affinity purified polyclonal antiserum raised against the C-terminal octapeptide of MCK-10 (α MCK-10-C); (right panel). Molecular size markers are indicated in kD.

Figure 6B:
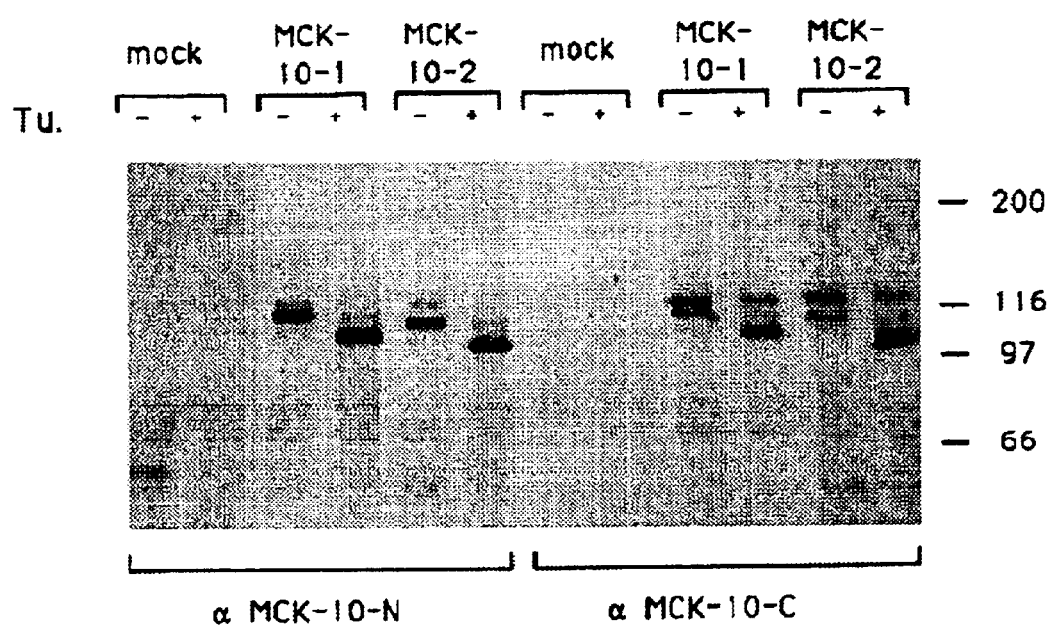

FIG. 6B. Distinct glycosylation of overexpressed MCK-10 splice variants. 293 cells were transfected with MCK-10-1 and -2 as before, metabolically labeled with [$^{35}$S]-L-methionine and treated with 10 $\mu$/ml tunicamycin overnight as indicated (+), lysed and immunoprecipitated with antisera generated against the N-terminal and C-terminal peptides of MCK-10 (a MCK-10-N and a MCK-10-C). The autoradiograph of the SDS-PAGE analysis is shown. Molecular size markers are indicated in kD.

Figure 7A:
Figure 7B:
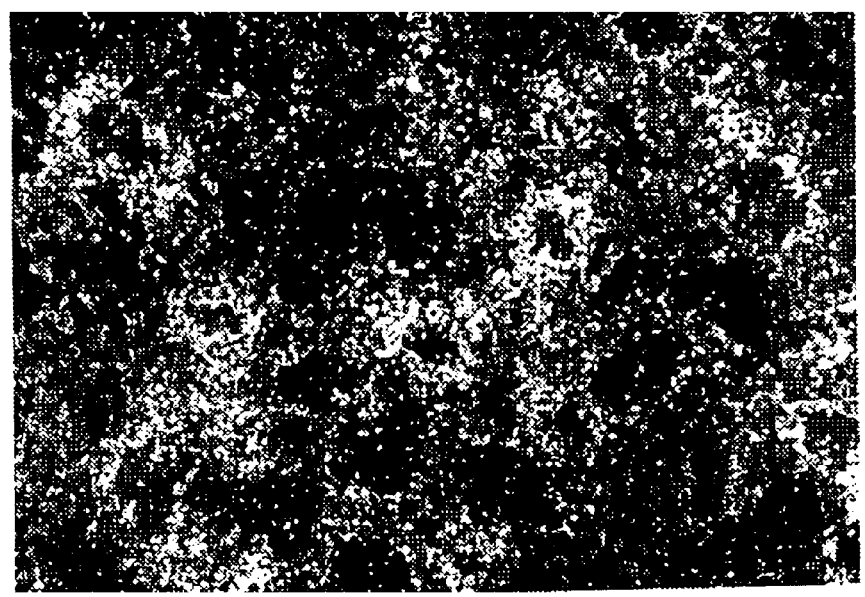

FIG. 7. In situ hybridization showing specific expression of MCK-10 in epithelial cells of the distal tubuli of the kidney.

Figure 8A:
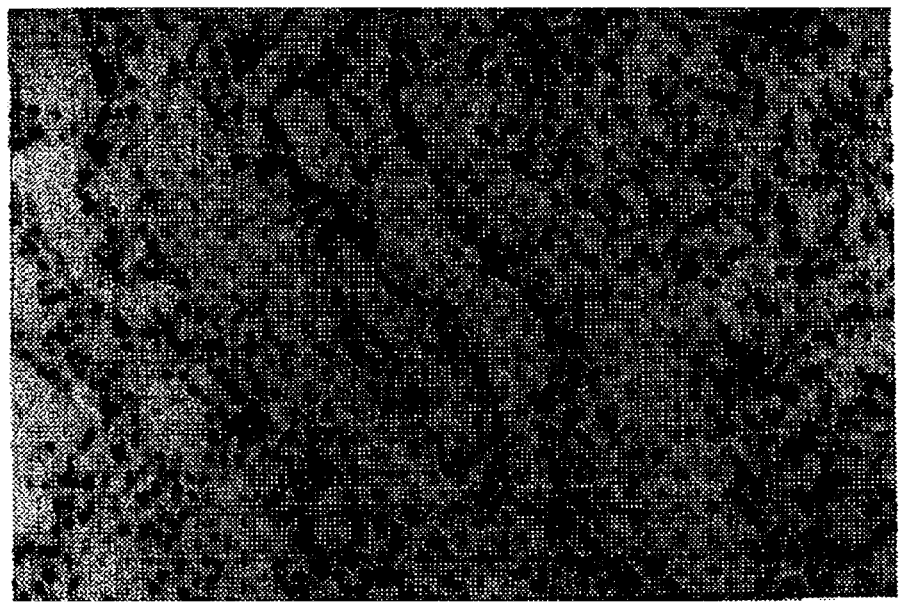
Figure 8B:
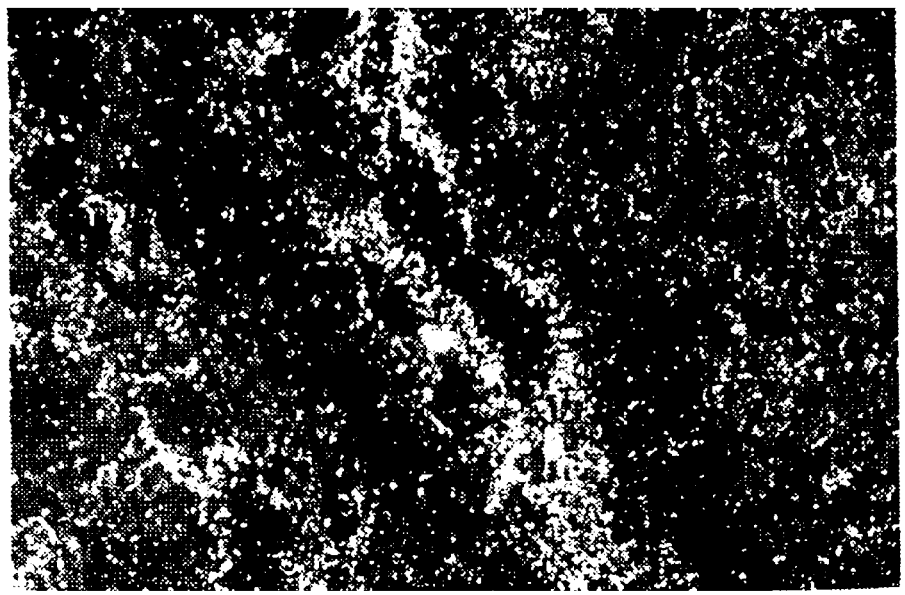

FIG. 8. In situ hybridization showing expression of MCK-10 only in epithelial cells of the distal tubular cells of the kidney.

Figure 9A:
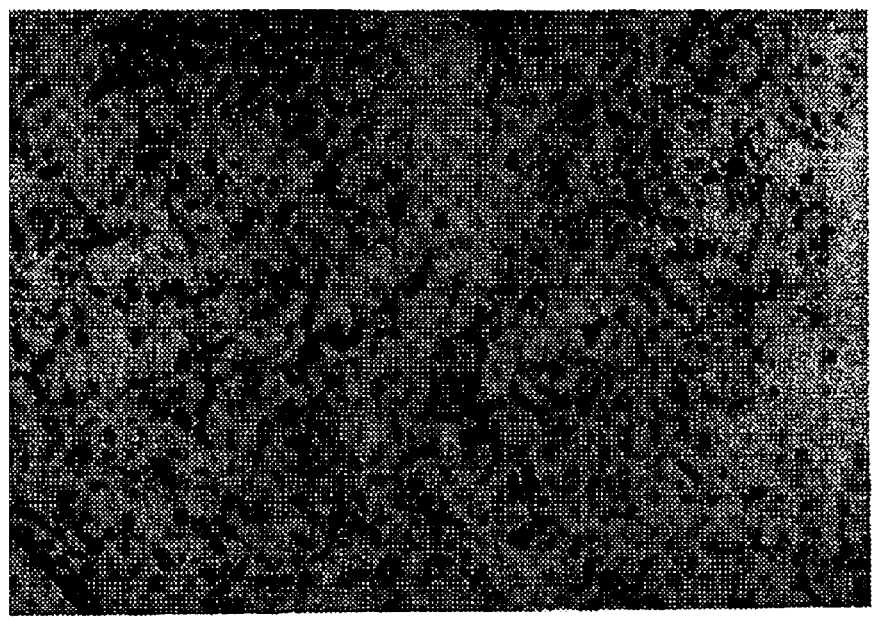
Figure 9B:
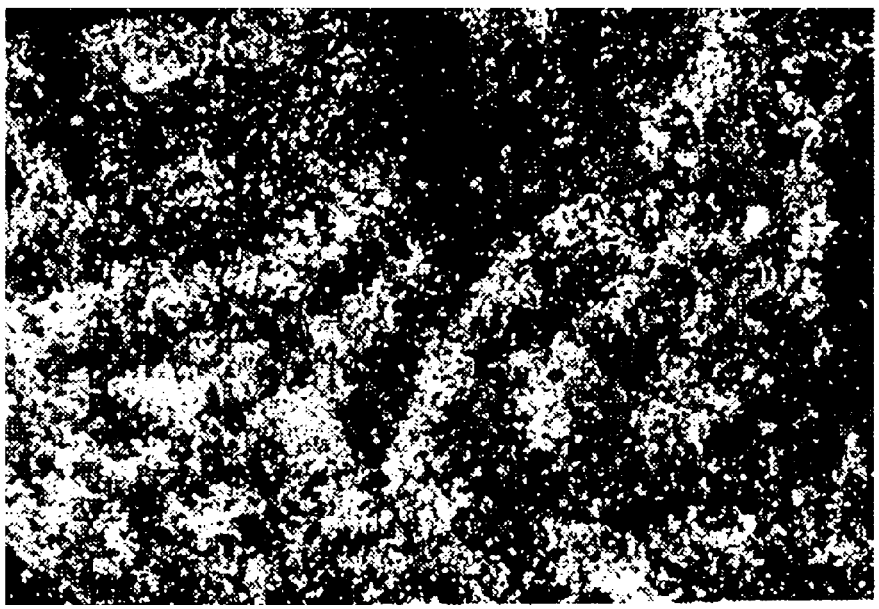

FIG. 9. In situ hybridization showing specific expression of MCK-10 in tumor cells of a renal cell carcinoma.

Figure 10A:
Figure 10B:
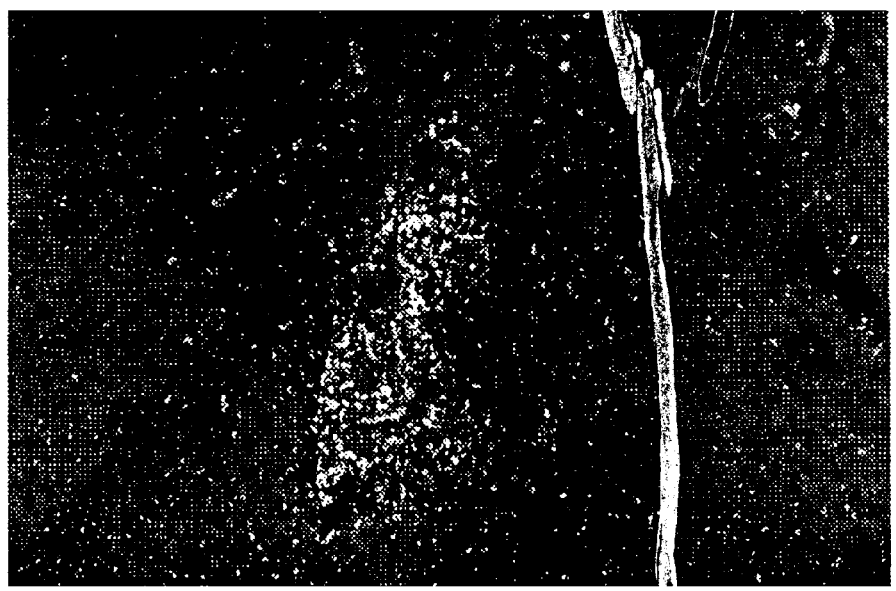

FIG. 10. In situ hybridization of MCK-10 in the ductal epithelial cells of normal breast tissue.

Figure 11A:
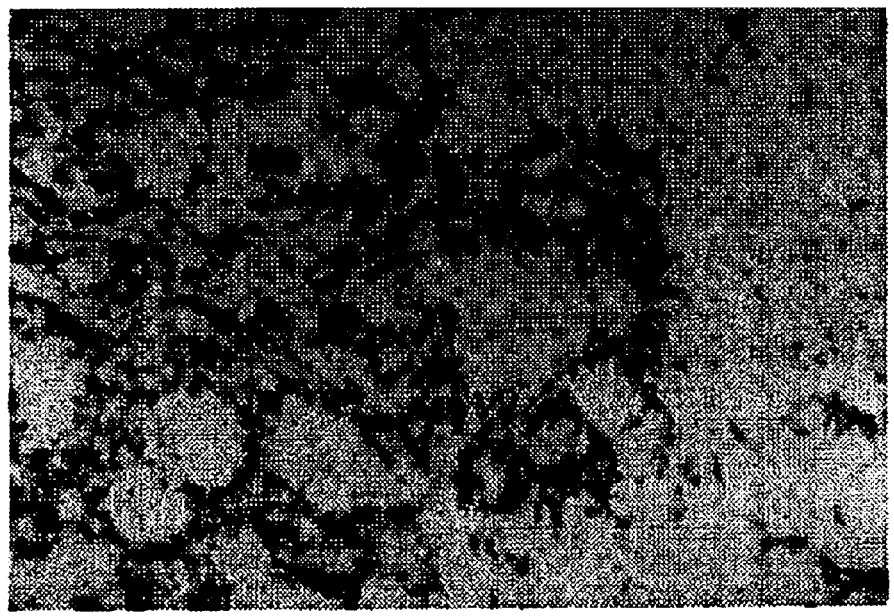
Figure 11B:
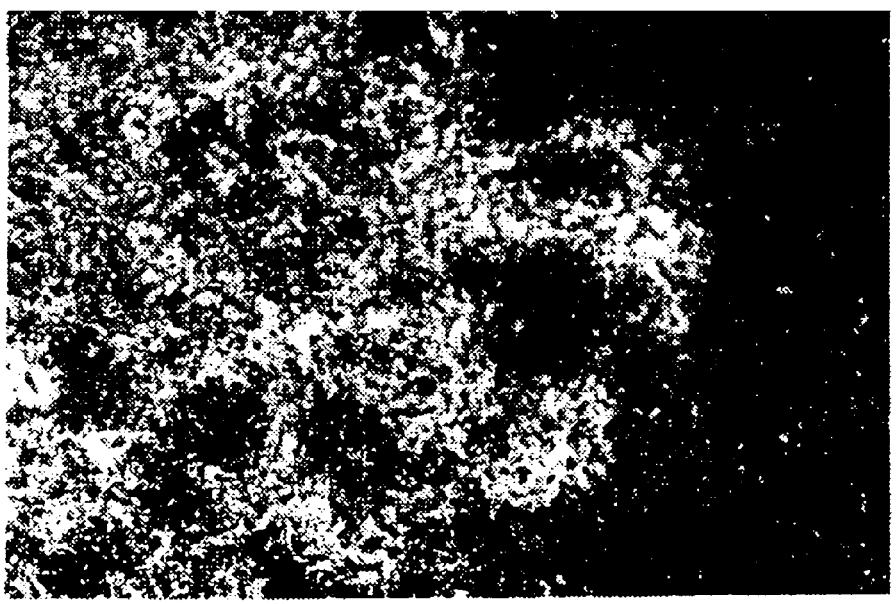

FIG. 11. In situ hybridization showing MCK-10 expression in infiltrating tumor cells of a breast carcinoma. The tumor infiltrates the surrounding fat tissue, which is negative for MCK-10 expression.

Figure 12A:
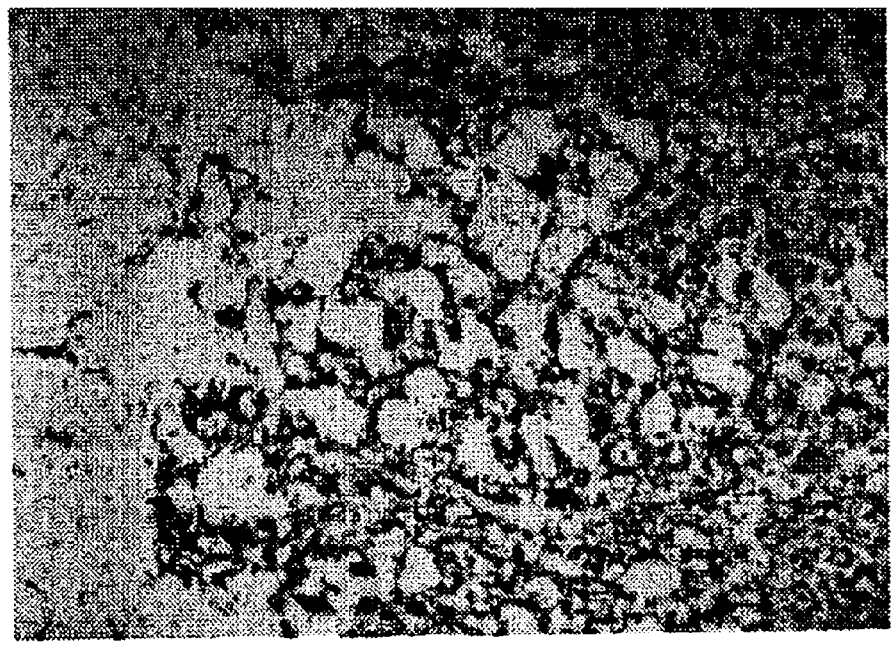
Figure 12B:
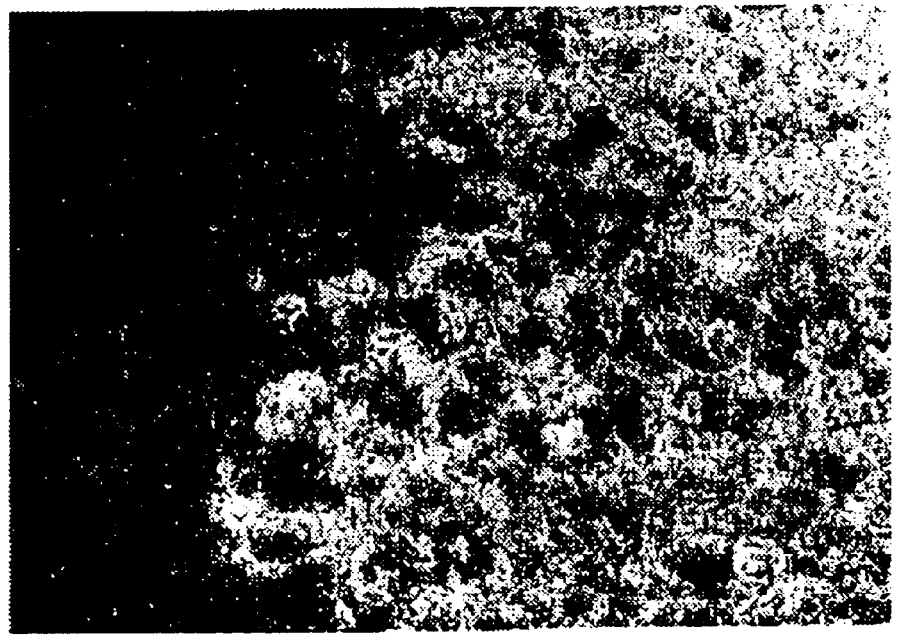

FIG. 12. In situ hybridization showing MCK-10 expression in infiltrating tumor cells of a breast carcinoma. The tumor infiltrates the surrounding fat issue, which is negative for MCK-10 expression.

Figure 13A:
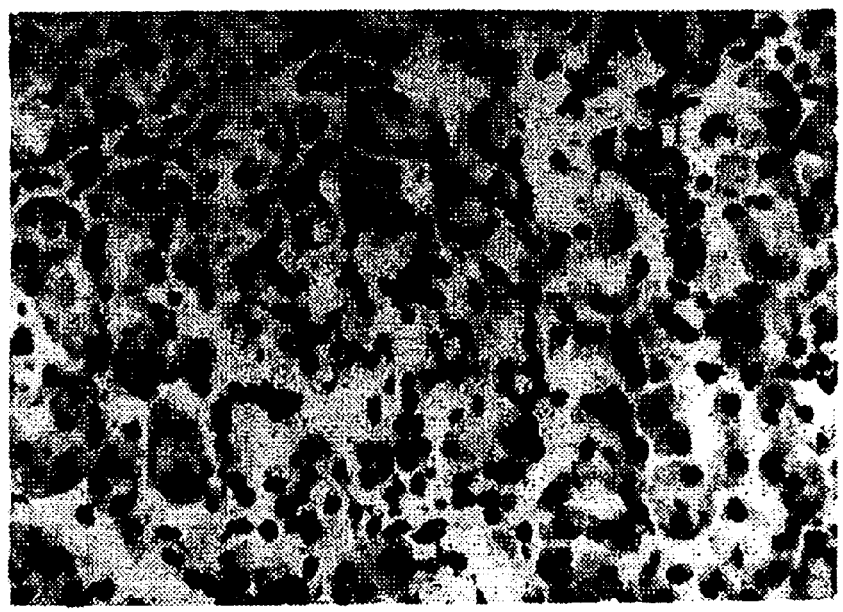
Figure 13B:
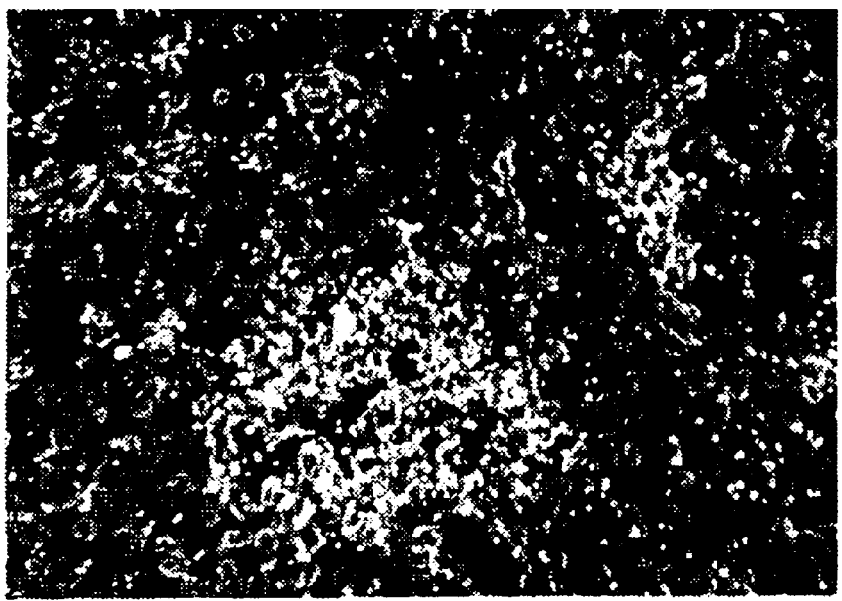

FIG. 13. In situ hybridization showing expression of MCK-10 expression in the islet cells of the pancreas.

Figure 14A:
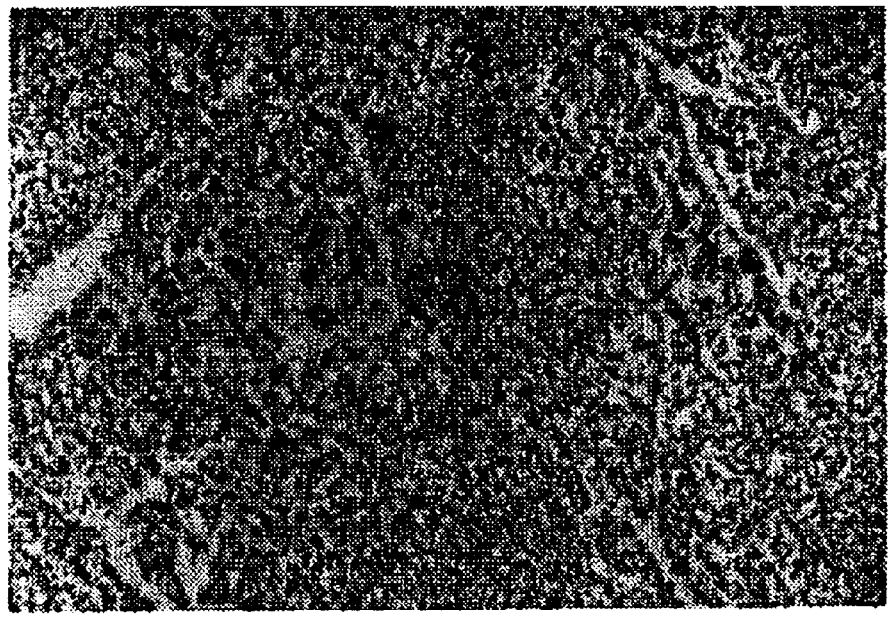
Figure 14B:
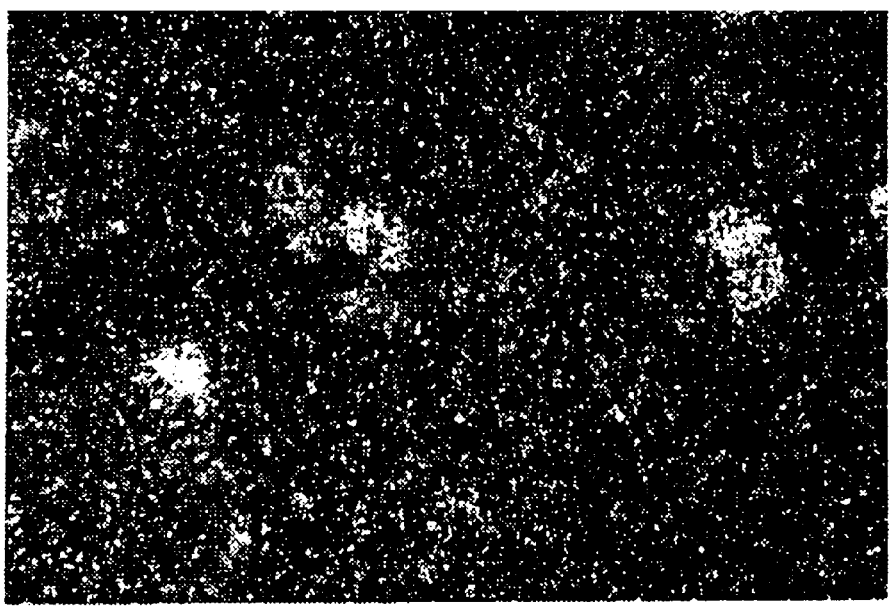

FIG. 14. In situ hybridization showing expression of MCK-10 expression in the islet cells of the pancreas.

Figure 15A:
Figure 15B:
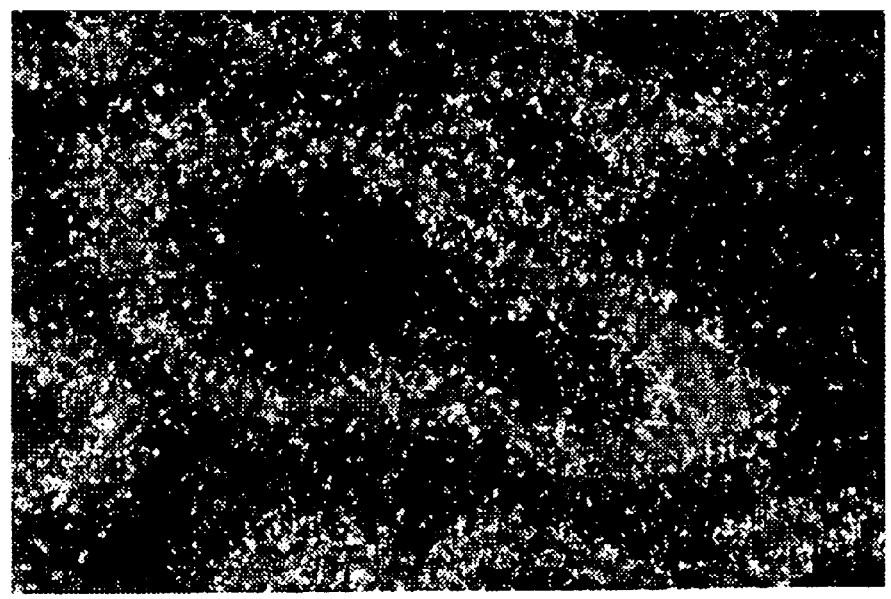

FIG. 15. In situ hybridization showing selective expression of MCK-10 in the surface epithelium of the colon in contrast to connective tissue.

Figure 16A:
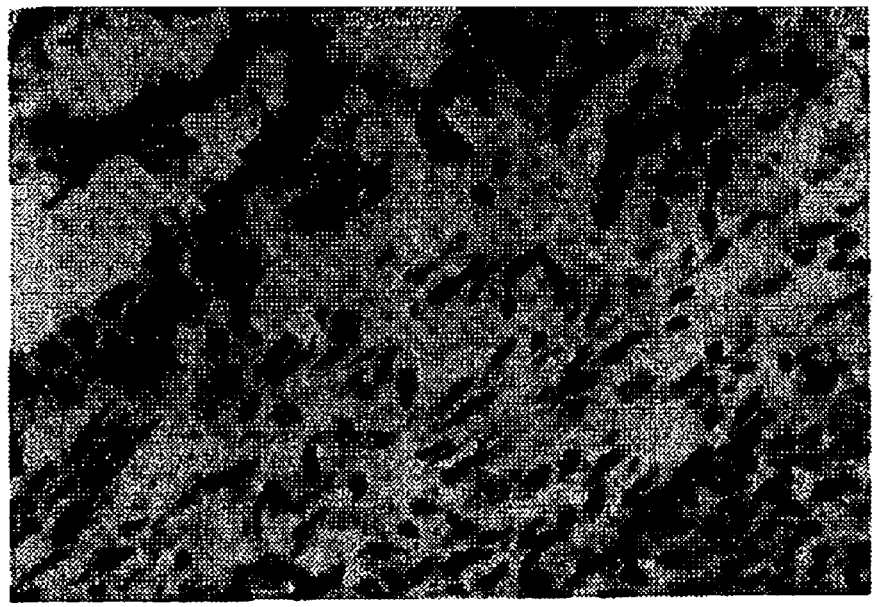
Figure 16B:
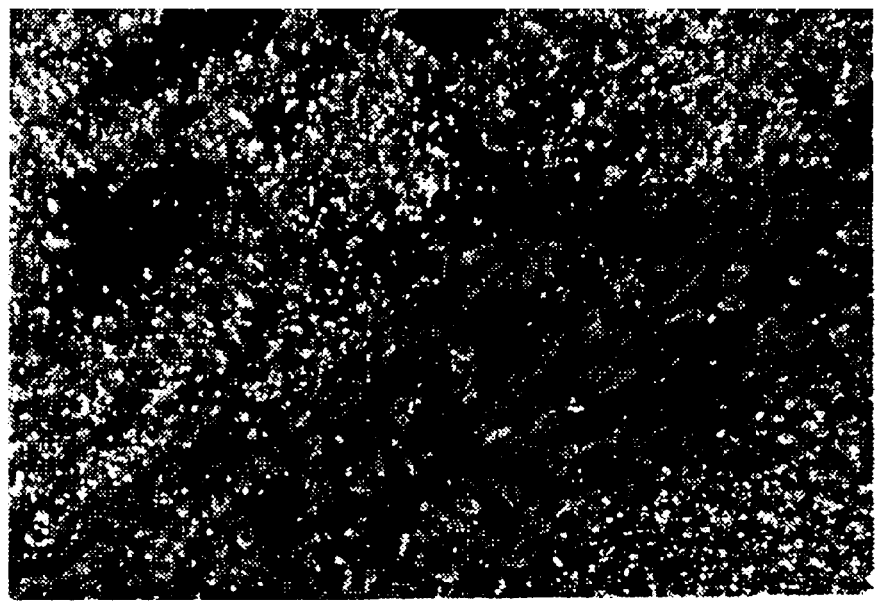

FIG. 16. In situ hybridization showing expression of MCK-10 in the tumor cells of an adenocarcinoma of the colon.

Figure 17A:
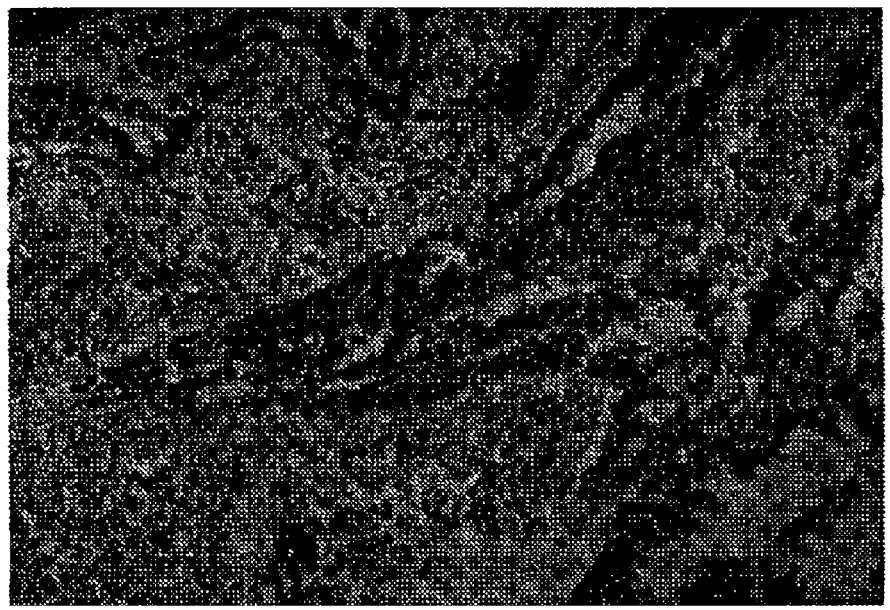
Figure 17B:
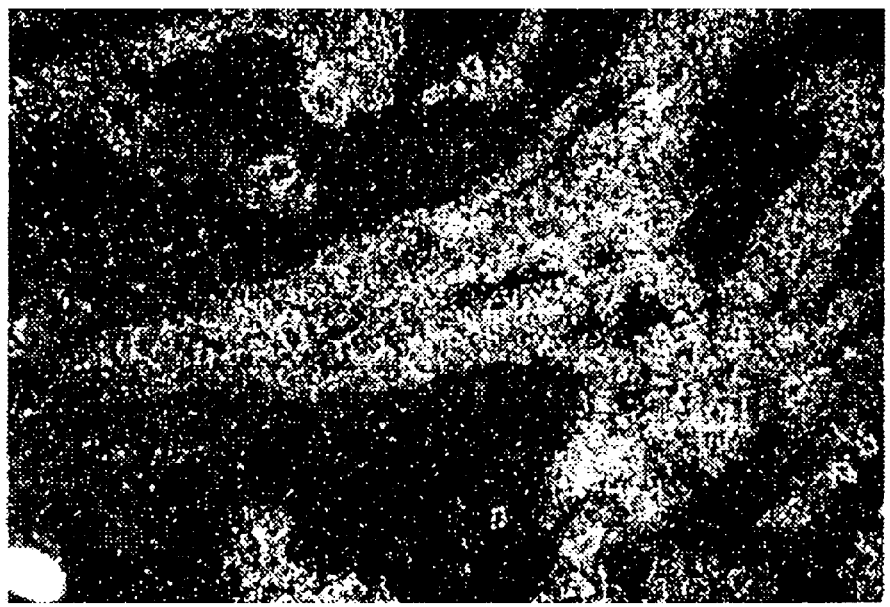

FIG. 17. In situ hybridization showing expression of MCK-10 in the tumor cells of an adenocarcinoma of the colon.

Figure 18A:
Figure 18B:
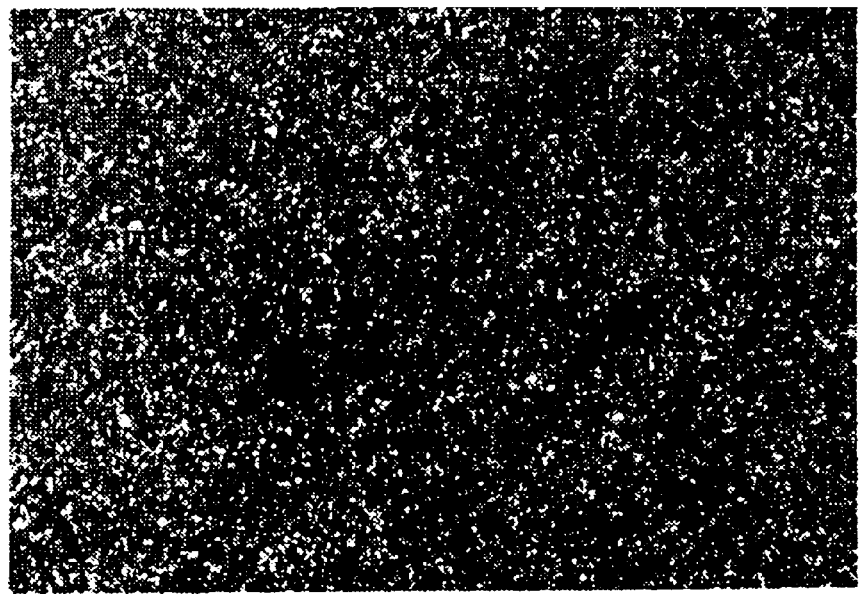

FIG. 18. In situ hybridization showing expression of MCK-10 in meningiothelial tumor cells.

Figure 19A:
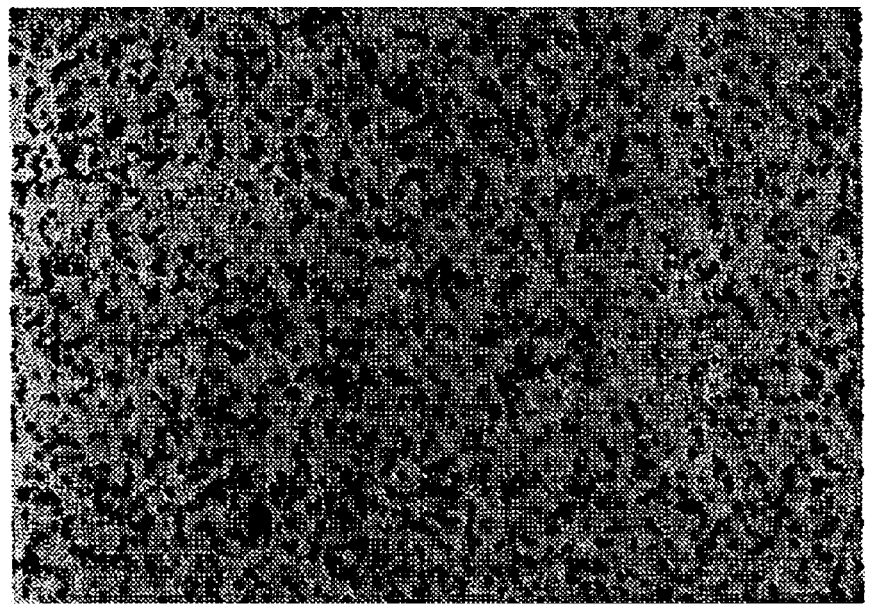
Figure 19B:
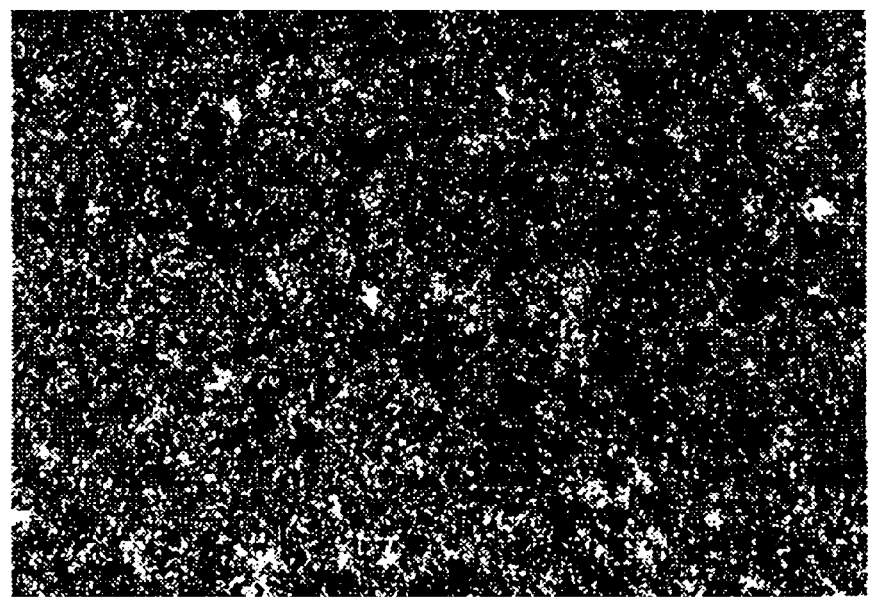

FIG. 19. In situ hybridization showing expression of MCK-10 in cells of a glioblastoma (glioma), a tumor of the neuroepithelial tissue.

Figure 20A:
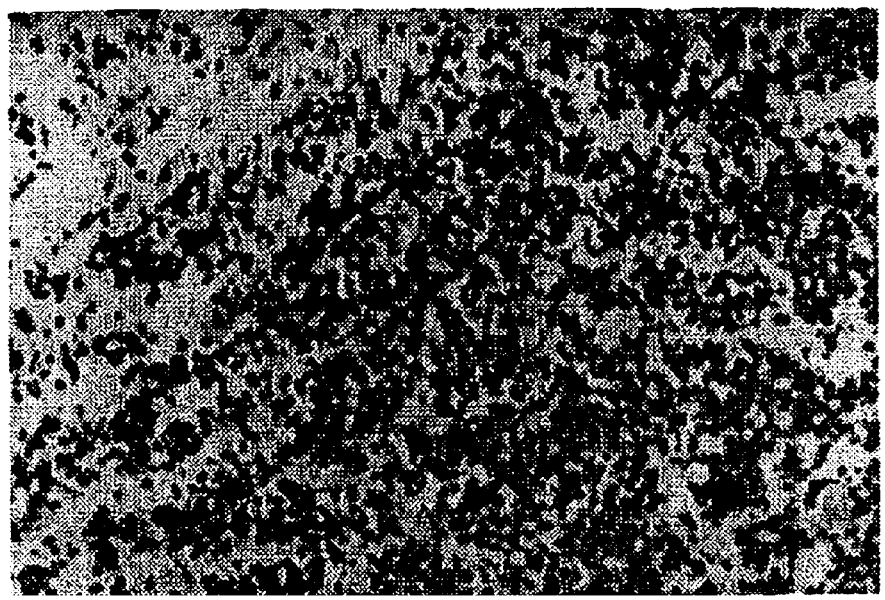
Figure 20B:
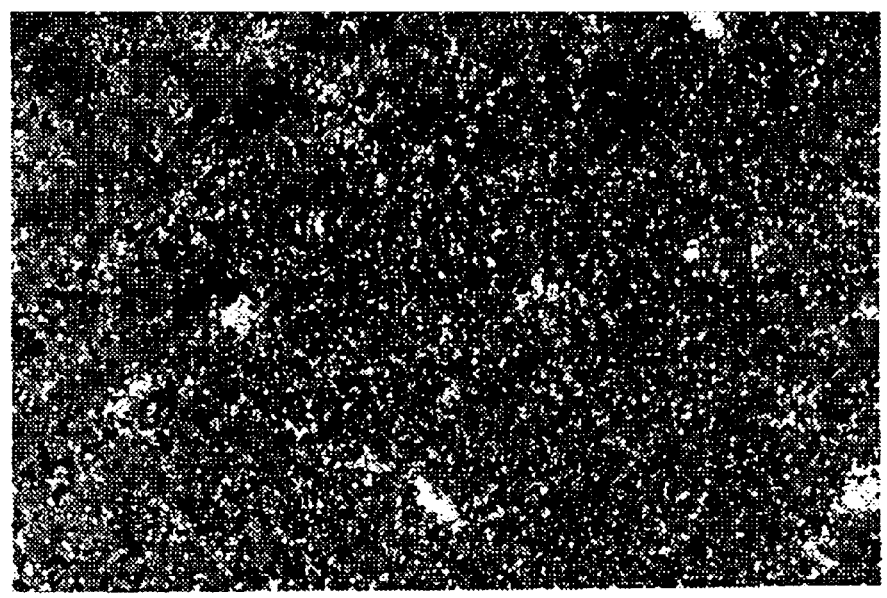

FIG. 20. In situ hybridization showing expression of MCK-10 in cells of a medulloblastoma with hyperchromatic atypical nuclei. Expression of MCK-10 is predominantly in cells with well developed cytoplasm.

Figure 21A:
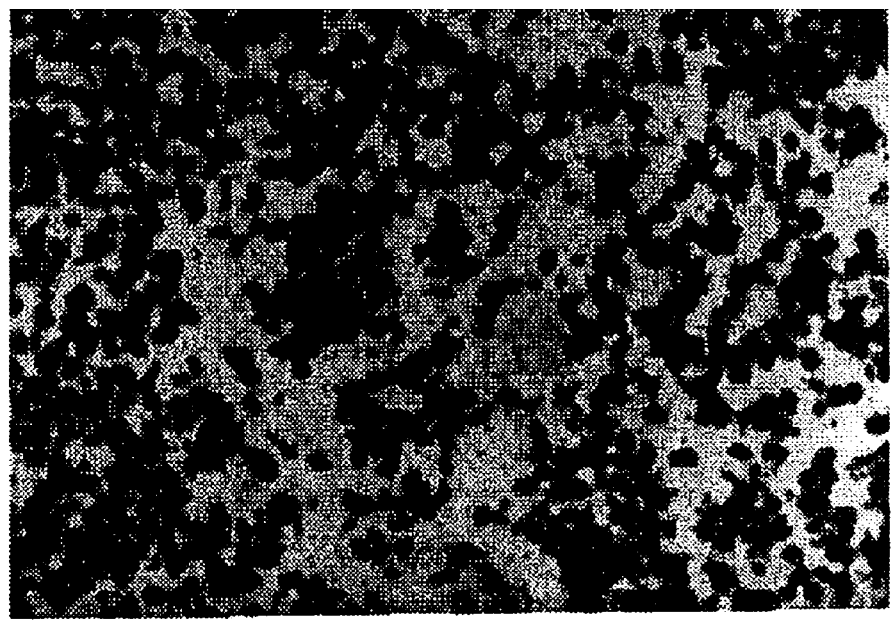
Figure 21B:
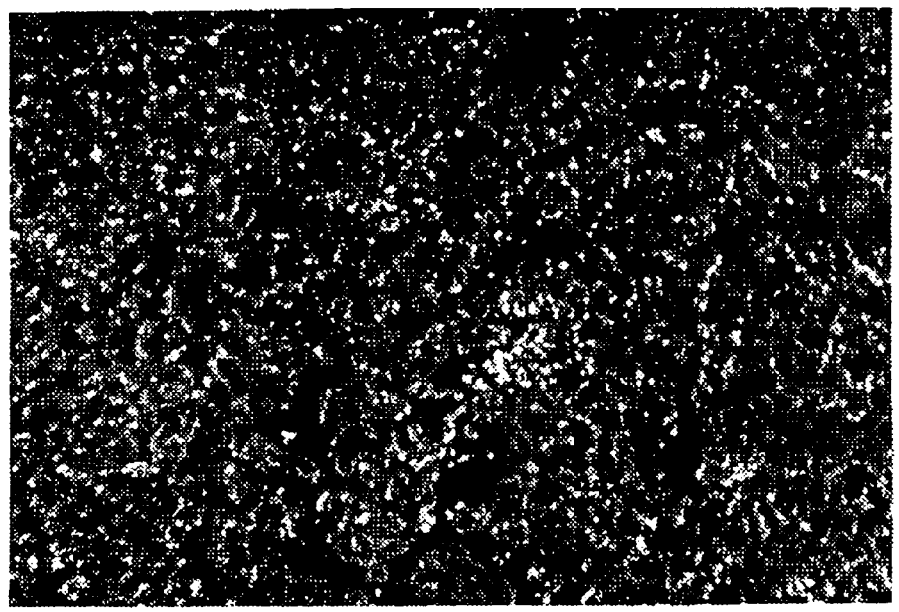

FIG. 21. In situ hybridization showing the expression of MCK-10 in cells of a medulloblastoma with hyperchromatic atypical nuclei. Expression of MCK-10 is predominantly in cells with well developed cytoplasm.

5. DETAILED DESCRIPTION

The present invention relates to a novel family of receptor tyrosine kinases referred to herein as MCK-10. The invention relates to differentially spliced isoforms of MCK-10 and to additional members of the MCK-10 family of receptor tyrosine kinases such as the CCK-gene described herein. The invention is based, in part, on the isolation of a cDNA clone encoding the MCK-10 receptor tyrosine kinase and the discovery of differentially spliced isoforms of MCK-10. The invention also relates to the isolation of a cDNA encoding on additional member of MCK-10 receptor tyrosine kinase family, herein referred to as CCK-2.

Results from Northern Blot analysis and in situ hybridization indicates that MCK-10 is expressed in epithelial cells. In addition, MCK-10 expression can be detected in a wide variety of cancer cells lines and in all tested tumors. The invention relates to, expression and production of MCK-10 protein, as well as to inhibitors of MCK-10 receptor activity which may have therapeutic value in the treatment of diseases such as cancer.

For clarity of discussion, the invention is described in the subsections below by way of example for the MCK-10 gene depicted in FIGS. 1A–1G and the CCK-2 gene depicted in FIGS. 3A–3H. However, the principles may be analogously applied to differentially spliced isoforms of MCK-10 and to other members of the MCK-10 family of receptors.

5.1. The MCK-10 Coding Sequence

The nucleotide coding sequence and deduced amino acid sequence of the human MCK-10 gene is depicted in FIGS. 1A–1G(SEQ. ID NO. 1). In accordance with the invention, any nucleotide sequence which encodes the amino acid sequence of the MCK-10 gene product can be used to generate recombinant molecules which direct the expression of MCK-10. In additional embodiments of the invention, nucleotide sequences which selectively hybridize to the MCK-10 nucleotide sequence shown in FIGS. 1A–1G (SEQ ID NO: 1) may also be used to express gene products with MCK-10 activity. Hereinafter all such variants of the MCK-10 nucleotide sequence will be referred to as the CK-10 DNA sequence.

In a specific embodiment described herein, the human MCK-10 gene was isolated by performing a polymerase chain reaction (PCR) in combination with two degenerate oligonucleotide primer pools that were designed on the basis of highly conserved sequences within the kinase domain of receptor tyrosine kinases corresponding to the amino acid sequence HRDLAA (sense primer) and SDVWS/FY (antisense primer) (Hanks et al., 1988). As a template cDNA synthesized by reverse transcription of poly-A RNA from the human mammary carcinoma cell line MCF7, was used. A novel RTK, designated MCK-10 (mammary carcinoma kinase 10) was identified that within the tyrosine kinase domain exhibited extensive sequence similarity to the insulin receptor family. The PCR fragment was used to screen a lambda gt11 library of human fetal brain cDNA (Clontech). Several overlapping clones were identified. The composite of these cDNA clones is depicted in FIGS. 1A–1G. Furthermore, screening of a human placental library yielded two cDNA clones, MCK-10-1 and MCK-10-2, which encoded the entire MCK-10 protein but contained a shorter 5' untranslated region starting at position 278 of the MCK-10 sequence (FIGS. 1A–1G). Sequences analysis of the two clones revealed complete identity with the exception of 111 additional nucleotides within the juxtamembrane domain, between nucleotides 1832 and 1943. One of the clones isolated from the human fetal brain library contained an additional 18 nucleotides in the tyrosine kinase domain. These sequences were in-frame with the MCK-10 open reading frame and did not contain any stop codons. The MCK-10 splice isoforms have been designated MCK-10-1 (with the additional 111 bp), MCK-10-2 (without any insertions), MCK-10–3 (with the additional 111 bp and 18 bp), and MCK-10-4 (with the additional 18 bp) (FIG. 2).

As shown in FIGS. 1A–1G and FIGS. 3A–3H, MCK-10 have all of the characteristics of a receptor PTK: the initiation codon is followed by a stretch of essentially hydrophobic amino acids, which may serve as a signal peptide. Amino acids 417–439 are also hydrophobic in nature, with the characteristics of a transmembrane region. The extracellular domain encompasses 4 consensus N-glycosylation sites (AsnXSer/Thr) and 7 cysteine residues. The extracellular region is shorter than that of the insulin receptor family and shows no homology to other receptor tyrosine kinases, but contains near the N-terminus the consensus sequences for the discoidin I like family (Poole et al. 1981, J. Mol. Biol. 153: 273–289), which are located as tandem repeats in MGP and BA46, two milk fat globule membrane proteins (Stubbs et al. 1990, Proc. Natl. Acad. Sci. USA, 87, 8417–8421, Larocca et al. 1991, Cancer Res. 51: 4994–4998), in the light chains of factor V (Kane et al. 1986, Proc. Natl. Acad. Sci. USA, 83: 6800–6804) and VIII (Toole et al. 1984, Nature 312: 342–347), and in the A5 protein (Takagi et al. 1987, Dev. Biol., 122: 90–100).

The protein backbone of MCK-10-1 and MCK-10-2 proreceptors, with predicted molecular weights of 101.13 and 97.17 kD, respectively, can thus be subdivided into a 34.31 kD α subunit and 66.84 or 62.88 kD β-subunits that contain the tyrosine kinase homology and alternative splice sites.

The consensus sequence for the ATP-binding motif is located at positions 617–627. When compared with other kinases, the ATP binding domain is 176 amino acids (including the additional 37 amino acids) further from the transmembrane domain than any other tyrosine kinase. The additional 37 amino acids are located in the long and proline/glycine-rich juxtamembrane region and contain an NPAY sequence (SEQ ID NO:5) (where A can be exchanged for any amino acid), which is found in cytoplasmic domains of several cell surface proteins, including RTKs of the EGF and insulin receptor families (Chen et al. 1990, J. Biol: Chem., 265: 3116–3123). This consensus motif is followed by the sequence TYAXPXXXPG (SEQ ID NO:6), which is repeated downstream in MCK-10 in the juxtamembrane domain at positions 585–595. Recently it has been shown that this motif is deleted in the cytoplasmic juxtamembrane region of the activin receptor, serine/threonine kinase, resulting in reduced ligand binding affinity (Attisano et al. 1992, Cell, 68: 97–108).

In comparison with other RTKs the catalytic domain shows the highest homology to the TrkA receptor. The YY-motifs (position 802/803) and the tyrosine at position 798, representing putative autophosphorylation sites, characterize MCK-10 as a member of the insulin receptor family. Finally, MCK-10 shares homology with the Trk kinases with their characteristic short carboxyl-terminal tail of 9 amino acids.

To determine whether the additional 111 nucleotides present in MCK-10-1 and -3 were ubiquitously expressed or expressed only in specific human tissues, a PCR analysis on different human cDNAs using oligonucleotide primers corresponding to sequences flanking the insertion site was carried out. Parallel PCR amplifications were performed on plasmid DNAs of MCK-10-1/MCK-10-2 as controls. Expression of both isoforms were identified in brain, pancreas, placenta, colon, and kidney, and in the cell lines Caki 2 (kidney ca), SW 48 (colon ca), and HBL100 and T47 D (breast ca). The PCR products were subcloned into the Bluescript vector to confirm the nucleotide sequence.

Using a hybridization probe comprising the 5'1694 bp cDNA fragment of MCK-10 (excluding the 111 bp insert), which encompasses the extracellular, transmembrane, and juxtamembrane domains, the MCK-10 gene revealed the existence of multiple transcript sizes with a major form of 4.2 kb. The highest expression of MCK-10 mRNA was detected in lung, intermediate levels were found in kidney, colon, stomach, placenta and brain, low levels in pancreas, and no MCK-10 mRNA was detected in liver (FIG. 5A). FIG. 5B illustrates the levels of expression of MCK-10 in a variety of breast cancer cell lines and FIG. 5C presents the levels of MCK-10 expression in different tumor cell lines. A summary of the expression patterns of MCK-10 in different cell lines is presented in TABLE 1.

TABLE 1

| MCK-10 EXPRESSION IN DIFFERENT CELL LINES | |
| --- | --- |
| BREAST CANCER CELL LINES | |
| BT-474 | + |
| T-47D | ++++ |
| BT-20 | +++ |
| MDA-MB-453 | ++ |
| MDA-MB-468 | ++ |
| MDA-MB-435 | ++ |
| MDA-MB-175 | ++++ |
| MDA-MB-231 | ++ |

TABLE 1-continued

MCK-10 EXPRESSION IN DIFFERENT CELL LINES

| | |
|---|---|
| HBL 100 | + |
| SK-BR-3 | + |
| MCF-7 | ++ |
| LUNG CANCER CELL LINES | |
| WI-38 | + |
| WI-26 | + |
| MELANOMA CELL LINES | |
| SK-Mel-3 | + |
| Wm 266-4 | + |
| HS 294T | ++ |
| COLON CANCER CELL LINES | |
| Caco-2 | +++ |
| -SNU-C2B | +++ |
| SW48 | ++ |
| KIDNEY CANCER CELL LINE | |
| CAKI-2 | +++ |
| EPIDERMOID CANCER CELL LINE | |
| A431 | ++ |
| OTHER CANCERS | |
| rhabdomyosarcoma | ++ |
| Ewing sarcoma | ++ |
| glioblastoma | ++ |
| neuroblastoma | − |
| hepatoblastoma | + |
| HEMAPOIETIC CELL LINES | |
| EB3 | − |
| CEM | − |
| MOLT4 | − |
| DAUDI | − |
| RAJI | − |
| MEG01 | − |
| KG1 | − |
| K562 | − |

In situ hybridization analysis with the 5'1865 bp of MCK-10-2 indicated that MCK-10 was expressed specifically in epithelial cells of various tissues including:

cuboidal epithelial cells lining the distal kidney tubulus (FIG. 7)

columnar epithelial cells lining the large bowel tract deep layer of epithelial cells lining the stomach epithelial cells lining the mammary ducts islet cells of the pancreas (FIG. 13 and FIG. 14)

epithelial cells of the thyroid gland, which produces thyroid hormones

No detectable MCK-10 expression was observed in connective tissues, endothelial cells, adipocytes, muscle cells, or hemopoietic cells.

MCK-10 expression was also detected in all tumors investigated which included:

adenocarcinoma of the colon (FIG. 16 and FIG. 17)

adenocarcinoma of the stomach adenocarcinoma of the lung infiltrating ductal carcinoma of the breast cystadenoma of the ovary multi endocrine tumor of the pancreas carcinoid tumor of the pancreas tubular cells of renal cell carcinoma transitional cell carcinoma (a malignant epithelial tumor of the bladder)

meningiothelial tumor (FIG. 18)

medulloblastoma with hyperchromatic atypical nuclei and spare cytoplasm (MCK-10 expression is only seen in cells with well developed cytoplasm) (FIG. 20 and FIG. 20)

glioblastoma (a tumor of the neuroepithelial tissue) (FIG. 19)

The in situ hybridization experiments revealed the highest expression of MCK-10 in malignant cells of the ductal breast carcinoma, in the tumor cells of a multi-endocrine tumor, and in the tumor cells of a transitional cell carcinoma of the bladder.

5.2 The CCK-2 Coding Sequence

The present invention also relates to other members of the MCK-10 family of receptor kinases. Members of the MCK-10 family are defined herein as those DNA sequences capable of.hybridizing to MCK-10 DNA sequences as presented in FIGS. 1A–1G. Such receptors may demonstrate 80% homology at the amino acid level in substantial stretches of DNA sequences. In addition, such receptors can be defined as those receptors containing an intracellular tyrosine kinase domain and a discoidin I sequence located near the amino-terminal end of the protein. The discoidin I domain is defined as that region of MCK-10 located between amino acid 31–185 as presented in FIG. 1.

In a specific embodiment of the invention described herein, an additional member of the MCK-10 family of receptor tyrosine kinases was cloned and characterized. The nucleotide coding sequence and deduced amino acid sequence of the novel receptor tyrosine kinase, herein referred to as CCK-2, is presented in FIGS. 3A–3H. In accordance with the invention, any nucleotide sequence which encodes the amino acid sequence of the CCK-2 gene product can be used to generate recombinant molecules which direct the expression of CCK-2. In additional, embodiments of the invention, nucleotide sequences which selectively hybridize to the CCK-2 nucleotide sequence as shown in FIGS. 3A–3H, (SEQ. ID NO: 2) may also be used to express gene products with CCK-2 activity.

Analysis of the CCK-2 sequence revealed significant homology to the extracellular, transmembrane and intracellular region of the MCK-10 receptor indicating that it was a member of the MCK-10 family of receptors. The shared homology between CCK-2 and MCK-10 is depicted in FIGS. 4A–4C.

5.3. Expression of MCK-10 Recepteor and Generation of Cell Lines That Express MCK-10

For clarity of discussion the expression of receptors and generation of cell lines expressing receptors are described by way of example for the MCK-10 gene. However, the principles may be analogously applied to expression and generation of cell lines expressing spliced isoforms of MCK-10 or to other members of the MCK-10 family of receptors, such as CCK-2.

In accordance with the invention, MCK-10 nucleotide sequences which encode MCK-10, peptide fragments of MCK-10, MCK-10 fusion proteins or functional equivalents thereof may be used to generate recombinant DNA molecules that direct the expression of MCK-10 protein or a functionally equivalent thereof, in appropriate host cells. Alternatively, nucleotide sequences which hybridize to portions of the MCK-10 sequence may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the cloning and expression of the MCK-10 protein. Such DNA sequences include those which are capable of hybridizing to the human MCK-10 sequence under stringent conditions.

Altered DNA sequences which may be used in accordance with the invention include deletions, additions or substitutions of different nucleotide residues resulting in a sequence that encodes the same or a functionally equivalent gene product. These alterations would in all likelihood be in regions of MCK-10 that do not constitute functionally conserved regions such as the discordin I domain or the tyrosine kinase domain. In contrast, alterations, such as deletions, additions or substitutions of nucleotide residues in functionally conserved MCK-10 regions would possibly result in a nonfunctional MCK-10 receptor. The gene product itself may contain deletions, additions or substitutions of amino acid residues.within the MCK-10 sequence, which result in a silent change thus producing a functionally equivalent MCK-10. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. The DNA sequences of the invention may be engineered in order to alter the MCK-10 coding sequence for a variety of ends including but not limited to alterations which modify processing and expression of the gene product. For example, mutations may be introduced using techniques which are well known in the art, e.g. site-directed mutagenesis, to insert new restriction sites, to alter glycosylation patterns, phosphorylation, etc. For example, in certain expression systems such as yeast, host cells may over glycosylate the gene product. When using such expression systems it may be preferable to alter the MCK-10 coding sequence to eliminate any N-linked glycosylation site.

In another embodiment of the invention, the MCK-10 or a modified MCK-10 sequence may be ligated to a heterologous sequence to encode a fusion protein. For example, for screening of peptide libraries it may be useful to encode a chimeric MCK-10 protein expressing a heterologous epitope that is recognized by a commercially available antibody. A fusion protein may also be engineered to contain a cleavage site located between the MCK-10 sequence and the heterologous protein sequence, so that the MCK-10 may be cleaved away from the heterologous moiety.

In an alternate embodiment of the invention, the coding sequence of MCK-10 could be synthesized in whole or in part, using chemical methods well known in the art. See, for example, Caruthers, et al., 1980, Nuc. Acids Res. Symp. Ser. 7:215–233; Crea and Horn, 180, Nuc. Acids. Res. 9 (10):2331; Matteucci and Caruthers, 1980, Tetrahedron Letters 21:719; and Chow and Kempe, 1981, Nuc. Acids. Res. 9 (12):2807–2817. Alternatively, the prot in its If could be produced using chemical methods to synthesize the MCK-10 amino acid sequence in whole or in part. For example, peptides can be synthesized by solid phase techniques, cleaved from the resin, and purified by preparative high performance liquid chromatography. (E.g , see Creighton, 1983, Proteins Structures And Molecular Principles, W. H. Freeman and Co., N.Y. pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49.

In order to express a biologically active MCK-10, the nucleotide sequence coding for MCK-10, or a functional equivalent, is inserted into an appropriate expression vector, i.e., a vector which contains the necessary elements for the transcription and translation of the inserted coding sequence. The MCK-10 gene products as well as host cells or cell lines transfected or transformed with recombinant MCK-10 expression vectors can be used for a variety of purposes. These include but are not limited to generating antibodies (i.e., monoclonal or polyclonal) that bind to the receptor, including those that competitively inhibit binding of MCK-10 ligand and "neutralize" activity of MCK-10 and the screening and selection of drugs that act via the MCK-10 receptor; etc.

5.3.1. Expression Systems

Methods which are well known to those skilled in the art can be used to construct expression vectors containing the MCK-10 coding sequence and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the MCK-10 coding sequence. These include but are not limited to microorganisms such as bacteria transformed with recombinant bacteriophage DNA, plasmid DNA or cosmid DNA expression vectors containing the MCK-10 coding sequence; yeast transformed with recombinant yeast expression vectors containing the MCK-10 coding sequence; insect cell systems infected with recombinant virus expression vectors (e.g, baculovirus) containing the MCK-10 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the MCK-10 coding sequence; or animal cell systems The expression elements of these systems vary in their strength and specificities. Depending on the host/vector system utilized, any of a number of suitable transcription and translation elements, including constitutive and inducible promoters, may be used in the expression vector. For example, when cloning in bacterial systems inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant c 11s (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the MCK-10 DNA, SV40-, BPV- and EBV-based vectors may be used with an appropriate selectable marker.

In bacterial systems a number of expression vectors may be advantageously selected depending upon the use intended for the MCK-10 expressed. For example, when large quantities of MCK-10 are to be produced for the generation of antibodies or to screen peptide libraries, vectors which direct the expression of high levels of fusion protein products that are readily purified may be desirable. Such vectors include but are not limited to the E coli expression vector pUR278 (Ruther et al., 1983, EMBO J. 2:1791), in which the MCK-10 coding sequence may be ligated into the vector in frame with the lac Z coding region so that a hybrid AS-lac Z protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sit s so that the cloned polypeptide of interest can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II.

In cases where plant expression vectors are used, the expression of the MCK-10 coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

An alternative expression system which could be used to express MCK-10 is an insect system. In one such system, *Autographa californica* nuclear polyhidrosis virus (AcNPV) is used as a vector to express foreign genes. The virus grows in *Spodoptera frugiperda* cells. The MCK-10 coding sequence may be cloned into non-essential regions (for example the polyhedrin gene) of the virus and placed under control of an AcNPV promoter (for example the polyhedrin promoter). Successful insertion of the MCK-10 coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the MCK-10 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing MCK-10 in infected hosts. (E.g., See Logan & Shenk, 1984, Proc. Natl. Acad. Sci. (USA) 81:3655–3659). Alternatively, the vaccinia 7.5K promoter may be used. (See, e.g., Mackett et al., 1982, Proc. Natl. Acad. Sci. (USA) 79:7415–7419; Mackett et al., 1984, J. Virol. 49:857–864; Panicali et al., 1982, Proc. Natl. Acad. Sci. 79:4927–4931).

Specific initiation signals may also be required for efficient translation of inserted MCK-10 coding sequences. These signals include the ATG initiation codon and adjacent sequences. In cases where the entire MCX-10 gene, including its own initiation codon and adjacent sequences, is inserted into the appropriate expression vector, no additional translational control signals may be needed. However, in cases where only a portion of the MCK-10 coding sequence is inserted, exogenous translational control signals, including the ATG initiation codon, must be provided. Furthermore, the initiation codon must be in phase with the reading frame of the MCK-10 coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. The presence of four consensus N-glycosylation sites in the MCK-10 extracellular domain support that proper modification may be important for MCK-10 function. Different host cells have characteristic and specific mechanisms for the post-translational processing and modification of proteins. Appropriate cells lines or host systems can be chosen to ensure the correct modification and processing of the foreign protein expressed. To this and, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express the MCK-10 may be engineered. Rather than using expression vectors which contain viral origins of replication, host cells can be transformed with the MCK-10 DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the MCK-10 on the cell surface. Such engineered cell lines are particularly useful in screening for drugs that affect MCK-10.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^{-, hgprt-}$ or $aprt^-$ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981), Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current communications in Molecular Biology, Cold Spring Harbor Laboratory ed.).

5.3.2. Identification of Transfectants or Transformants that Express the MCK-10

The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of MCK-10 mRNA transcripts in the host cell; and (d) detection of the gene product as measured by immunoassay or by its biological activity.

In the first approach, the presence of the MCK-10 coding sequence inserted in the expression vector can be detected by DNA-DNA or DNA-RNA hybridization using probes comprising nucleotide sequences that are homologous to the MCK-10 coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the MCK-10 coding sequence is inserted within a marker gene sequence of the vector, recombinants containing the MCK-10 coding sequence can be identified by the absence of the marker gene function. Alternatively, a marker gene can be placed in tandem with the MCK-10 sequence under the control of the same or different promoter used to control the expression of the MCK-10 coding sequence. Expression of the marker in response to induction or selection indicates expression of the MCK-10 coding sequence.

In the third approach, transcriptional activity for the MCK-10 coding region can be assessed by hybridization assays. For example, RNA can be isolated and analyzed by Northern blot using a probe homologous to the MCK-10 coding sequence or particular portions thereof. Alternatively, total nucleic acids of the host cell may be extracted and assayed for hybridization to such probes.

In the fourth approach, the expression of the MCK-10 protein product can be assessed immunologically, for example by Western blots, immunoassays such as radioimmuno-precipitation, enzyme-link d immunoassays and the like.

5.4. Uses of the MCK-10 Receptor and Engineered Cell Lines

For clarity of discussion the uses of the expressed receptors and engineered cell lines expressing the receptors is described by way of example for MCK-10. The described uses may be equally applied to expression of MCK-10 spliced isoforms or additional members of the MCK-10 gene family such as CCK-2.

In an embodiment of the invention the MCK-10 receptor and/or cell lines that express the MCK-10 receptor may be used to screen for antibodies, peptides, or other ligands that act as agonists or antagonists of the MCK-10 receptor. For example, anti-MCK-10 antibodies may be used to inhibit MCK-10 function. Alternatively, screening of peptide libraries with recombinantly expressed soluble MCK-10 protein or cell lines expressing MCK-10 protein may be useful for identification of therapeutic molecules that function by inhibiting the biological activity of MCK-10. The uses of the MCK-10 receptor and engineered cell lines, described in the subsections below, may be employed equally well for MCK-10 family of receptor tyrosine kinases.

In an embodiment of the invention, engineered cell lines which express the entire MCK-10 coding region or its ligand binding domain may be utilized to screen and identify ligand antagonists as well as agonists. Synthetic compounds, natural products, and other sources of potentially biologically active materials can be screened in a number of ways.

5.4.1. Screening of Peptide Library with MCK-10 Protein or Engineered Cell Lines Random peptide libraries consisting of all possible combinations of amino acids attached to a solid phase support may be used to identify peptides that are able to bind to the ligand binding site of a given receptor or other functional domains of a receptor such as kinase domains (Lam, K. S. et al., 1991, Nature 354: 82–84). The screening of peptide libraries may have therapeutic value in the discovery of pharmaceutical agents that act to inhibit the biological activity of receptors through their interactions with the given receptor.

Identification of molecules that are able to bind to the MCK-10 may be accomplished by screening a peptide library with recombinant soluble MCK-10 protein. Methods for expression and purification of MCK-10 are described in Section 5.2.1 and may be used to express recombinant full length MCK-10 or fragments of MCK-10 depending on the functional domains of interest. For example, the kinase and extracellular ligand binding domains of MCK-10 may be separately expressed and used to screen peptide libraries.

To identify and isolate the peptide/solid phase support that interacts and forms a complex with MCK-10, it is necessary to label or "tag" the MCK-10 molecule. The MCK-10 protein may be conjugated to enzymes such as alkaline phosphatase or horseradish peroxidase or to other reagents such as fluorescent labels which may include fluorescein isothyiocynate (FITC), phycoerythrin (PE) or rhodamine. conjugation of any given label, to MCK-10, may be performed using techniques that are routine in the art. Alternatively, MCK-10 expression vectors may be engineered to express a chimeric MCK-10 protein containing an epitope for which a commercially available antibody exist. The epitope specific antibody may be tagged using methods well known in the art including labeling with enzymes, fluorescent dyes or colored or magnetic beads.

The "tagged" MCK-10 conjugate is incubated with the random peptide library for 30 minutes to one hour at 22° C. to allow complex formation between MCK-10 and peptide species within the library. The library is then washed to remove any unbound MCK-10 protein. If MCK-10 has been conjugated to alkaline phosphatase or horseradish peroxidase the whole library is poured into a petri dish containing substrates for either alkaline phosphatase or peroxidase, for example, 5-bromo-4-chloro-3-indoyl phosphate (BCIP) or 3,3', 4,4"-diamnobenzidine (DAB), respectively. After incubating for several minutes, the peptide/solid phase-MCK-10 complex changes color, and can be easily identified and isolated physically under a dissecting microscope with a micromanipulator. If a fluorescent tagged MCK-10 molecule has been used, complexes may be isolated by fluorescent activated sorting. If a chimeric MCK-10 protein expressing a heterologous epitope has been used, detection of the peptide/MCK-10 complex may be accomplished by using a labeled epitope specific antibody. Once isolated, the identity of the peptide attached to the solid phase support may be determined by peptide sequencing.

In addition to using soluble MCK-10 molecules, in another embodiment, it is possible to detect peptides that bind to cell surface receptors using intact cells. The use of intact cells is preferred for use with receptors that are multi-subunits or labile or with receptors that require the lipid domain of the cell membrane to be functional. Methods for generating cell lines expressing MCK-10 are described in Sections 5.2.1. and 5.2.2. The cells used in this technique may be either liv or fixed cells, The cells will be incubated with the random peptide library and will bind to certain peptides in the library to form a "rosette" between the target cells and the relevant solid phase support/peptide. The rosette can thereafter be isolated by differential centrifugation or removed physically under a dissecting microscope.

As an alternative to whole cell assays for membrane bound receptors or receptors that require the lipid domain of the cell membrane to be functional, the receptor molecules can be reconstituted into liposomes where label or "tag" can be attached.

5.4.2. Antibody Production and Screening

Various procedures known in the art may be used for the production of antibodies to epitopes of the recombinantly produced MCK-10 receptor. Such antibodies include but are not limited to polyclonal, monoclonal, chimeric, single chain, Fab fragments and fragments produced by an Fab expression library. Neutralizing antibodies i.e., those which compete for the ligand binding site of the receptor are especially preferred for diagnostics and therapeutics.

Monoclonal antibodies that bind MCK-10 may be radioactively labeled allowing one to follow their location and distribution in the body after injection. Radioactivity tagged antibodies may be used as a non-invasive diagnostic tool for imaging de novo cells of tumors and metastases.

Immunotoxins may also be designed which target cytotoxic agents to specific sites in the body. For example, high affinity MCK-10 specific monoclonal antibodies may be covalently complexed to bacterial or plant toxins, such as diphtheria toxin, abrin or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate MCK-10 expressing tumor cells.

For the production of antibodies, various host animals may be immunized by injection with the MCK-10 protein including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum.*

Monoclonal antibodies to MCK-10 may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce MCK-10-specific single chain antibodies.

Antibody fragments which contain specific binding sites of MCK-10 may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity to MCK-10.

5.5. Uses of MCX-10 Coding Sequence

The MCK-10 coding sequence may be used for diagnostic purposes for detection of MCK-10 expression. Included in the scope of the invention are oligoribonucleotide sequences, that include antisense RNA and DNA molecules and ribozymes that function to inhibit translation of MCK-10. In addition, mutated forms of MCK-10, having a dominant negative effect, may be expressed in targeted cell populations to inhibit the activity of endogenously expressed MCK-10. The uses described below may be equally well adapted for MCK-10 spliced isoform coding sequences and sequences encoding additional members of the MCK-10 family of receptors, such as CCK-2.

5.5.1. Use of MCK-10 Coding Sequence in Diagnostics and Therapeutics

The MCK-10 DNA may have a number of uses for the diagnosis of diseases resulting from aberrant expression of MCK-10. For example, the MCK-10 DNA sequence may be used in hybridization assays of biopsies or autopsies to diagnose abnormalities of MCK-10 expression; e.g., Southern or Northern analysis, including in situ hybridization assays.

Also within the scope of the invention are oligoribonucleotide sequences, that include anti-sense RNA and DNA molecules and ribozymes that function to inhibit the translation of MCK-10 mRNA. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of the MCK-10 nucleotide sequence, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of MCK-10 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

5.5.2. Use of Dominant Negative Mutants in Gene Therapy

Receptor dimerization induced by ligands, is thought to provide an allosteric regulatory signal that functions to couple ligand binding to stimulation of kinase activity. Defective receptors can function as dominant negative mutations by suppressing the activation and response of normal receptors by formation of unproductive heterodimers. Therefore, defective receptors can be engineered into recombinant viral vectors and used in gene therapy in individuals that inappropriately express MCK-10.

In an embodiment of the invention, mutant forms of the MCK-10 molecule having a dominant negative effect may be identified by expression in selected cells. Deletion or missense mutants of MCK-10 that retain the ability to form dimers with wild type MCK-10 protein but cannot function in signal transduction may be used to inhibit the biological activity of the endogenous wild type MCK-10. For example, the cytoplasmic kinase domain of MCK-10 may be deleted resulting in a truncated MCK-10 molecule that is still able to undergo dimerization with endogenous wild type receptors but unable to transduce a signal.

Recombinant viruses may be engineered to express dominant negative forms of MCK-10 which may be used to inhibit the activity of the wild type endogenous MCK-10. These viruses may be used therapeutically for treatment of diseases resulting from aberrant expression or activity of MCK-10, such as cancers.

Expression vectors derived from viruses such as retroviruses, vaccinia virus, adeno-associated virus, herpes viruses, or bovine papilloma virus, may be used for delivery of recombinant MCX-10 into the targeted cell population. Methods which are well known to those skilled in the art can be used to construct those recombinant viral vectors containing MCK-10 coding sequence. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. Alternatively, recombinant MCK-10 molecules can be reconstituted into liposomes for delivery to target cells.

6. EXAMPLES

Cloning and Characterization of MCK-10

The subsection below describes the isolation and characterization of a cDNA clones encoding the novel receptor tyrosine kinase designated MCK-10 and differentially spliced isoforms of MCK-10.

6.1. Materials and Methods 6.1.1. cDNA Cloning and Characterization of MCK-10

Confluent plates of the human breast cancer cell line MCF7 (American Type Culture Collection HTB22) were lysed by treatment with guanidinium-thiocyanate according to Chirgwin et al. (1979, Biochemistry 18:5294–5299). Total RNA was isolated by CsCl-radient centrifugation. First-strand cDNA was synthesized from 20 µg total RNA with avian myeloblastosis virus (AMV) reverse transcriptase (Boehringer Mannheim).

cDNA was used in a polymerase chain reaction under standard conditions (*PCR Technology-Principles and Applications for DNA Amplifications*, H. E. Erlich, ed., Stockton Press, New York 1989). The following pool of primers were used for the amplification:

Sense Primer

Corresponding to the Amino Acid Sequence HRDLAA

```
      ECoRI
5' GGAATTCC CAC AGN GAC TTN GCN GCN AG 3'
             T C  AT C  A   A   C
```

Antisense Primer
Corresponding to the Amino Acid Sequence SDVWS

```
                                          EcoRI
      3' TCN GAC GTN TGG ACN TTC CCTTAAGG 5'
          G   G           TG  CAT
```

Thirty-five PCR cycles were carried out using 8 µg (0.8 µg) of the pooled primers. (Annealing 55° C., 1 min; Extension 72° C., 2 min; Denaturation 94° C., 1 min). The reaction product was subjected to polyacrylamide gel electrophoresis. Fragments of the expected size (~210 bp) were isolated, digested with the restriction enzyme EcoRI, and subcloned into the pBluescript vector (Stratagene) using standard techniques (Current Protocols in Molecular Biology, eds. F. M. Ausubel et al., John Wiley & Sons, New York, 1988).

The recombinant plasmids were transformed into the competent E. coli strain designated 298.

The subcloned PCR products were sequenced by the method of Sanger et al. (Proc. Natl. Acad. Sci. USA 74, 5463–5467) using Sequenase (United States Biochemical, Cleveland, Ohio 44111 USA). One clone, designated MCK-10 was identified as novel RTK.

6.1.2. Full-length cDNA Cloning

The partial cDNA sequence of the new MCK-10 RTK, which was identified by PCR, was used to screen a λgt11 library from human fetal brain cDNA (Clontech) (complexity of $1 \times 10^{10}$ recombinant phages). One million independent phage clones were plated and transferred to nitrocellulose filters following standard procedures (Sambrook, H. J., Molecular Cloning, Cold Spring Harbor Laboratory Press, USA, 1989). The filters were hybridized to the EcoRI/EcoRI fragment of clone MCK-10, which had been radioactively labeled using 50 µCi [$\alpha^{32}$ P]ATP and the random-primed DNA labeling kit (Boehringer Mannheim). The longest cDNA insert (8) of ~3500 bp was digested with the restriction enzymes EcoRI/SacI to obtain a 5' end probe of 250 bp. This probe was used to rescreen the human fetal brain library and several overlapping clones were isolated. The composite of the cDNA clones are shown in FIGS. 1A–1G. Some of the clones had a deletion of 6 amino acids at position 2315 in the MCK-10 sequence.

The 1.75 million independent phage clones of a human placenta library, λZAP were plated and screened with the 5' end probe (EcoRI/SacI) of clone 8. Two clones were full-length with a shorter 5' end starting at position 278 of the nucleotide sequence shown in FIGS. 1A–1G. Subcloning of positive bacteriophages clones into pBluescript vector was done by the in vivo excision protocol (Stratagene).

The composite cDNA sequence and the predicted amino acid sequence of MCK-10 are shown in FIGS. 1A–1G. Different cDNA sequence variations of MCK-10 is presented in FIG. 2.

6.1.3. Northern Blot Analysis of MCK-10

Total RNA was isolated from the following human tissues: lung, pancreas, stomach, kidney, spleen, liver, colon and placenta. RNA was also isolated from various breast cancer cell lines and cell lines of tumor origin.

PolyA$^+$ RNA was isolated on an oligo (dT) column (Aviv and Leder, 1972, Proc. Natl. Acad. Sci. USA 69, 1408–1412). The RNA was separated on an agarose gel containing 2.2M formaldehyde and blotted on a nitrocellulose filter (Schleicher and Schuell). 3 µg of poly A$^+$ RNA was loaded per lane. The filter was hybridized with a $^{32}$P-labeled EcoRI/EcoRI DNA fragment obtained by PCR. Subsequently, the filter was exposed to x-ray film at −70° C. with an intensifying screen. The results are depicted in FIGS. 5A, 5B and 5C.

6.1.4. Generation of MCK-10Specific Antibodies

Antisera was generated against synthetic peptides corresponding to the amino acid sequence of MCK-10. αMCK-10-N antisera was generated against the following N-terminal peptide located between amino acids 26–42:

H-F-D-P-A-K-D-C-R-Y-A-L-G-M-Q-D-R-T-I.

αMCK-10-c antisera was generated against the following C-terminal peptide located between amino acids 902–919

R-P-P-F-S-Q-L-H-R-F-L-A-E-D-A-L-N-T-V.

αMCK-10-β antisera was generated against the following peptide near the processing site of β-subunit of MCK-10 located between amino acids 309–322:

P-A-M-A-W-E-G-E-P-M-R-H-N-L.

αMCK-10-C2 antisera was generated against the C-terminal peptide located between amino acids 893–909:

C-W-S-R-E-S-E-Q-R-P-P-F-S-Q-L-H-R.

Peptides were coupled to keyhole limpet hemocyanin and injected with Freunds adjuvant into Chinchilla rabbits. After the second boost, the rabbits were bled and the antisera were tested in immunoprecipitations using lysates of 293 cells transiently overexpressing MCK-10-1 and MCK-10-2.

The samples wer loaded on a 7.5% polyacrylamide gel and aft r electrophoresis transferred onto a nitrocellulose filter (Schleicher and Schuell). The blot was probed with the different antibodies as above and developed using the ECL Western blotting detection system according the manufacturer's instructions (Cat no. RPN 2108 Amersham International, UK).

6.1.5. In Situ Hybridization

The 5' located cDNA fragment corresponding to nucleotides 278–1983 of clone MCK-10, excluding the 111 base pair insert, were subcloned in the bluescript SK+ (Stratagene). For in situ hybridization, a single-strand antisense DNA probe was prepared as described by Schnürch and Risau (Development 1991, 111, 1143–1154). The plasmid was linearized at the 3' end of the cDNA and a sense transcript was synthesized using SP6 RNA polymerase (Boehringer). The DNA was degraded using DNase (RNase-free preparation, Boehringer Mannheim). With the transcript, a random-primed cDNA synthesis with $\alpha$-$^{35}$S ATP (Amersham) was performed by reverse transcription with MMLV reverse transcriptase (BRL). To obtain small cDNA fragments of about 100 bp in average, suitable for in situ hybridization, a high excess of primer was used. Subsequently, the RNA transcript was partially hydrolyzed in 100 nM NaOH for 20 min at 70° C., and the probe was neutralized with the same amount of HCL and purified with a Sephadex-G50 column. After ethanol precipitation the probe was dissolved at a final specific activity of $5 \times 10^5$ cpm. For control hybridization, a sense probe was prepared using the same method.

Sectioning, postfixation was essentially performed according to Hogan et al. (1986, Manipulating the Mouse Embryo: A Laboratory Manual, New York: Cold Spring Harbor Laboratory Press). 10 µm thick sections were cut at −18° C. on a Leitz cryostat. For hybridization treatment, no incubation with 0.2M HCL for removing the basic proteins was performed. Sections were incubated with the $^{35}$S-cDNA probe ($5 \times 10^4$ cpm/µl) at 52° C. in a buffer containing 50% formamide, 300 mM NaCl, 10 mM Tris-HCL, 10 mM NaPO$_4$ (pH 6.8), 5 mM EDTA, 2% Ficoll 400, 0.2% polyvinylpyrrolidone, 0.02% BSA, 10 mg/ml yeast RNA, 10% dextran sulfate, and 10 mM DTT. Posthybridization washing was performed at high stringency (50% formamide, 300 mM NaCl, 10 mM Tris-HCL, 10 mM NaPO$_4$ (pH6.8), 5 mM EDTA, 10 mMDTT at 52° C.). For autoradiography, slides were created with Kodak NTB2 film emulsion and exposed for eight days. After developing, the sections were counterstained with toluidine blue.

6.2. Results
6.2.1. Characterization of MCK-10 Clone

To identify novel receptor tyrosine kinases (RTKs) that are expressed in mammary carcinoma cell lines, we used the polymerase chain reaction in combination with two degenerate oligonucleotide primer pools based on highly conserved sequences within the kinase domain of RTKs, corresponding to the amino acid sequence HRDLAA (sense primer) and SDVWS/FY (antisense primer) (Hanks et al. 1988, Science 241, 42–52), in conjunction with cDNA synthesized by reverse transcription of polyA RNA from the human mammary carcinoma cell line MCF7. We identified a novel RTK, designated MCK-10 (mammary carcinoma kinase 10), that within the tyrosine kinase domain exhibited extensive sequence similarity to the insulin receptor family. The PCR fragment was used to screen a lambda gt11 library of human fetal brain cDNA (Clontech). Several overlapping clones were identified and their composite sequence is shown in FIGS. 1A–1G. Furthermore, screening of a human placenta library yielded two cDNA clones which encoded the entire MCK-10 protein but whose 5' nucleotide sequence began at nucleotide 278 in the sequence shown in FIG. 1. Sequence analysis of the two clones revealed complete identity with the exception of 111 additional nucleotides within the juxtamembrane domain, between nucleotides 1832 and 1943. One of the clones isolated from the human fetal brain library contained an additional 18 nucleotides in the tyrosine kinase domain. These sequences were in-frame with the MCK-10 open reading frame and did not contain any stop codons. We designated these MCK-10 splice isoforms MCK-10-1 (with the additional 111 bp, MCK-10-2 (without any insertions), MCK-10-3 (with the additional 111 bp and 18 bp), and MCK-10-4 (with the additional 18 bp). This new receptor tyrosine kinase was recently described by Johnson et al. (1993, Proc. Natl. Acad. Sci. USA, 90 5677–5681) as DDR.

As shown in FIG. 1, MCK-10 has all of the characteristics of a receptor PTK: the initiation codon is followed by a stretch of essentially hydrophobic amino acids, which may serve as a signal peptide. Amino acids 417–439 are also hydrophobic in nature, with the characteristics of a transmembrane region. The extracellular domain encompasses 4 consensus N-glycosylation sites (AsnXSer/Thr) and 7 cysteine residues. The extracellular region is shorter than that of the insulin receptor family and shows no homology to other receptor tyrosine kinases, but contains near the N-terminus the consensus sequences for the discoidin 1 like family (Poole et al. 1981, J. Mol. Biol. 153, 273–289), which are located as tandem repeats in MGP and BA46, two milk fat globule membrane proteins (Stubbs et al. 1990, proc. Natl. Acad. Sci. USA, 87, 8417–8421, Larocca et al. 1991, Cancer Res. 51, 4994–4998), in the light chains of factor V (Kane et al. 1986, Proc. Natl. Acad. Sci. USA, 83, 6800–6804) and VIII (Toole et al. 1984, Nature, 312, 342–347), and in the A5 protein (Takagi et al. 1987, Dev. Biol., 122, 90–100).

The protein backbone of MCK-10-1 and MCK-10-2 proreceptors, with predicted molecular weights of 101.13 and 97.17 kD, respectively, can thus be subdivided into a 34.31 kD a subunit and 66.84 kD β-subunits that contain the tyrosine kinase homology and alternative splice sites.

The consensus sequence for the ATP-binding motif is located at positions 617–627. When compared with is other kinases, the ATP binding domain is 176 amino acids (including the additional 37 amino acids) further from the transmembrane domain than any other tyrosine kinase. The additional 37 amino acids are located in the long and proline/glycine-rich juxtamembrane region and contain an NPAY sequence (where A can be exchanged for any amino acid), which is found in cytoplasmic domains of several cell surface proteins, including RTKs of the EGF and insulin receptor families (Chen et al. 1990, J. Biol. Chem., 265, 3116–3123). This consensus motif is followed by the sequence TYAXPXXXPG, which is repeated downstream in MCK-10 in the juxtamembrane domain at positions 585–595. Recently it has been shown that this motif is deleted in the cytoplasmic juxtamembrane region of the activin receptor, a serine/threonine kinase, resulting in reduced ligand binding affinity (Attisano et al. 1992, Cell, 68, 97–108).

In comparison with other RTKs, the catalytic domain shows the highest homology to the TrkA receptor. The yy-motifs (position 802/803) and the tyrosine at position 798, representing putative autophosphorylation sites, characterize MCK-10 as a member of the insulin receptor family. Finally, MCK-10 shares with the Trk kinases their characteristic short caraboxy-terminal tail of 9 amino acids.

To determine whether the additional 111 nucleotides present in MCK-10-1 and -3 were ubiquitously expressed or expressed only in specific human tissues, we performed PCR on different human cDNAs using oligonucleotide primers corresponding to sequences flanking the insertion site. Parallel PCR amplifications were performed on plasmid DNAs of MCK-10-1/MCK-10-2 as controls. Expression of both isoforms was identified in brain, pancreas, placenta, colon, and kidney, and in the cell lines Caki 2 (kidney ca), SW 48 (colon ca), and HBL100 and T47D (breast ca). The PCR products were subcloned into the Bluescript vector to confirm the nucleotide sequence.

6.2.2. Northern Blot Analysis: Expression of MCK-10 in Various Human Tissues and Cell Lines Using as a hybridization probe a 5'1694 bp cDNA fragment of MCK-10 (excluding the 111 base pair insert), which encompasses the extracellular, transmembrane, and juxtamembrane domains, the MCK-10 gene revealed the existence of multiple transcript sizes with a major form of 4.2 kb. The highest expression of MCK-10 mRNA was detected in lung, intermediate levels were found in kidney, colon, stomach, placenta, and brain, low levels in pancreas, and no MCK-10 mRNA was detected in liver (FIG. 5A). MCK-10 mRNA was also detected in a variety of different tumor cell lines as depicted in FIG. 5B and FIG. 5C. Northern blot analysis with the GAPDH gene was carried out as a control.

6.2.3. In Situ Hybridization

To determine which c 11s in the different human tissues contain MCK-10 transcripts, in situ hybridization of various human tissues and of tissues of different tumors were carried out. Hybridization analyses with the 5'1694 bp of MCK-10 (excluding the 111 base pair insert) indicated that MCK-10 expression was specifically detected in epithelial cells of various tissues:

cuboidal epithelial cells lining the distal kidney tubulus
columnar epithelial cells lining the large bowl tract
deep layer of epithelial cells lining the stomach
epithelial cells lining the mammary ducts
islet cells of the pancreas
epithelial cells of the thyroid gland, which produces thyroid hormones No detectable MCK-10 expression was observed in connective tissues, endothelial cells, adipocytes, muscle cells, or hemapoletic cells.

MCK-10 expression was detected in all tumors investigated:

- adenocarcinoma of the colon
- adenocarcinoma of the stomach
- adenocarcinoma of the lung
- infiltrating ductal carcinoma of the breast
- cystadenoma of the ovary
- multi endocrine tumor of the pancreas
- carcinoid tumor of the pancreas
- tubular cells of renal cell carcinoma
- transitional cell carcinoma (a malignant epithelial tumor of the bladder)
- meninglothelial tumor medulloblastoma with hyperchromatic atypical nuclei and spare cytoplasm (MCK-10 expression is only seen in cells with well developed cytoplasm)
- glioblastoma (a tumor of the neuroepithelial tissue)

These in situ hybridization experiments revealed the highest expression of MCK-10 in malignant cells of the ductal breast carcinoma, in the tumor cells of a multi endocrine tumor, and in the tumor cells of a transitional cell carcinoma of the bladder. The in situ hybridization results are depicted in FIGS. 7–21.

6.2.4. Transient Overexpression of MCK-10 in 293 Cells

To analyze the MCK-10 protein in detail, we used the 293 cell system for transient overexpression. The cDNAs of MCK-10-1 and MCK-10-2 were cloned into an expression vector. Cells were transfected in duplicate with the two splice variants or a control plasmid and starved overnight. One part was incubated prior to lysis with 1 mM sodium-orthovanadate for 90 min. This agent is known to be a potent inhibitor of phosphotyrosine phosphatases, thereby enhancing the tyrosine phosphorylation of cellular protein.

The precursor and the β-subunit of MCK-10 showed strong tyrosine phosphorylation after orthovanadate treatment, (FIGS. 4A and 4B, left panel). Surprisingly, the MCK-10-1, containing the 37 amino acid insertion, exhibited lower kinase activity than MCK-10-2. Reprobing the same blot with a peptide antibody raised against the MCK-10 C-terminus revealed equal amounts of expressed receptor and a slight shift of MCK-10-1 precursor and β-subunit due to the additional 37 amino acids of the insertion (FIGS. 4A and 4B, right panel).

We further analyzed the N-linked glycosylation of the splice variants. Transfected cells were treated overnight with tunicamycin, which inhibits the maturation of proteins by glycosylation. Two affinity purified antibodies raised against peptide sequence of MCK-10 N- and C-terminus, respectively, were used for subsequent immunoprecipitations. Both antibodies precipated the predicted 101 kD or 97 kD polypeptides from tunicamycin-treated cells (FIG. 4C). Interestingly, the size of the fully glycosylated forms of MCK-10-1 and MCK-10-2 suggested that the latter was more extensively glycosylated than the putative alternative splice form. This data indicates that the 37 amino acid insertion of MCK-10-1 influences its posttranslational modification which may influence ligand.

7. EXAMPLES

Cloning and Characterization of CCK-2

The following subsection describes methods for isolation and characterization of the CCK-2 gene, an additional member of the MCK-10 receptor tyrosine kinase gene family.

7.1. Materials and Methods 7.1.1. cDNA Cloning and Characterization of CCK-2 cDNA was synthesized using avian myeloblastosis virus reverse transcriptase and 5 μg of poly $A^+$ RNA prepared from tissue of a primary colonic adenocarcinoma, sigmoid colon, moderately well differentiated grade II, staging pT3, pN1, removed from a 69 year old white female of blood type O, RH positive. The patient had not received therapy.

The tissue was minced and lysed by treatment with guanidinium-thiocyanate according to Chirgwin, J. M. et al. (1979, Biochemistry 18 5294–5299). Total RNA was isolated by guanidinium thiocyanate-phenol-chloroform extraction (Chomczyrski et al. 1987, Anal. Biochem. 162:156–159). Poly $A^+$ RNA was isolated on an oligo-dt column (Aviv and Leder, 1972, Proc. Natl. Acad. Sci. USA 69:1408–1412).

One tenth of the cDNA was subjected to the polymerase chain reaction using standard conditions (PCR Technology-Principles and Applications for DNA Amplifications, H. E. Erlich, ed. Stockton Press, New York, 1989) and the same pool of primers used for amplification of MCK-10 (See, Section 6.1.1., lines 4–16). Thirty-five cycles were carried out (Annealing 55° C., 1 min; Extension 72° C., 2 min: Denaturation 94° C., 1 min.). The reaction products were subjected to polyacrylamide gel electrophoresis. Fragments of the expected size were isolated, digested with the restriction enzyme EcoRI, and subcloned into pBluescript vector (Stratagene) using standard techniques (Current Protocols in Molecules Biology, eds. M. Ausubel et al., John Wiley & Sons, New York, 1988). The subcloned PCR products were sequenced by the method of Sanger et al. (Proc. Natl. Acad. Sci. USA 74, 5463–5467) using T7-Polymerase (Boehringer Mannheim).

The CCK-2 PCR fragment was used to screen a human placenta library in lambda ZAP. The longest cDNA insert ⁻1300 bp was digested with the restriction enzymes EcoRI/Ncol to obtain a 5' end probe of 200 bp. Rescreening of the human placenta library yielded in a cDNA clone which encoded the entire CCX-2 protein (subcloning of positive bacteriophages clones into pBluescript vector was done by the in vivo excision protocol (stratagene)). The DNA sequence and the deduced amino acid sequence of CCK-2 is shown in FIG. 3.

7.2. Results 7.2.1. Cloning and Characterization of CCK-2

An additional member of the MCK-10 receptor tyrosine kinase family was identified using a polymerase chain reaction and cDNA prepared from colonic adenocarcinoma RNA. The nucleotide sequence of the novel receptor, designated CCK-2, is presented in FIGS. 3A and 3B. Analysis of the CCK-2, nucleotide sequence and encoded amino acid sequence indicated significant homology with MCK-10 throughout the extracellular, transmembrane and intracellular region of the MCK-10 receptor. The regions of homology between CCK-2 and MCK-10 extend into the N-terminus consensus sequence for the discoidin I like family of proteins. (Poole et al. 1981, J. Mol. Biol. 153, 273–289). The homology between CCK-2 and MCK-10 is diagramed in FIGS. 4A–4C.

8. Deposit of Microorganisms

The following organisms were deposited with the American Type Culture Collection (ATCC), 12301 Parklawn Drive, Rockville, Md. 20852.

| Strain Designation | Containing | Accession No. |
|---|---|---|
| CCK-2 | pCCK-2 | 69468 |
| MCK-10-1 | pMCK-10-1 | 69464 |
| MCK-10-2 | pMCK-10-2 | 69465 |
| MCK-10-3 | pMCK-10-3 | 69466 |
| MCK-10-4 | pMCK-10-4 | 69467 |

The present invention is not to be limited in scope by the exemplified embodiments or deposited organisms which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

It is also to be understood that all base pair sizes given for nucleotides are approximate and are used for purposes of description.

What is claimed is:

1. A method for identifying an antagonist of MCK-10, comprising: (a) contacting a cell line that expresses either (i) an MCK-10 protein comprising the amino acid sequence of SEQ ID NO. 2, or (ii) a splice variant thereof, with a test compound; (b) determining whether said test compound inhibits the binding of a ligand to said MCK-10 protein or splice variant thereof, and (c) subsecuently determining the activity of said MCK-10 protein or splice variant thereof, wherein a test compound that inhibits binding of a ligand to said MCK-10 protein or splice variant thereof, and reduces or inhibits the activity of the MCK-10 protein or splice variant thereof, is an antagonist of MCK-10.

2. The method of claim 1, wherein said cell line is a genetically engineered cell line.

3. The method of claim 1, wherein said cell line endogenously expresses the MCK-10.

4. A method for identifying an antagonist of MCK-10, comprising: (a) contacting a cell line that expresses either (i) an MCK-10 protein comprising the amino acid sequence of SEQ ID NO. 2, or (ii) a splice variant thereof, with a test compound; (b) determining whether said test compound inhibits the binding of a ligand to said MCK-10 protein or splice variant thereof, thereby effecting a cellular change in said cell line; and (c) subsequently determining the activity of said MCK-10 protein or splice variant thereof, wherein a test compound that effects a cellular change in said cell line and reduces or inhibits the activity of the MCK-10 protein or splice variant thereof is an antagonist of MCK-10.

5. A method for identifying a peptide that binds to MCK-10, comprising: (a) contacting an MCK-10 protein comprising the amino acid sequence of SEQ ID NO. 2, or a splice variant thereof, with a random peptide library; (b) isolating a complex comprising an (i) MCK-10 protein, or splice variant thereof, and (ii) a peptide; and (c) determining the sequence of the peptide of said complex.

6. A method for identifying a compound that modulates MCK-10 activity, comprising: (a) contacting a cell line that expresses either (i) an MCK-10 protein comprising the amino acid sequence of SEQ ID NO. 2, or (ii) a splice variant thereof, with a test compound; and (b) determining whether said test compound modulates the activity of said MCK-10 protein or splice variant thereof.

7. The method of claim 6, wherein said test compound inhibits the activity of said MCK-10 protein or splice variant thereof.

8. A method for identifying an antagonist of MCK-10, comprising: (a) contacting an MCK-10 protein comprising the amino acid sequence of SEQ ID NO. 2, or a splice variant thereof, with a test compound; (b) determining whether said test compound inhibits the binding of a ligand to said MCK-10 protein or splice variant thereof; and (c) subsequently determining the activity of said MCK-10 protein or splice variant thereof, wherein a test compound that inhibits binding of a ligand to said MCK-10 protein or splice variant thereof, and reduces or inhibits the activity of the MCK-10 protein or splice variant thereof, is an antagonist of MCK-10.

9. A method for identifying a compound that modulates MCK-10 activity, comprising: (a) contacting an MCK-10 protein comprising the amino acid sequence of SEQ ID NO. 2, or a splice variant thereof, with a test compound; and (b) determining whether said test compound modulates the activity of said MCK-10 protein or splice variant thereof.

10. The method of claim 9, wherein said test compound inhibits the activity of said MCK-10 protein or splice variant thereof.

* * * * *